US008628579B2

(12) United States Patent
Ries et al.

(10) Patent No.: US 8,628,579 B2
(45) Date of Patent: Jan. 14, 2014

(54) SYSTEMS AND METHODS FOR PROSTHETIC KNEE

(75) Inventors: Michael D. Ries, Tiburon, CA (US); Mark J. Mooradian, Phoenix, AZ (US); Joshua A. Butters, Chandler, AZ (US); Daniel F. Justin, Orlando, FL (US)

(73) Assignees: IMDS Corporation, Providence, UT (US); Michael D. Ries, Tiburon, CA (US)

( * ) Notice: Subject to any disclaimer, the term of this patent is extended or adjusted under 35 U.S.C. 154(b) by 16 days.

(21) Appl. No.: 13/188,699

(22) Filed: Jul. 22, 2011

(65) Prior Publication Data
US 2011/0313534 A1 Dec. 22, 2011

Related U.S. Application Data

(63) Continuation-in-part of application No. 12/606,326, filed on Oct. 27, 2009.

(60) Provisional application No. 61/233,081, filed on Aug. 11, 2009, provisional application No. 61/367,292, filed on Jul. 23, 2010, provisional application No. 61/373,393, filed on Aug. 13, 2010.

(51) Int. Cl.
*A61F 2/38* (2006.01)

(52) U.S. Cl.
USPC ..................... 623/20.27; 623/20.29

(58) Field of Classification Search
USPC .......... 623/20.27, 20.29, 20.35, 20.24, 20.25, 623/20.28
See application file for complete search history.

(56) References Cited

U.S. PATENT DOCUMENTS

| 4,224,697 A | 9/1980 | Murray |
| 4,634,444 A | 1/1987 | Noiles |
| 4,714,472 A | 12/1987 | Averill |
| 5,071,438 A | 12/1991 | Jones |

(Continued)

FOREIGN PATENT DOCUMENTS

| DE | 202010000037 | 3/2010 |
| WO | WO0182842 A1 | 11/2001 |
| WO | WO2006118822 | 11/2006 |
| WO | WO2011059759 | 5/2011 |

OTHER PUBLICATIONS

Biomet *AGC Total Knee System* Product Brochure May 2009.

(Continued)

*Primary Examiner* — Bruce E Snow
*Assistant Examiner* — Melissa Hoban
(74) *Attorney, Agent, or Firm* — G. Jo Hays; James Larson; James M. Pinkston

(57) ABSTRACT

A knee prosthesis including femoral and tibial implants, a tibial insert and a cam post assembly. The femoral implant is secured to a femur and has a cam feature and condyles. The tibial implant is secured to a tibia. The tibial insert has articulating surfaces that match the contours of the condyles of the femoral implant, and may have a medial boss that aligns with the tibial implant to provide rotation about a medially displaced rotation axis. A cam post is secured to the tibial implant and passes through a channel of the tibial insert. A motion limiting structure provides limits to motion between the tibial insert and the tibial baseplate. The cam post assembly interacts with the femoral implant cam feature and allows more anatomically correct rollback and femoral external rotation during knee flexion, and varus/valgus support to the femur.

19 Claims, 51 Drawing Sheets

(56) References Cited

U.S. PATENT DOCUMENTS

| | | | |
|---|---|---|---|
| 5,071,738 A | 12/1991 | Mizukura | |
| 5,330,533 A | 7/1994 | Walker | |
| 5,330,534 A | 7/1994 | Herrington | |
| 5,370,701 A * | 12/1994 | Finn | 623/20.25 |
| 5,387,240 A | 2/1995 | Pottenger | |
| 5,413,604 A | 5/1995 | Hodge | |
| 5,480,446 A | 1/1996 | Goodfellow | |
| 5,658,342 A | 8/1997 | Draganich | |
| 5,755,801 A | 5/1998 | Walker | |
| 5,755,804 A * | 5/1998 | Schmotzer et al. | 623/20.24 |
| 5,879,392 A | 3/1999 | McMinn | |
| 5,879,394 A | 3/1999 | Ashby | |
| 5,928,286 A | 7/1999 | Ashby | |
| 6,013,103 A | 1/2000 | Kaufman | |
| 6,039,764 A | 3/2000 | Pottenger | |
| 6,080,195 A | 6/2000 | Colleran | |
| 6,099,570 A | 8/2000 | Livet | |
| 6,165,223 A | 12/2000 | Metzger | |
| 6,203,576 B1 | 3/2001 | Afriat | |
| 6,214,052 B1 | 4/2001 | Burkinshaw | |
| 6,296,666 B1 | 10/2001 | Gardner | |
| 6,413,279 B1 * | 7/2002 | Metzger et al. | 623/20.29 |
| 6,558,427 B2 | 5/2003 | Leclercq | |
| 6,629,999 B1 | 10/2003 | Serafin | |
| 6,764,516 B2 | 7/2004 | Pappas | |
| 6,773,461 B2 * | 8/2004 | Meyers et al. | 623/20.24 |
| 6,797,005 B2 | 9/2004 | Pappas | |
| 6,972,039 B2 | 12/2005 | Metzger | |
| 6,974,481 B1 | 12/2005 | Carson | |
| 6,986,791 B1 | 1/2006 | Metzger | |
| 7,105,027 B2 | 9/2006 | Lipman | |
| 7,232,465 B2 | 6/2007 | Keller | |
| 7,572,292 B2 | 8/2009 | Crabtree | |
| 7,658,767 B2 | 2/2010 | Wyss | |
| 2001/0003803 A1 | 6/2001 | Leclercq | |
| 2003/0153980 A1 | 8/2003 | Brack | |
| 2005/0209702 A1 | 9/2005 | Todd | |
| 2007/0100462 A1 | 5/2007 | Lang | |
| 2007/0100463 A1 | 5/2007 | Aram | |
| 2007/0135925 A1 | 6/2007 | Walker | |
| 2007/0135926 A1 | 6/2007 | Walker | |
| 2008/0009950 A1 | 1/2008 | Richardson | |
| 2008/0097616 A1 | 4/2008 | Meyers | |
| 2008/0114464 A1 | 5/2008 | Barnett | |
| 2008/0119940 A1 | 5/2008 | Otto | |
| 2008/0243259 A1 | 10/2008 | Lee | |
| 2008/0300690 A1 | 12/2008 | Burstein | |
| 2009/0043396 A1 | 2/2009 | Komistek | |
| 2009/0088861 A1 | 4/2009 | Tuke | |
| 2009/0299482 A1 * | 12/2009 | Metzger et al. | 623/20.29 |

OTHER PUBLICATIONS

Biomet *Alpina APR* Product Info Website: http://www.biomet.co.uk/index.php?id=17313 Jan. 3, 2007.
Biomet Europe, *Vanguard System Summary* May 2009.
Corin *Corin Rotaglide & Mobile Bearing*, Product Brochure, Jan. 20, 2011 p. 1-3.
Depuy *Finsbury Dual Bearing Knee*, Feb. 10, 2010.
Depuy *LCS Complete Product Brochure*, May 2009.
Depuy *Sigma Rotating Platform* Product Brochure, May 2009.
Kyocera *Kyocera Bisurface Mechanical Comparison of 2 Posterior Stabilizing Designs*, Journal of Arth. col. 17 No. 5 2002.
Medacta *GMK Primary* Product Brochure Nov. 26, 1999 Rev. 00[1].
Smith & Nephew *Journey BCS* Product Brochure May 2009.
Spherocentric Knee *Biomechanical Testing and Clinical Trial*, JNJS 1977 Vo. 59 pp. 602-616.
Stryker *NRG Product Brochure*, Aug. 2009.
Wright Medical *MK056-206 Advance*, Family Brochure May 2009.
Zimmer *NexGen Implant Options*, Product Brochure Aug. 2009.
Zimmer *NexGen Mobile Bearing LPS Flex and LPS Mobile Bearing Knee*, Product Brochure Aug. 2009.
Smith & Nephew Journey BCS *ORS White Paper Poster #1987 at 2008 ORS Annual Meeting* San Francisco, CA.
Smith & Nephew Journey BCS *Design Rationale* 2006.
Walker, Peter S.; Biomechanical Principles of Total Knee Replacement Design, Basic Orthopaedic Biomechanics $2^{nd}$ ed. 1997 pp. 461-493.
Douglas, Dennis A.; *Factors Affecting Flexion after Total Knee Arthroplasty*, Clinical Orthopaedics and Related Research No. 464, pp. 53-60 2007.
Kelly, Michael A. *In vivo kinematic evaluation and design considerations related to high flexion in total knee arthroplasty.* Journal of Biomechnics 38 (2005) 277-284.
Halloran, Jason P.; *Eplicit finite element modeling of total knee replacement mechanics*, Journal of Biomechanics 28 (2005) 323-331.
Morra, Edward A.; *Polymer Insert Stress in Total Knee Designs During High Flexion Activities: A Finite Element Study*, Orthopaedic Research Laboratories Cleveland Ohio AAOS 2005 pp. 1-4.
Greenwald, Seth A. *Mobile-Bearing Knee Systems: Ultra-High Molecular Weght Polyethylene Wear and Design Issues*, AAOS Instructional Course Lectures, vol. 54 2005 pp. 195-205.
Vertullo, Christopher J. *Mobile Bearings in Primary Knee Arthroplasty* Journal of the American Academy of Orthopaedic Surgeons vol. 9, No. 6 Nov./Dec. 2001.
Morra, Edward A.; *The Influence of Contemporary Knee Design on High Flexion II: A Kinematic Comparison with the Normal Knee*. Orthopaedic Research Laboratories Cleveland, Ohio, AAOS 2009.
Zimmer:Comprehensive Natureal-Knee Family. (2006) Website: www.Zimmer.co.uk/z/ctl/op/global/action/1/id/7802/template/MP.com.
Zimmer: *Gender Solutions Natural-Knee Flex System*. Product Brochure (2007).
Cosset; Larry MD.: *Evolution of the Low Contact Stress (LCS) Complete Knew System*. Ortrhopedics, Feature Article: Sepember (2006) vol. 29, No. 9 Supplement pp. S17-S22.

* cited by examiner

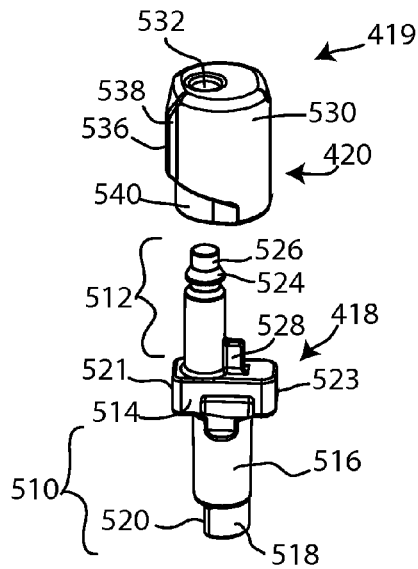
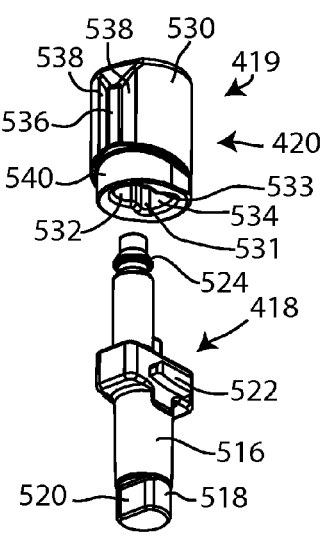
Fig. 37A
Fig. 37B
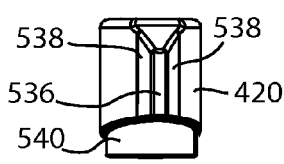
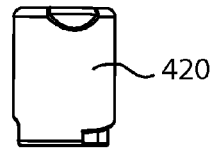
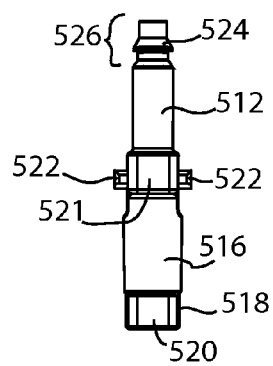
Fig. 37C
Fig. 37D

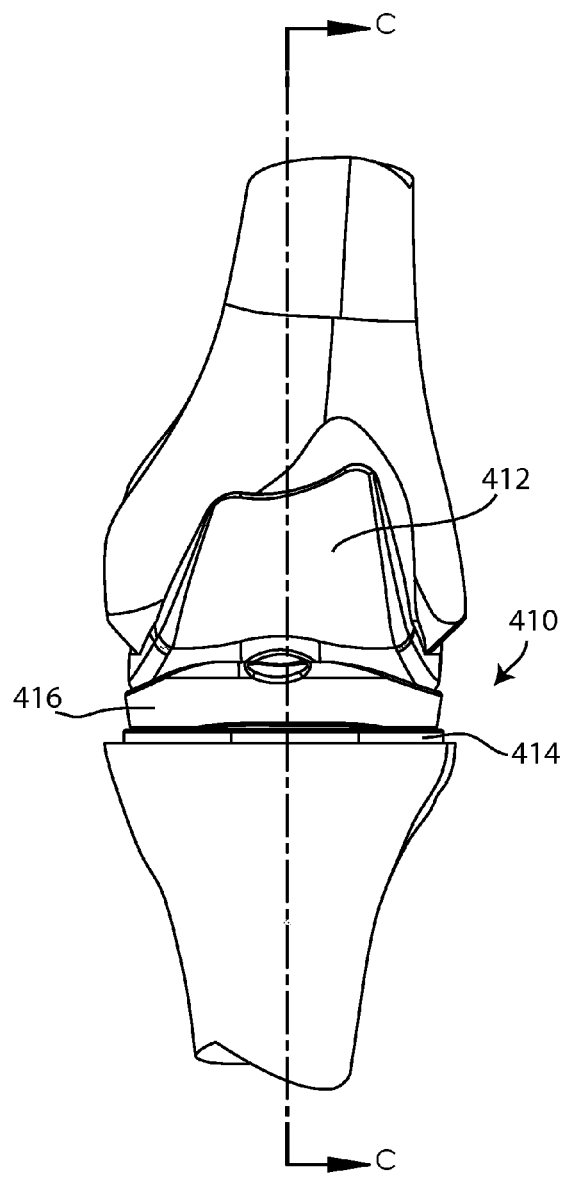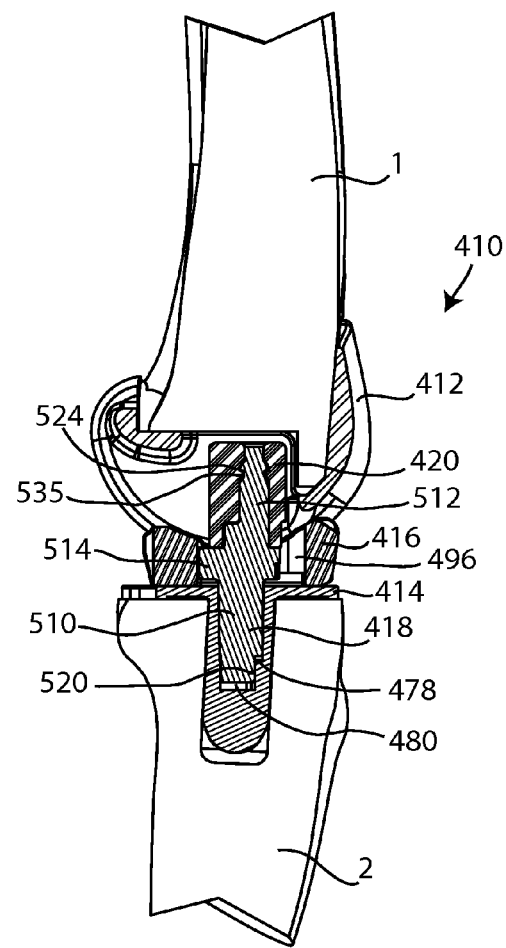
Fig. 39A
Fig. 39B

SYSTEMS AND METHODS FOR PROSTHETIC KNEE

CROSS-REFERENCE TO RELATED APPLICATIONS

This application is a continuation-in-part of pending U.S. patent application Ser. No. 12/606,326 filed 27 Oct. 2009 and is entitled SYSTEMS AND METHODS FOR MOBILE BEARING PROSTHETIC KNEE, which is a non-provisional of:

U.S. Provisional Patent Application No. 61/233,081 filed 11 Aug. 2009 and is entitled MOBILE BEARING PROSTHETIC KNEE.

This application also claims benefit to:

Pending prior U.S. Provisional Patent Application No. 61/367,292 filed 23 Jul. 2010 and is entitled MOBILE BEARING PROSTHETIC KNEE WITH VARUS/VALGUS CONSTRAINT; and Pending prior U.S. Provisional Patent Application No. 61/373,393 filed 13 Aug. 2010, and is entitled PROSTHETIC KNEE WITH CAPTIVE TIBIAL INSERT.

Each of the above-referenced documents is herein incorporated by reference in its entirety.

BACKGROUND OF THE INVENTION

1. The Field of the Invention

The present invention relates generally to a total knee replacement by using a prosthetic knee, and more particularly, providing a more functionally correct motion of the prosthetic knee similar to kinematic motion of a normal, non-prosthetic knee, during knee flexion.

2. The Relevant Technology

One attribute of normal knee flexion is that, as the knee flexes, the contact points of the femur on the tibia move posteriorly. This posterior movement of the contact points is known as rollback. Also, normal knee rollback is much more pronounced on the lateral side of the knee than the medial side, which results in femoral external rotation during knee flexion.

Other prosthetic knees currently on the market do not use two separate fully guided motion paths, and as a consequence may not reproduce normal knee kinematics and need to use wear components made of polyethylene, or similar material, to accommodate the less-guided sliding that occurs during knee flexion. These existing methods and procedures may not be as effective as desired. There is a need to have a tibial insert (also known and synonymously referred throughout the specification and claims herein as a "tibial bearing", "insert", "bearing insert", or "tibial bearing insert") of a prosthetic knee roll back on a medial pivot axis causing greater rollback on the lateral side than the medial side, like a normal, non-prosthetic knee.

SUMMARY

Some embodiments set forth in this disclosure are summarized below.

According to a first aspect, the present invention provides a knee replacement system including: a femoral knee implant including a pair of condyles and a bone facing side shaped to lie against a resected surface of a femur; a tibial baseplate including a tibia facing surface and a superior surface, wherein the tibia facing surface is shaped to lie against a resected surface of a tibia; a tibial bearing having a baseplate facing side, a condylar articulation side, and a channel which passes through the tibial bearing along a direction generally perpendicular to the baseplate facing side; a support post assembly including a post which projects superiorly relative to the superior surface of the tibial baseplate and extends through the channel of the tibial bearing; and a structure engaging the tibial baseplate and the tibial bearing to limit motion between the tibial baseplate and the tibial bearing.

In an embodiment, the knee replacement system further includes a first rotation axis extending through the tibial baseplate and the tibial bearing substantially perpendicular to the superior surface of the tibial baseplate and the baseplate facing side of the tibial bearing, the first rotation axis medially displaced relative to the geometric centers of the tibial baseplate and the tibial bearing, wherein the tibial bearing rotates about the medial rotation axis during articulation of the knee replacement system.

In an embodiment, the post is removably attachable to the tibial baseplate.

In an embodiment, the support post assembly engages with the femoral implant to provide varus/valgus stability to the femoral implant.

In an embodiment, the support post assembly includes a sleeve removably mounted onto the post and rotatable about the post. The embodiment may further include a second rotation axis separate from and not co-axial with the first rotation axis, wherein the sleeve rotates about the second rotation axis. During articulation of the knee replacement system the tibial bearing rotates relative to the tibial baseplate in a first direction and the sleeve rotates about the post in a second direction, the second direction opposite from the first direction. The embodiment may further include a second rotation limiting mechanism, wherein the second rotation limiting mechanism limits the rotation of the sleeve relative to the post.

In an embodiment, the structure projects superiorly from the baseplate superior surface. The structure may directly contact a wall of the channel to limit rotation of the tibial bearing relative to the tibial baseplate.

In an embodiment, the post is unrotatable relative to the tibial baseplate.

In an embodiment, the post is attached to the tibial baseplate through a Morse taper fitting.

In an embodiment, the post comprises a key feature and the tibial baseplate comprises a corresponding key feature, wherein the key features directly engage each other to prevent rotation of the post relative to the tibial baseplate.

In an embodiment, the support post assembly directly contacts the femoral implant to provide varus/valgus stability to the femoral implant.

In an embodiment, the femoral component comprises first and second intercondylar walls, wherein the support post assembly contacts at least one of the intercondylar walls to provide varus/valgus stability to the femoral implant.

In an embodiment, the position of the tibial bearing is fixed relative to the tibial baseplate during articulation of the knee replacement system. The post may be removably attachable to the tibial baseplate. The support post assembly may engage with the femoral implant to provide varus/valgus stability to the femoral implant. A sleeve may be removably mounted onto the post and rotatable about the post.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 34E is a posterior view of the femoral implant of FIG. 33 positioned in flexion;

FIG. 37A is a perspective exploded side view of the cam post assembly of FIG. 33; FIG. 37B is a perspective inferior exploded view of the cam post assembly of FIG. 33; FIG. 37C is an anterior exploded view of the cam post assembly of FIG. 33; FIG. 37D is a posterior exploded view of the cam post assembly of FIG. 33;

FIG. 39A is a anterior view of the prosthesis of FIG. 33 implanted in a tibia and a femur; FIG. 39B is an medial cross-sectional view of the prosthesis of FIG. 33 taken along line C-C;

DETAILED DESCRIPTION OF THE PREFERRED EMBODIMENTS

The present invention relates to systems and methods used in orthopaedic surgery, and in particular, to total knee arthroplasty. Those of skill in the art will recognize that the systems and methods described herein may be readily adapted for any total joint arthroplasty procedure. Those of skill in the art will also recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

Figure 1:
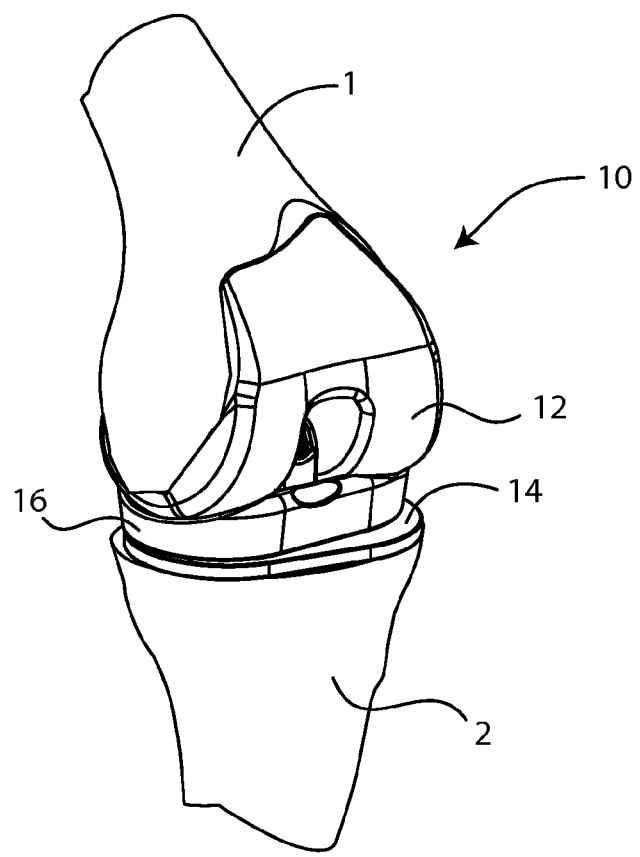
FIG. 1 illustrates a perspective view of the prosthesis, with a femur, a tibia, a tibial baseplate, a tibial insert, a femoral implant and a reference arrow diagram.
Figure 1:
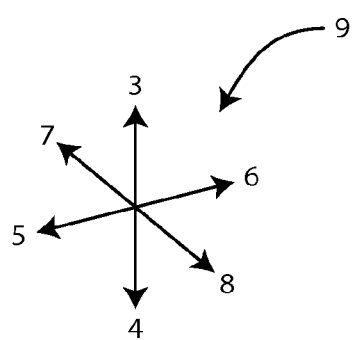

Referring to FIG. 1, a perspective view illustrates a knee prosthesis, e.g. a mobile bearing knee prosthesis 10, according to one embodiment of the invention, implanted in a knee. This figure and subsequent figures may be oriented according to the reference arrow diagram 9, having a superior direction 3, an inferior direction 4, a medial direction 5, a lateral direction 6, a posterior direction 7, and an anterior direction 8. In this application, "left" and "right" are used with reference to a posterior view. "Medial" refers to a position or orientation toward a sagittal plane (i.e., plane of symmetry that separates left and right sides of the body from each other), and "lateral" refers to a position or orientation relatively further from the sagittal plane. The knee prosthesis 10 may comprise a tibial baseplate 14, a tibial insert 16 and femoral implant 12.

Figure 2:
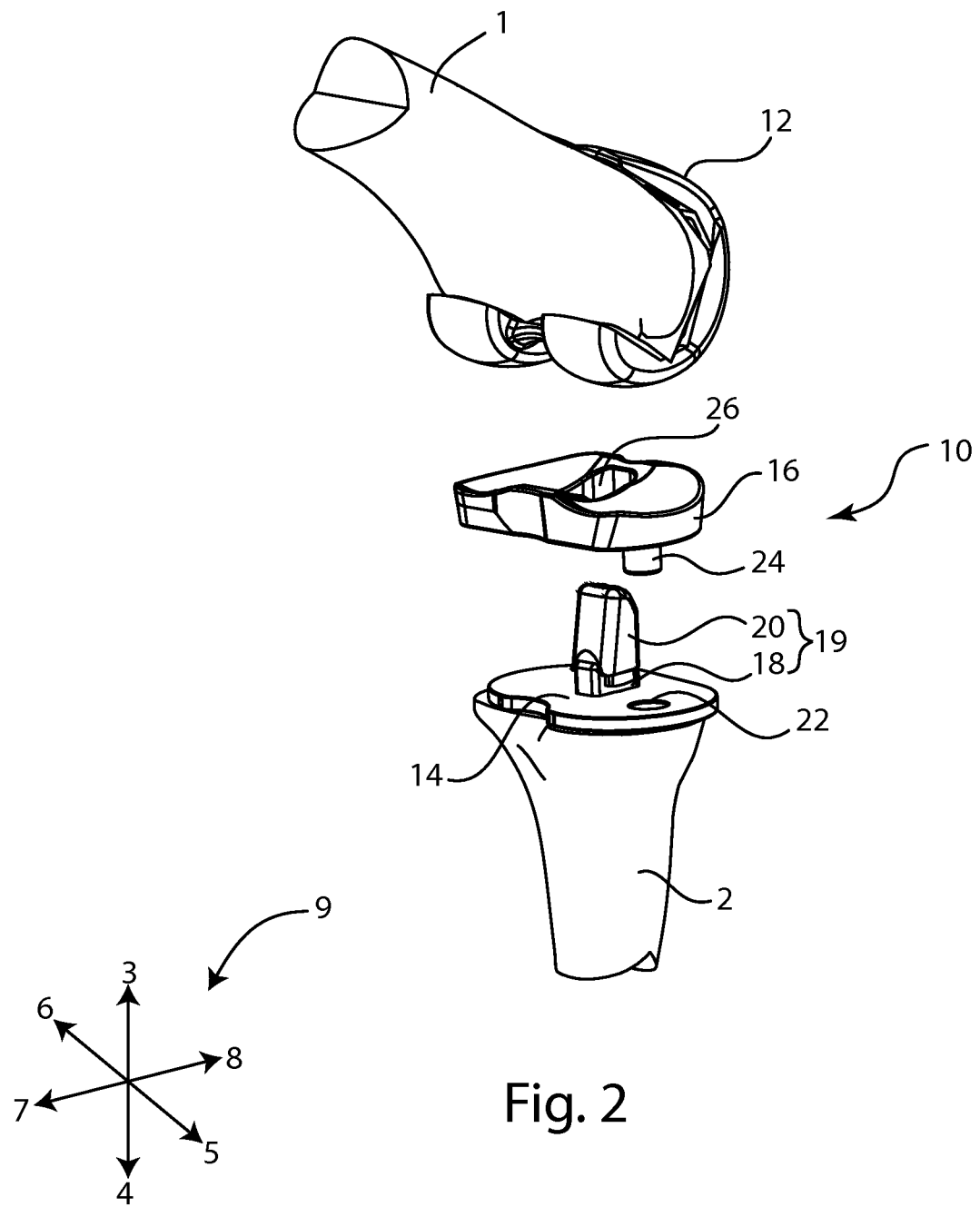
FIG. 2 illustrates an exploded perspective view of the prosthesis of FIG. 1 with the femur, the tibia, the tibial baseplate with a tibial baseplate aperture, the tibial insert with a tibial insert boss and a tibial insert hole, the femoral implant, and a cam post with an outer sleeve.
Figure 3:
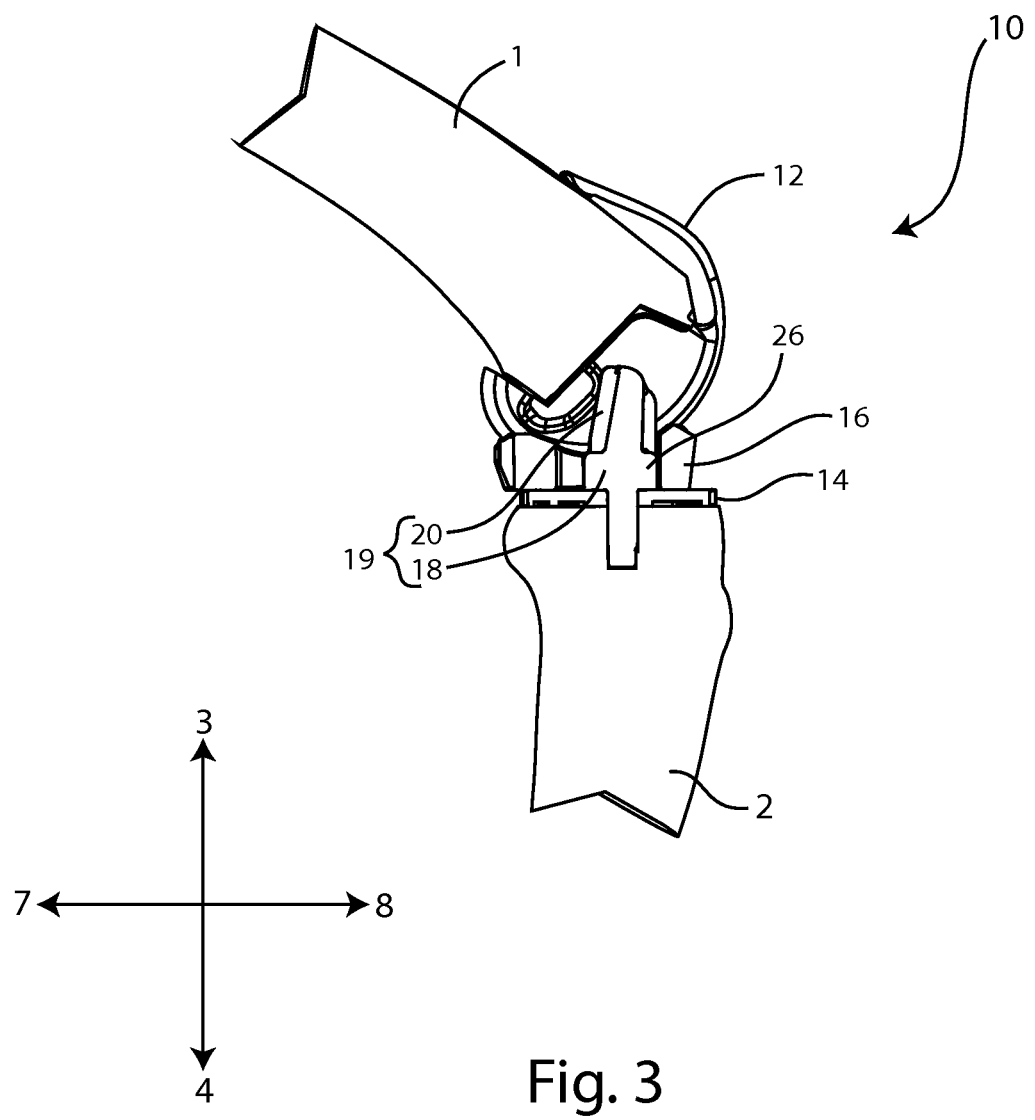
FIG. 3 illustrates a cross sectional side view of the prosthesis of FIG. 1 with the femur, tibia, tibial implant, tibial insert, femoral implant, and the cam post with the outer sleeve.

Referring to FIGS. 2 and 3, the prosthetic knee 10 comprises the tibial baseplate 14, attached to the resected tibia 2, a cam post 19 may be attached to the tibial baseplate 14 and may either be a modular or non-modular part of the baseplate. The cam post may also be referred to as a cam post assembly. The cam post 19 helps guide the rotation of the femoral component and tibial insert 16 during flexion of the prosthetic knee 10. The cam post 19 of this embodiment is of two-piece construction, with a metallic cam post core 18 and a polymer outer wear sleeve 20. However, either the cam post core 18 or the sleeve 20 may be comprised of other biocompatible materials. A tibial insert 16 may be rotationally connected to the tibial baseplate 14, rotating about an axis within a tibial insert channel 26 which axis of rotation is medial to the midline of the tibia. A femoral implant 12 may be attached to a resected femur 1, which is supported by the tibial insert 16 and which slidably engages with the cam post 19 to guide the rotation of the tibial insert and posterior movement of the femoral component 12 during flexion of the prosthetic knee 10.

For any of the parts of the prosthetic knees disclosed herein any biocompatible material may be used, including but not limited to stainless steels, titanium and its alloys, cobalt-chrome and its alloys, ceramics, composite materials, and polymers.

Figure 4:
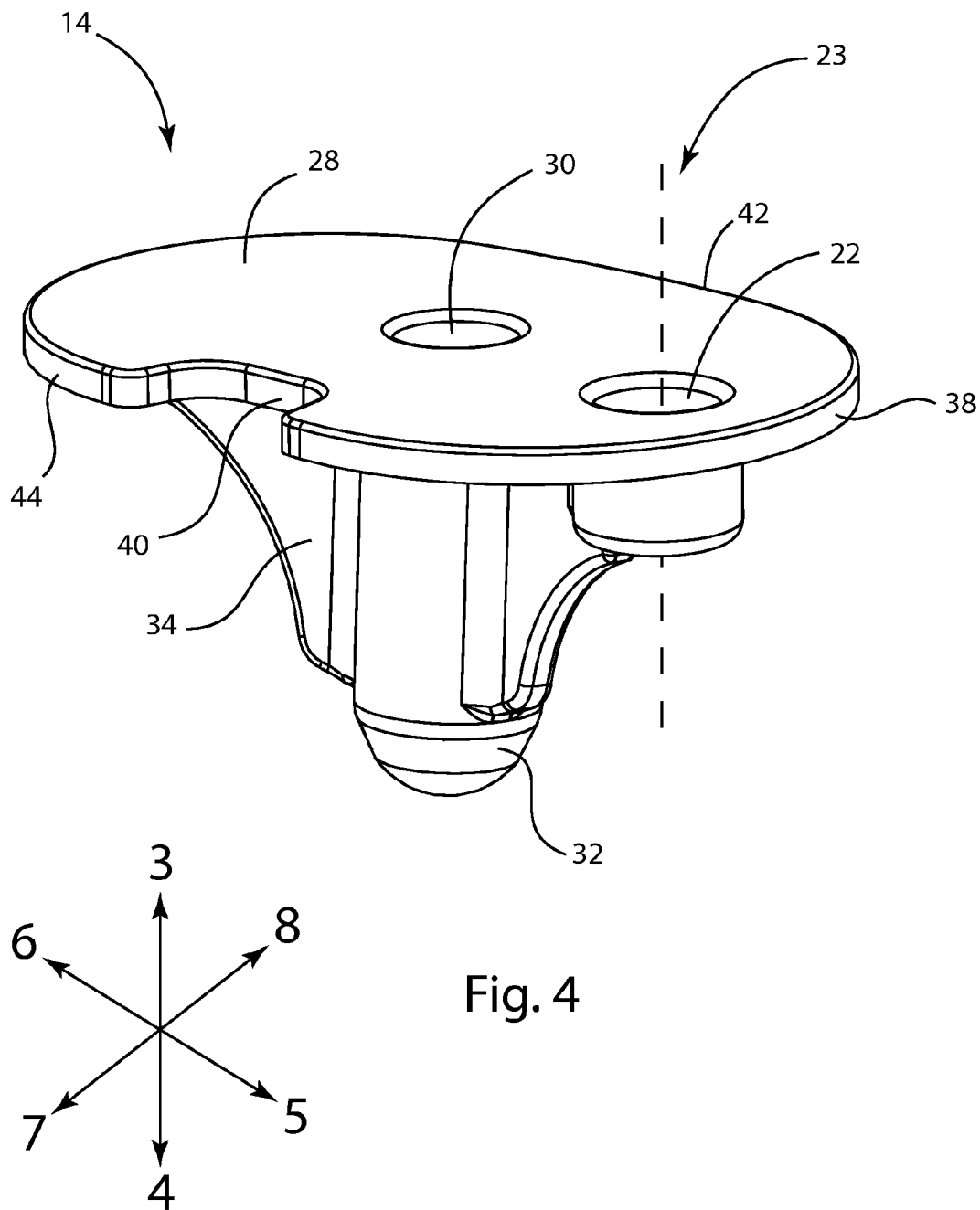
FIG. 4 illustrates a perspective top view of one embodiment of the tibial baseplate of FIG. 1 with the tibial baseplate cavity for retention of a boss of the tibial insert, and a tibial baseplate hole for passage of the cam post, on a tibial baseplate bearing surface, a keel extending into the tibia and at least one wing.
Figure 5:
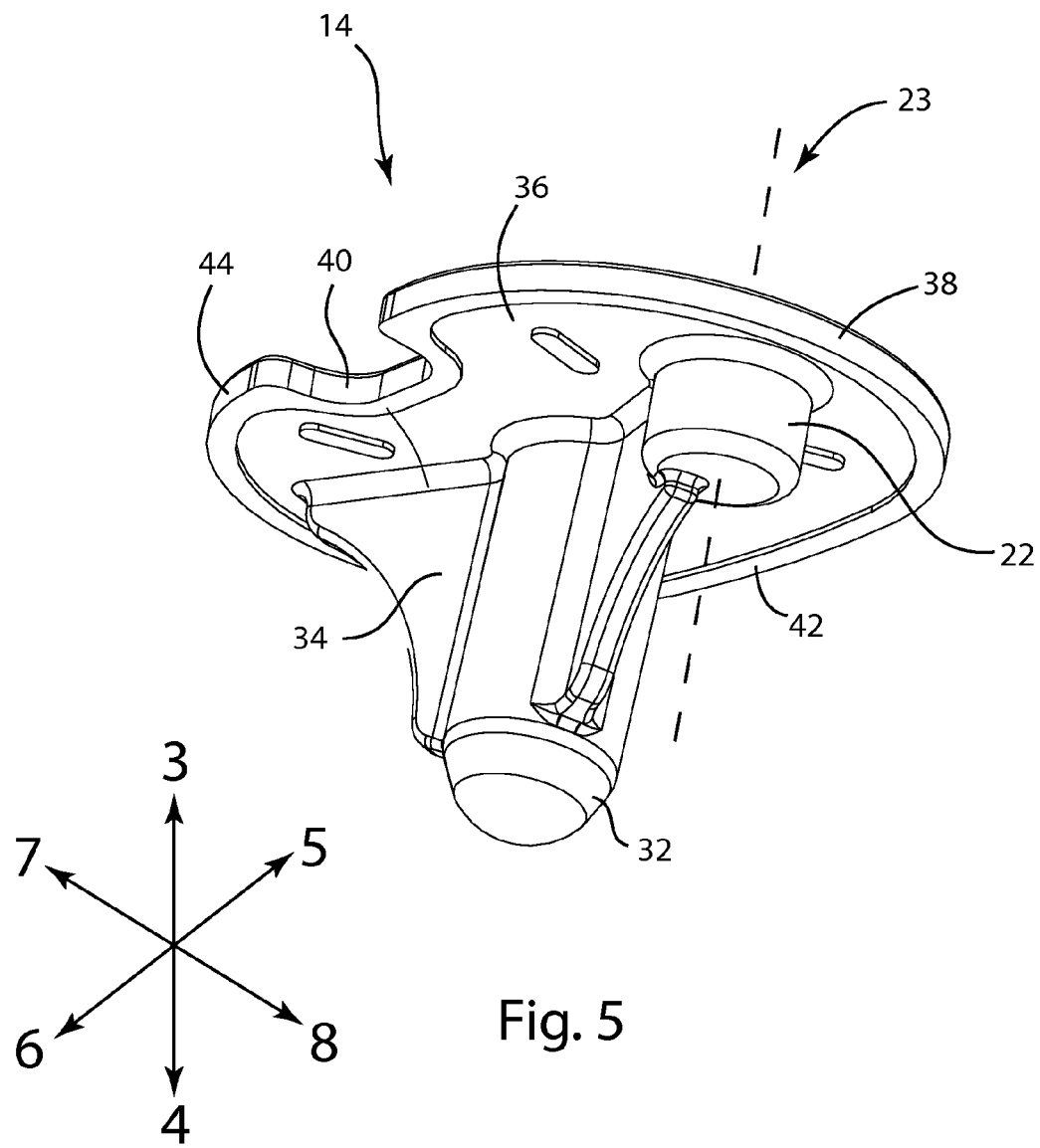
FIG. 5 illustrates a perspective bottom view of the tibial baseplate of FIG. 4 with the at least one wing, the keel, the tibial baseplate aperture and the tibial baseplate cam post aperture.

Referring to FIGS. 4 and 5, the tibial baseplate 14 may be made of a cobalt-chromium alloy. Other metals, such as titanium alloys or other composites may be used for the baseplates disclosed herein, as well as polymer, ceramic, or other composite materials. In this embodiment the tibial baseplate 14 is rigidly attached to the resected tibia 2 on a tibia facing surface 36. Protruding inferiorly from the tibia facing surface is a keel 32 and at least one peg 34. The keel 32 may be driven into the core of the resected tibia 2. The at least one baseplate wing 34 extending from the tibia facing surface the length of the keel 32 and in communication with the keel may also be driven into the resected tibia 2 for added fixation and stabilization. Attachment of the tibial baseplate 14 may also be made by using cement, force fit, bone in-growth, bone screws or other method known in the art. A superior surface 28 of the tibial baseplate 14 may be substantially flat and acts as a support for the tibial insert 16. The superior surface 28 of the tibial baseplate 14 may be polished to minimize wear between the tibial baseplate 14 and the tibial insert 16. The tibial baseplate 14 includes a hole 30, for the mounting of cam post 19, which may be positioned substantially in the geometric center of the tibial baseplate 14 and is deep enough to receive at least a portion of the cam post 19. The tibial baseplate may also include a cavity 22 apart from the hole 30 and positioned substantially medial from the geometric center and apart from a periphery 38 of the tibial baseplate 14. The cavity 22 may provide a rotational medial axis 23 for the tibial insert 16 allowing for rotational movement of the tibial insert along that medial axis. In this embodiment, along a posterior side 44, opposite an anterior side 42, of the periphery 38 of the tibial baseplate 14 comprises a tibial baseplate notch 40 which may allow room for retention of the posterior cruciate ligament (PCL) or another ligament behind the plate 14.

Referring to FIG. 5, a perspective view illustrates the tibia-facing side 36 of the tibial baseplate 14. The keel 32 and the at least one baseplate wing 35 may comprise porous material that encourages bone in-growth.

Figure 6:
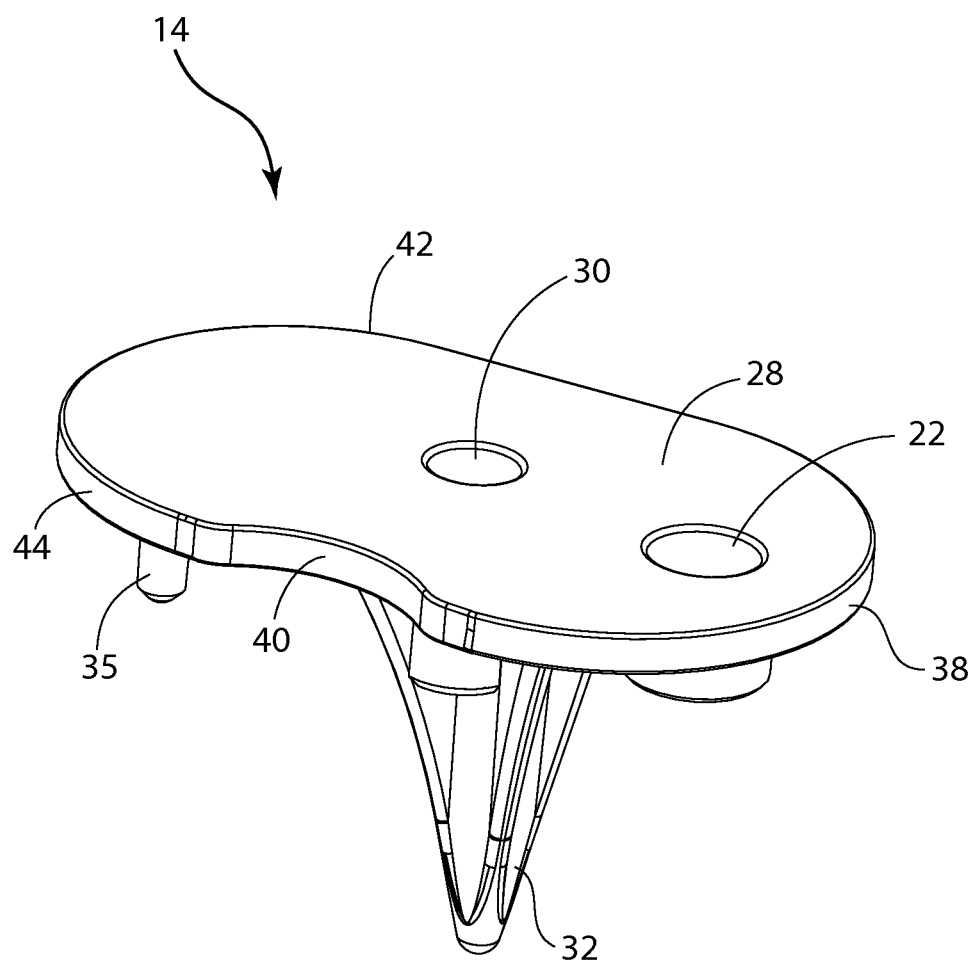
FIG. 6 illustrates a perspective top view of a different embodiment of the tibial baseplate of FIG. 1 with the tibial baseplate aperture and a tibial baseplate cam post aperture on a tibial baseplate bearing surface, a keel and at least one peg.
Figure 6:
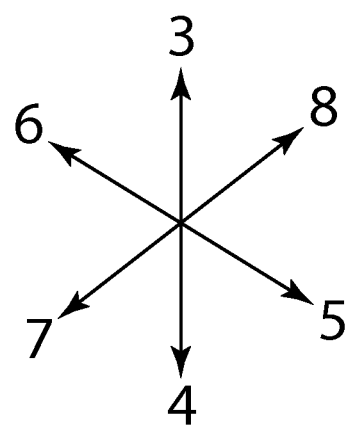
Figure 7:
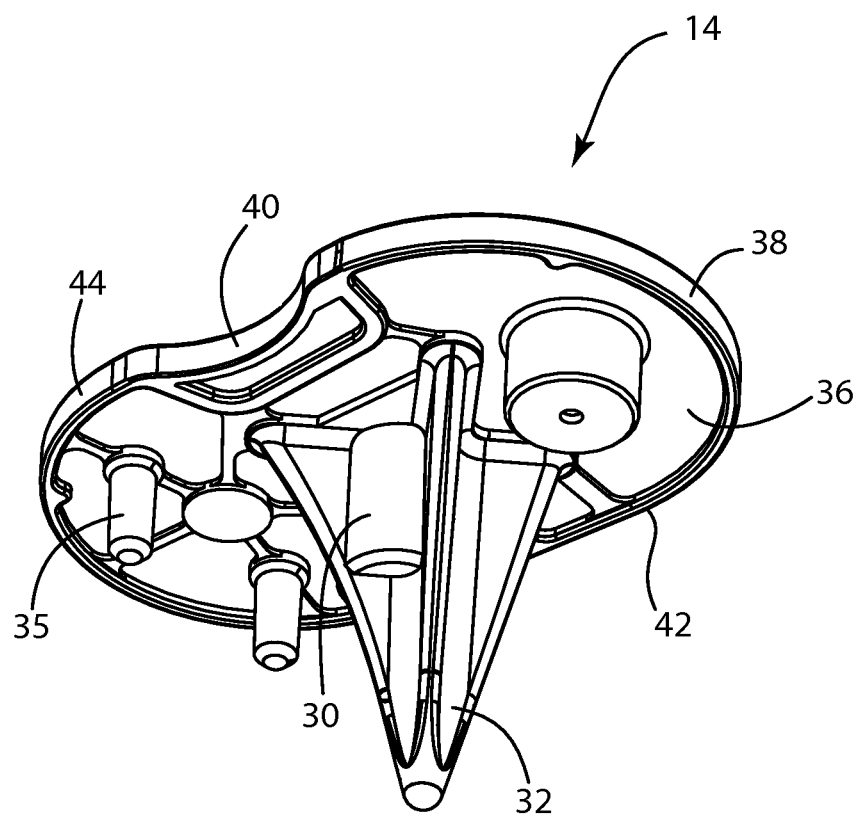
FIG. 7 illustrates a perspective bottom view of the tibial baseplate of FIG. 6 with the at least one peg, the keel, the tibial baseplate aperture and the tibial baseplate cam post) aperture.
Figure 7:
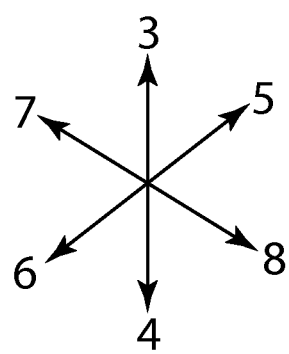

Referring to FIGS. 6 and 7, an alternate embodiment of the keel 32 is present with at least one peg 35. In this and other embodiments of the invention the size, shape and placement of the keel 32 may vary. The pegs 35 may not need to be present at all Likewise, the tibial baseplate notch 40 can vary in size, shape and placement as well.

Figure 8:
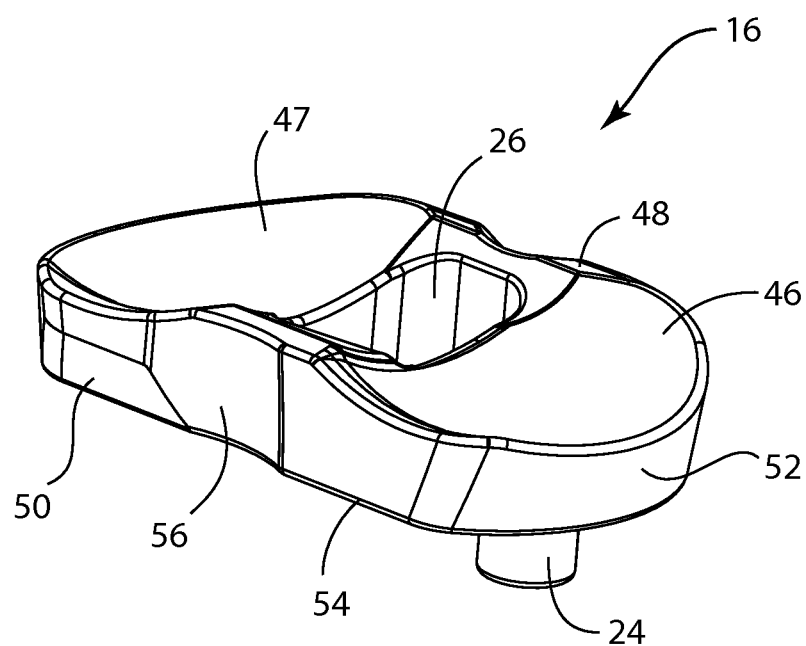
FIG. 8 illustrates a perspective top view of the tibial insert of FIG. 1 with articulating surfaces, a tibial insert notch on the posterior side to allow retention of the posterior cruciate ligament (PCL), a boss and a tibial insert channel.
Figure 8:
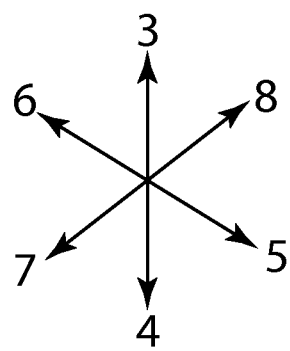

Referring to FIG. 8, the tibial insert 16 comprises a tibial baseplate facing side 54, a femoral implant facing side 55, a tibial insert periphery 52 extending around the tibial insert 16 and a tibial insert channel 26. The tibial insert channel 26 may be arc-like shaped and may be generally centrally located extending from the femoral implant facing side 55 to the tibial baseplate facing side 54 and is shaped to slidably fit over the cam post 19. The tibial channel 26 is large enough and shaped to allow some arc-like rotation of the tibial insert 16 after being positioned over the cam post 19. The femoral implant facing side 55 may comprise a first articulating surface 46 and a second articulating surface 47 positioned opposite the tibial insert channel 26. The first articulating surface 46 may be positioned substantially medial to the insert channel 26 and extend from the insert channel 26 to the tibial insert periphery 52. The second articulating surface 47 may be positioned substantially lateral to the insert channel 26 and extend to the tibial insert periphery 52. The articulating surfaces 46, 47 are shaped and curved to align with the femoral implant 12 for when the prosthetic knee 10 is implanted in the patient.

Figure 9:
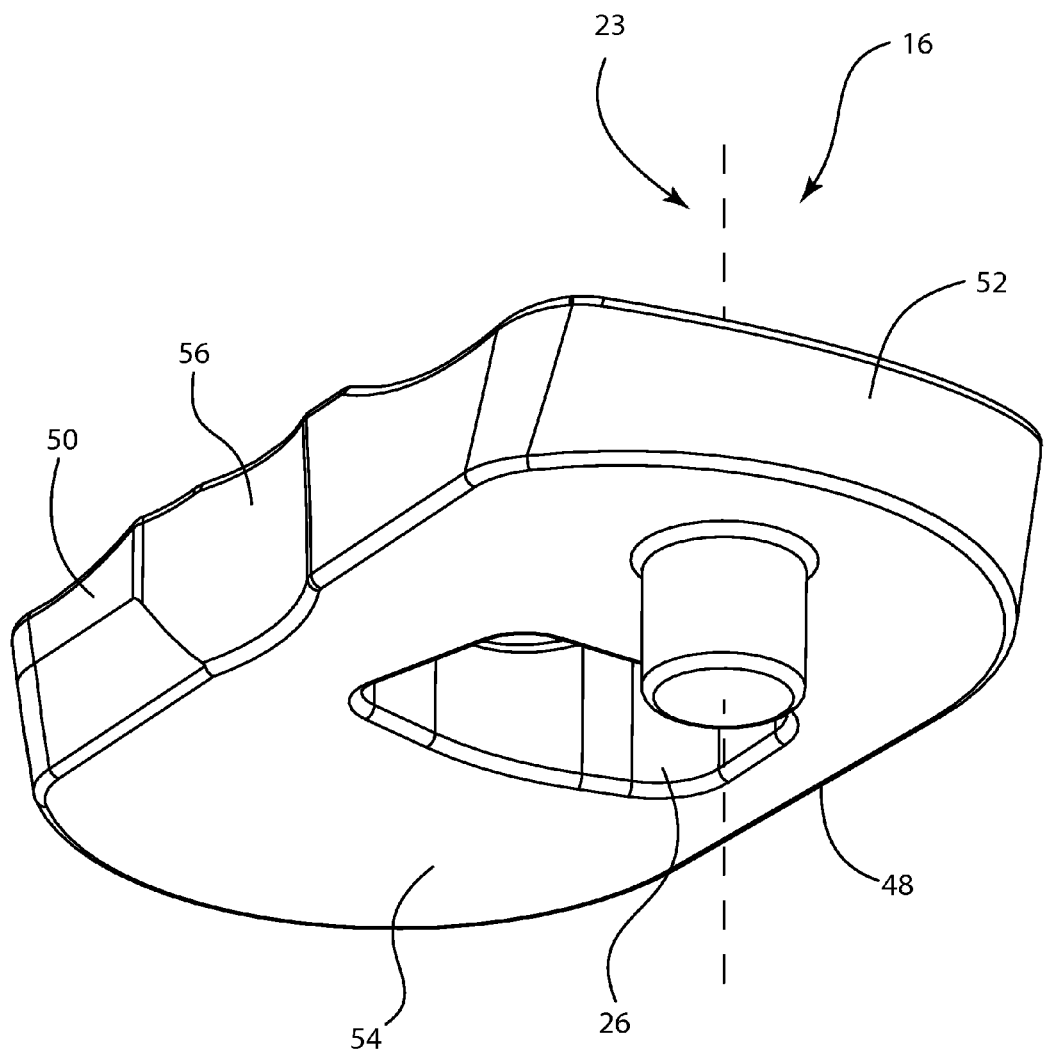
FIG. 9 illustrates a perspective bottom view of the tibial insert of FIG. 8 with the tibial insert channel, the boss, the tibial insert notch, a baseplate facing surface and an axis of rotation generally in the center of the boss.
Figure 9:
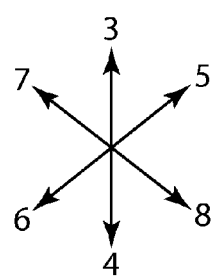

Referring to FIG. 9, the tibial baseplate facing side 54 may be substantially flat with the exception of a boss 24 extending inferiorly, positioned toward the medial side of the tibial baseplate 14 but apart from the tibial insert periphery 52. The flat tibial baseplate facing side 54 may align with the flat superior surface 28 of the tibial baseplate 14 and the boss 24 being is positioned within the cavity 22 of the tibial baseplate 14. The cavity 22 provides a rotation axis of the tibial insert 16 allowing for some amount of pivot rotation along this rotation axis which allows the tibial insert to perform an arc-like rotation in relation to the tibial insert channel 26 and the cam post 19. The rotation of the tibial insert 16 is constrained by the tibial insert channel 26 positioned over the cam post 19.

The tibial insert 16 can be comprised of many biocompatible materials. Polymers may be preferred but metals and ceramics may also be used.

Figure 10:
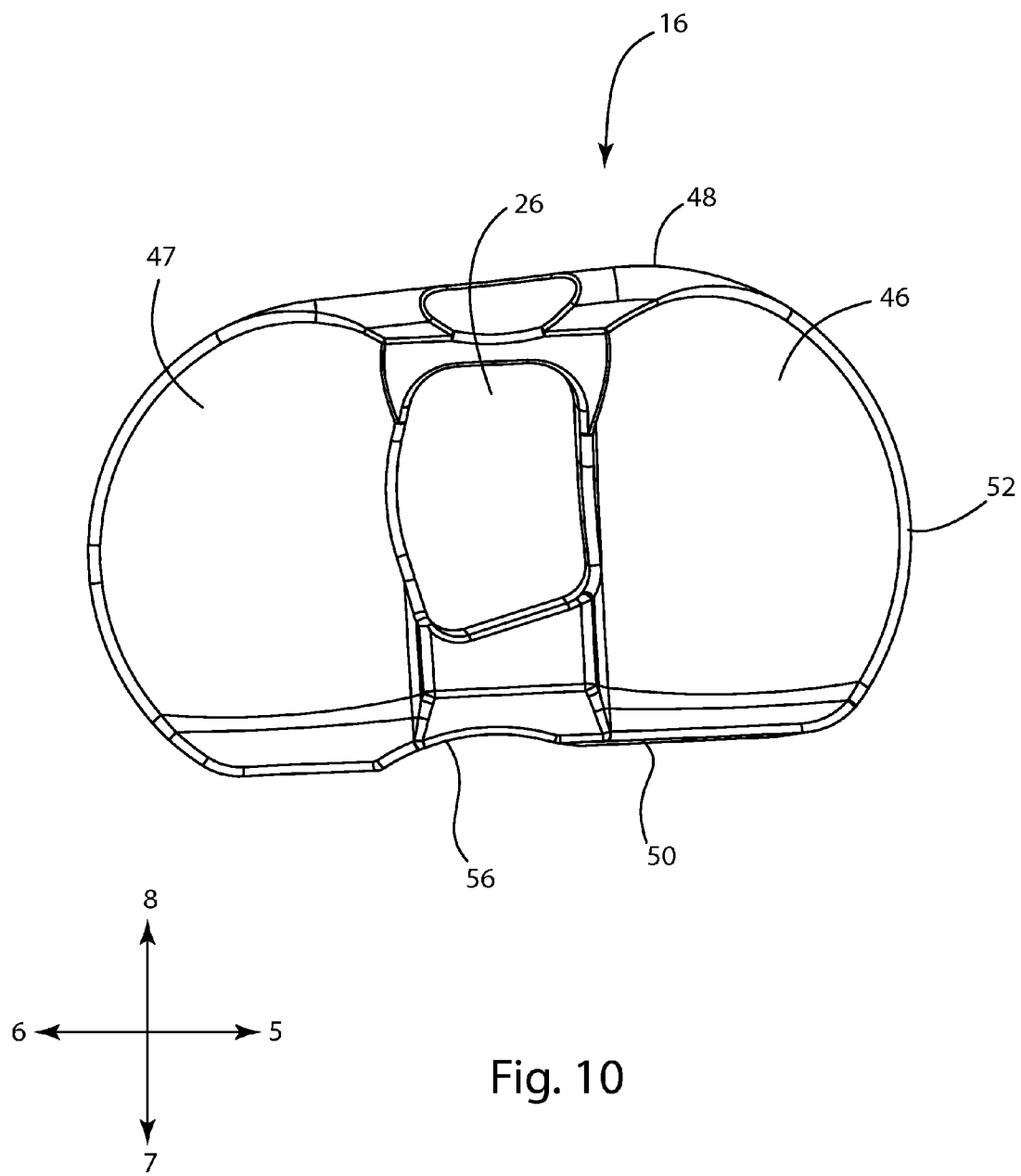
FIG. 10 illustrates a top view of the tibial insert of FIG. 8 with the articulating surfaces, the notch and the channel.

Referring to FIG. 10, a tibial insert notch 56 may be positioned along the tibial insert periphery 52 toward the posterior end of the tibial insert 16. The tibial insert notch 56 may be aligned with the tibial baseplate notch 40 and may allow room for retention of the posterior cruciate ligament (PCL) or another ligament behind the tibial baseplate 14 and the tibial insert 16.

Figure 11:
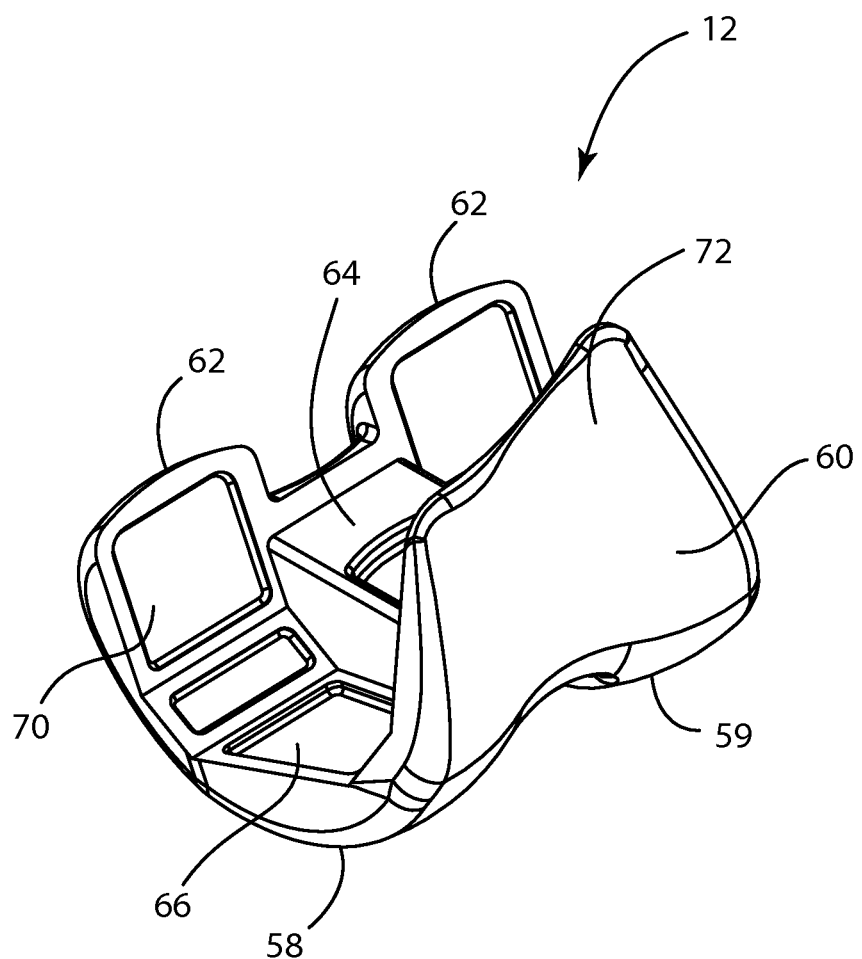
FIG. 11 illustrates a perspective front view of the femoral implant of FIG. 1 with condyles for articulation with the tibial baseplate, a cam feature for interaction with the cam post and a trochlear notch.
Figure 11:
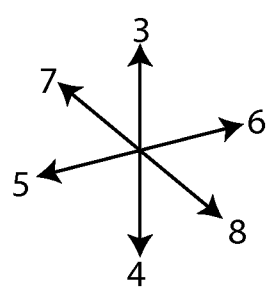

Referring to FIG. 11, the femoral implant 12 has a bone-facing side 70, a trochlear groove 72 on an anterior end 60 end of the femoral implant 12, and a cam feature 64. The trochlear groove 72 adjoins a first condyle 58 and a second condyle 59 extending posteriorly to a posterior end 62 of the femoral implant 12. The cam feature also adjoins the first and second condyles 58, 59. The first condyle and second condyles 58, 59 may curve cephalically, to match the contours of a natural distal end of a femur and are shaped to align with the first articulating surface 46 and the second articulating surface 47 of the tibial insert 16 respectively. The radius of curvature of the condyles 58, 59 may relatively match the same curvature of the articulating surfaces 46, 47 of the tibial insert 16. The condyles 58, 59 may be polished to minimize wear between the condyles 58, 59 218 and the articulating surfaces 46, 47 of the tibial insert 16. If the tibial insert 16 is also made of metal, including those metals named herein, it may also be polished to minimize wear.

The bone-facing side 72 may have a bone-facing surface 66 which may comprise a porous material to encourage bone in-growth. A gap 68 between the condyles 58, 59 is generally a fixed height, but the condyles 58, 59 may be of various widths, sizes and curvatures depending on the specific anatomy of the patient or tibial insert 16. The surface curvature of the condyles 58, 59 may also vary to match the curvature of the specific tibial insert 16 chosen for the patient's mobility requirements.

Figure 12:
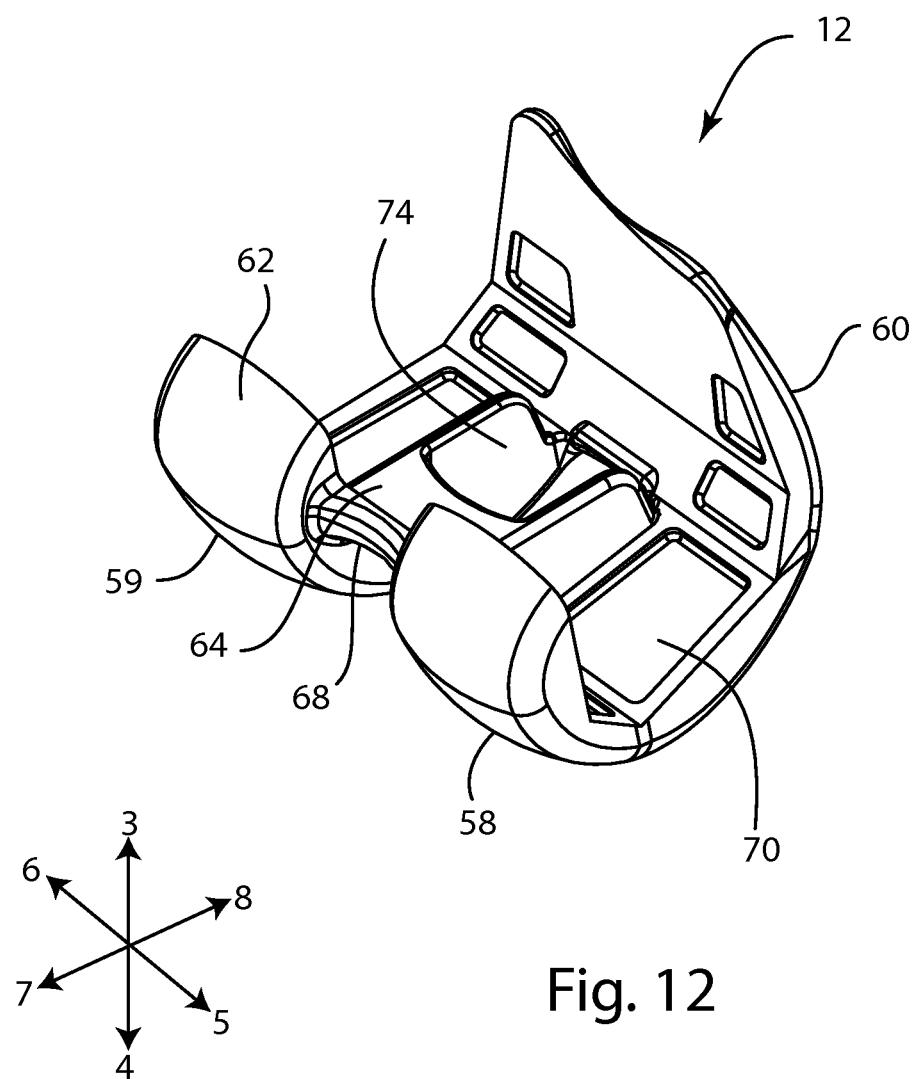
FIG. 12 illustrates perspective back view of the femoral implant of FIG. 11 with a femoral implant opening for engagement with the cam post, a condyle gap between the condyles and condyles.

Referring to FIG. 12, the femoral implant 12 may further comprise an opening 74 shaped and positioned to receive the cam post 19. The cam post 19 slidably inserts into the opening 74 and a posterior side of the cam post 19 engages the cam feature 64 on an anterior side of the cam feature 64 during knee flexion.

Figure 13:
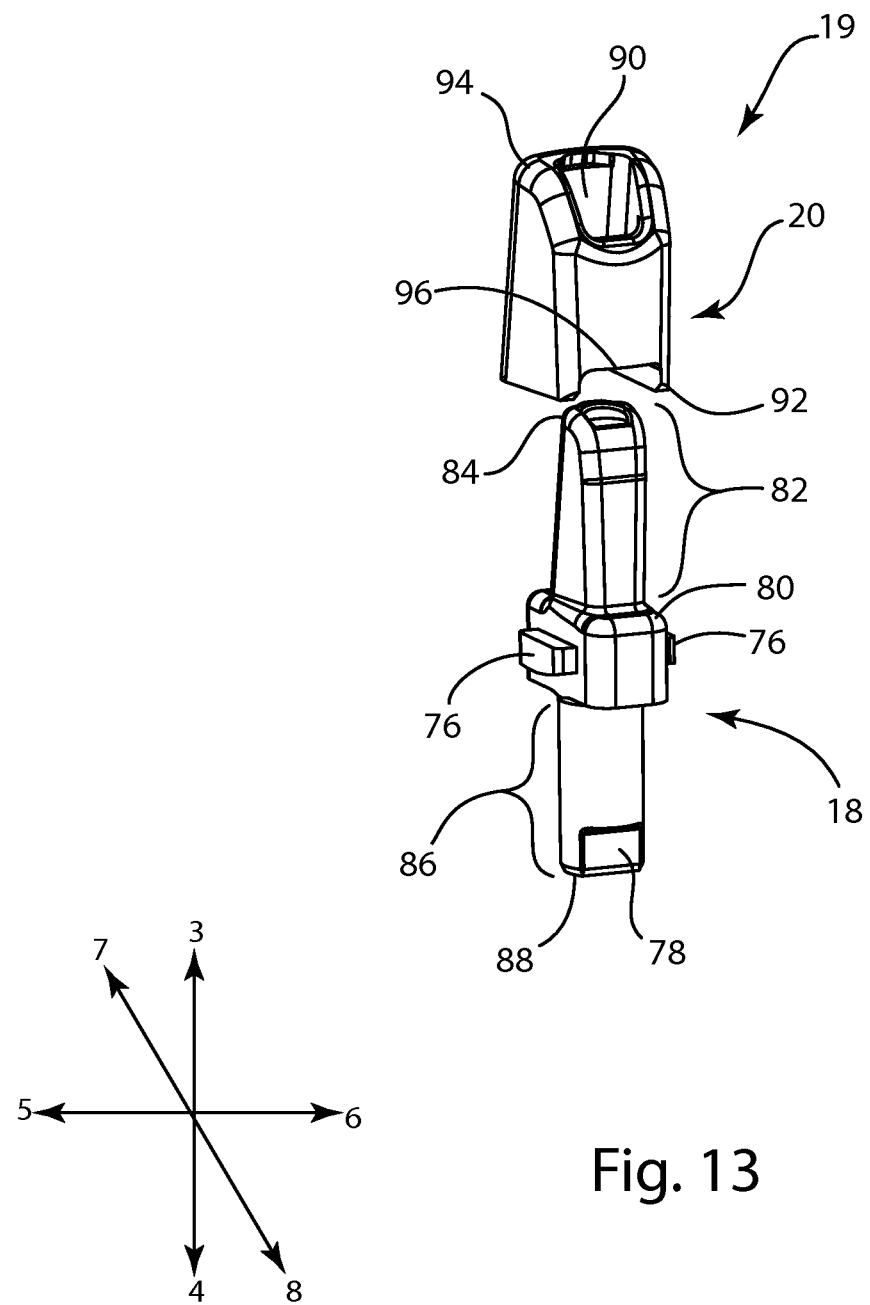
FIG. 13 illustrates an exploded perspective view of the cam post of FIG. 2 with a cam post core and an outer sleeve.

Referring to FIG. 13, the cam post 19 has the cam post core 18 and the outer sleeve 20. The cam post core 18 has an inferior end 88, a superior end 84, a superior portion 82, an inferior portion 86 and an intermediate portion 80 between the superior and inferior portions 82, 86. The intermediate portion 80 may of greater width than the inferior and superior portions 82, 86, and may comprise wings 76 extending laterally and medially and are positioned as a stop to engage the outer sleeve 20. Toward the inferior 88 the cam post core may have a Morse taper or similar taper or pin which engages in the tibial baseplate hole 30 and a core notch 78 which may act like a key fit. The intermediate portion may also vary in height (superiorly to inferiorly) depending on variations of the patients anatomy.

Figure 14:
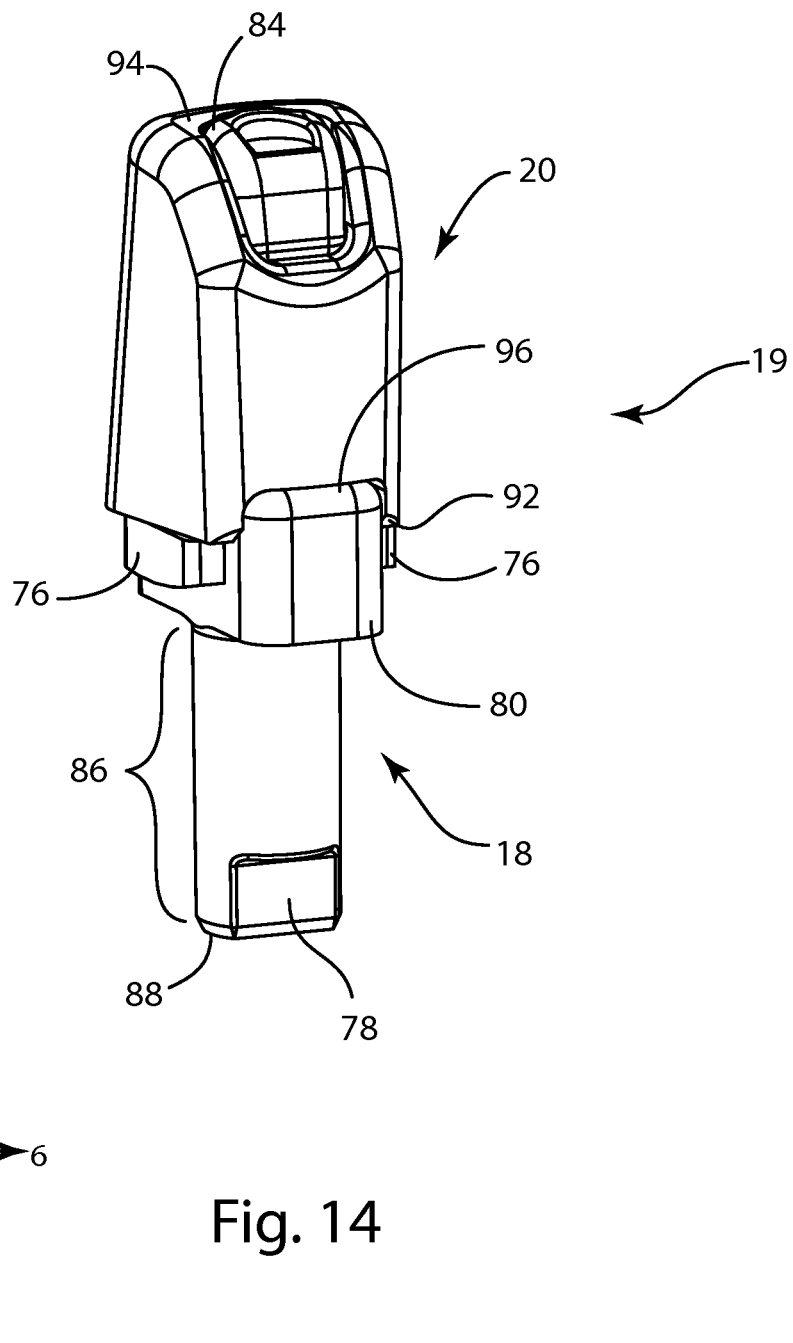
FIG. 14 illustrates the cam post of FIG. 13 with the outer sleeve at least partially encircling the cam post core.

Referring to FIGS. 13 and 14, the superior portion 82 is shaped to slidably receive the outer sleeve 20. The outer sleeve 20 has a sleeve channel 90, a superior end 94 and an inferior end 92. The sleeve channel 90 is shaped to slide over the superior portion 82 at least partially surrounding the superior portion 82. The outer sleeve is positioned around the superior portion 82 and slides onto the superior portion 82 until the sleeve inferior end 92 engages the wings 76 of the intermediate portion 80 of the cam post 19. The outer sleeve 20 may comprise a sleeve notch 96 toward the inferior end 92 of the outer sleeve 20 which may communicate with the intermediate portion 80 and receive a portion of the intermediate portion 80 within the sleeve notch 96, providing greater stability and fixation of the cam post core 18 to the outer sleeve 20. The sleeve notch 96 may also provide rotational stops so the sleeve is unable to rotate when snapped into engagement with the cam post core 18. The outer sleeve 20 may be secured to the cam post core 18 through snap fit features. After the outer sleeve 20 is positioned around the superior portion 82 of the cam post core 82 the cam post core superior end 84 and the outer sleeve superior end 94 may be flush.

The cam post core 18 and other post elements disclosed herein may be made of cobalt-chrome or its alloys, titanium or its alloys, stainless steel or any other biocompatible metal, ceramic or polymer. The outer sleeve 20 and other sleeve elements disclosed herein may be preferably made of polymer; however, it may also be comprised of many other biocompatible materials including ceramics and metals. In addition the cam post core 18 and the sleeve 20 may be one piece instead of two pieces.

Referring back to FIG. 3, the tibial baseplate 14 is secured to the resected tibia 2. The cam post 19 may be secured to the tibial baseplate 14 using a Morse taper or similar taper or pin feature (the core notch 78 of the cam post core 18). The tibial insert 16 is positioned over the cam post 19 and the boss 24 of the tibial insert 26 is positioned within the cavity 22 of the tibial baseplate providing an axis of rotation 23. The tibial insert channel 26 may contain a metal band lining the channel 26. The sleeve 20 of the cam post 19 may be polyethylene and may extend from the sleeve superior end 94 to the tibial baseplate 14 when the cam post 19 is correctly positioned in the baseplate 14. This feature of the metal band and extension of the polyethylene sleeve 20 may minimize stresses on the tibial insert 16 when it contacts the cam post 19 and stops.

The femoral implant 12 is secured to the resected femur 1. The cam post is then positioned within the opening 74 of the femoral implant 12 engaging the cam feature 64 during knee flexion. The cam feature 64 provides rollback and femoral external rotation during knee flexion. The cam post 19 after engaging the cam feature 64 allows two fully guided rotational axes and provides anterior and posterior stabilization features. The cam post 19 engages the cam feature 64 resisting posterior tibial translation. The cam post 19 also engages the tibial insert channel 26 to restrict anterior displacement of the tibial insert and the tibia as well.

One fully guided rotational axis is between the femoral implant 12 and the tibial insert 16 by engagement of the condyles 58, 59 with the articulating surfaces 46, 47. A second fully guided rotational axis is between the tibial insert 16 and the tibial baseplate 14 by aligning the tibial baseplate facing side 54 with the flat superior surface 28 of the tibial baseplate 14. The second rotational axis is accomplished by the positioning of the boss 26 within the cavity. The first and second rotational axes closely match the motion of the natural knee and are suitable for hard-on-hard bearing contact surfaces, such as the use of cobalt-chrome, ceramic, composite or other hard materials for the femoral implant 12, tibial insert 16 and tibial baseplate 14, which may lead to longer durability of the prosthetic knee. The potential advantage of using exclusively hard materials is that polyethylene debris can be eliminated and wear particle generation can be reduced, reducing the chance of osteolysis and implant loosening. However, to be able to use exclusively hard materials requires a fully guided motion conforming mobile bearing design—meaning a design in which relative motion between any two parts occurs along only one path.

Cobalt-chrome and its alloys are not the only hard-on-hard materials that may be used, other examples include, but are not limited to, stainless-steel, titanium and its alloys, titanium carbide, titanium nitride, ion-implantation of titanium, diffusion hardened metals, diamond like coatings, diamond-like carbon, zirconium nitride, niobium, oxinium or oxidized zirconium, ceramics such as alumina and zirconia, and many other biocompatible materials and coatings.

Another advantage of the features recited herein is that this design provides knee motion during flexure closer to the natural knee. Two other benefits of these novel features is that (1) the cam post 19 can provide both anterior and posterior rotational stops for the tibial insert 16, and (2) the cam post 19 can independently provide anterior and posterior translation stops for the femoral implant 12. These benefits of the design contribute to the overall stability of the prosthetic knee, eliminate the risk of bearing spin out, and limit anterior tibial translation which is provided by the anterior cruciate ligament in a natural knee.

In alternative embodiments, the various components shown and described herein may have different sizes, configurations (such as size of the keel, shape and size of the cam post, the width of tibial insert, and the like) material properties, and other variations to adapt them to variations in patient anatomy. If desired, multiple versions of each of the femoral implant, tibial baseplate, and tibial insert components may be provided together in a single kit to enable a surgeon to interoperatively select the best set of components for a patient.

Figure 15:
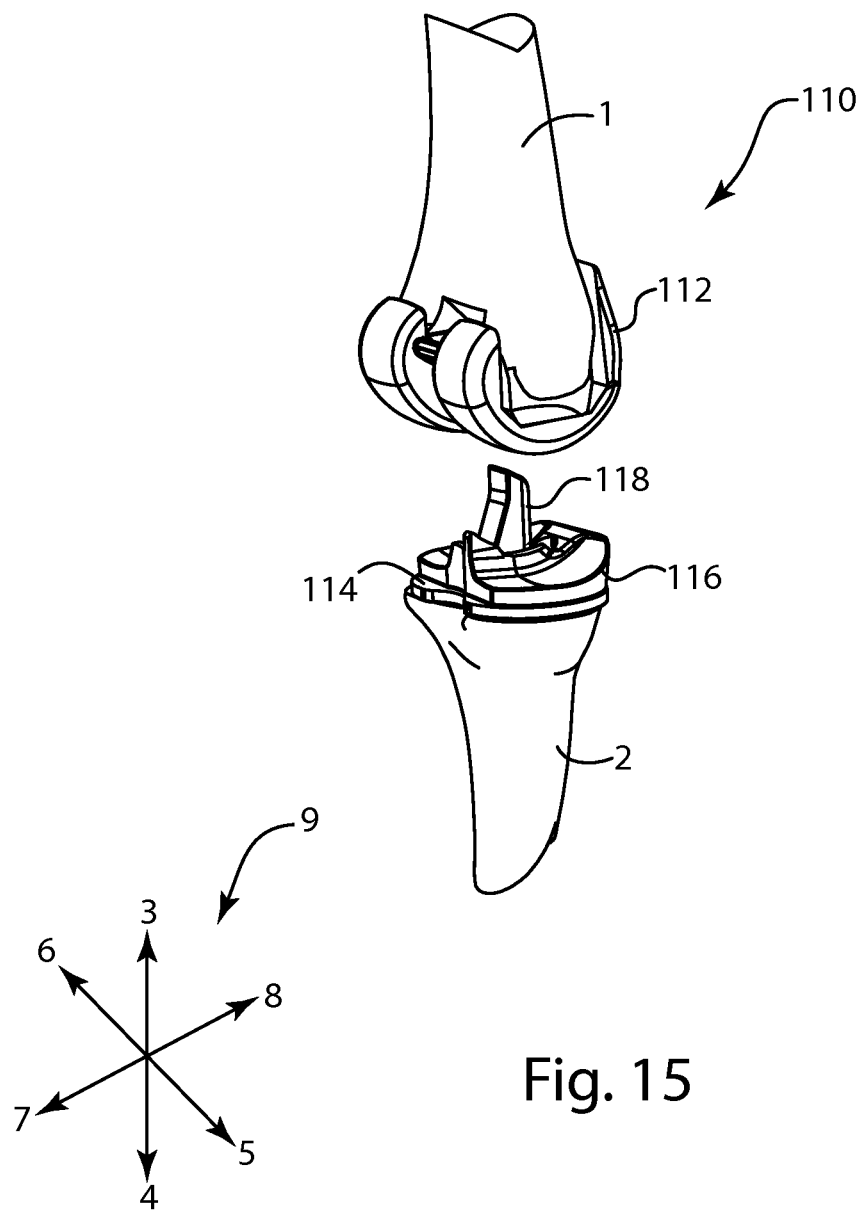
FIG. 15 illustrates a perspective view of an alternate embodiment of the prosthesis with a femur, a tibia, femoral implant, a cam post a tibial insert and a tibial baseplate.

Referring to FIG. 15, an alternate embodiment of a prosthetic knee 110 includes a femoral implant 112, a tibial baseplate 114, a tibial insert 116 and a cam post 118. The interaction between each of the components is similar to the previous embodiment.

Figure 16:
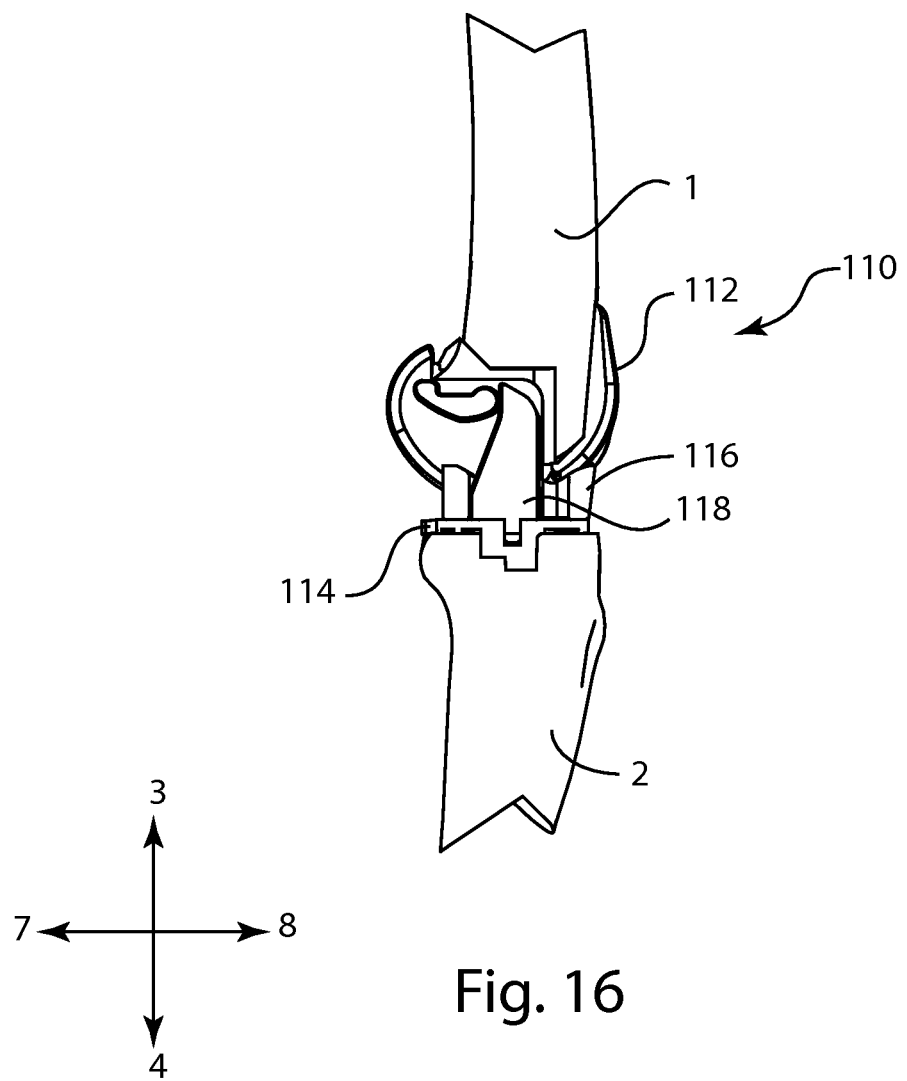
FIG. 16 illustrates a cross sectional side view of the prosthesis of FIG. 15 with the femoral implant the cam post, the tibial insert and the tibial baseplate.

Referring to FIG. 16, similar to the previous embodiment the femoral implant 112 engages the tibial insert 116 and the cam post 118 may engage a cam feature 120 during flexion of the knee providing anterior and posterior translational stops for the femoral implant. The cam 118 post is fixed to the tibial baseplate 114 and passes through a tibial insert channel 130 (better depicted in FIGS. 19 and 20). The cam post 118 provides anterior and posterior rotational stops for the tibial insert 116.

Figure 17:
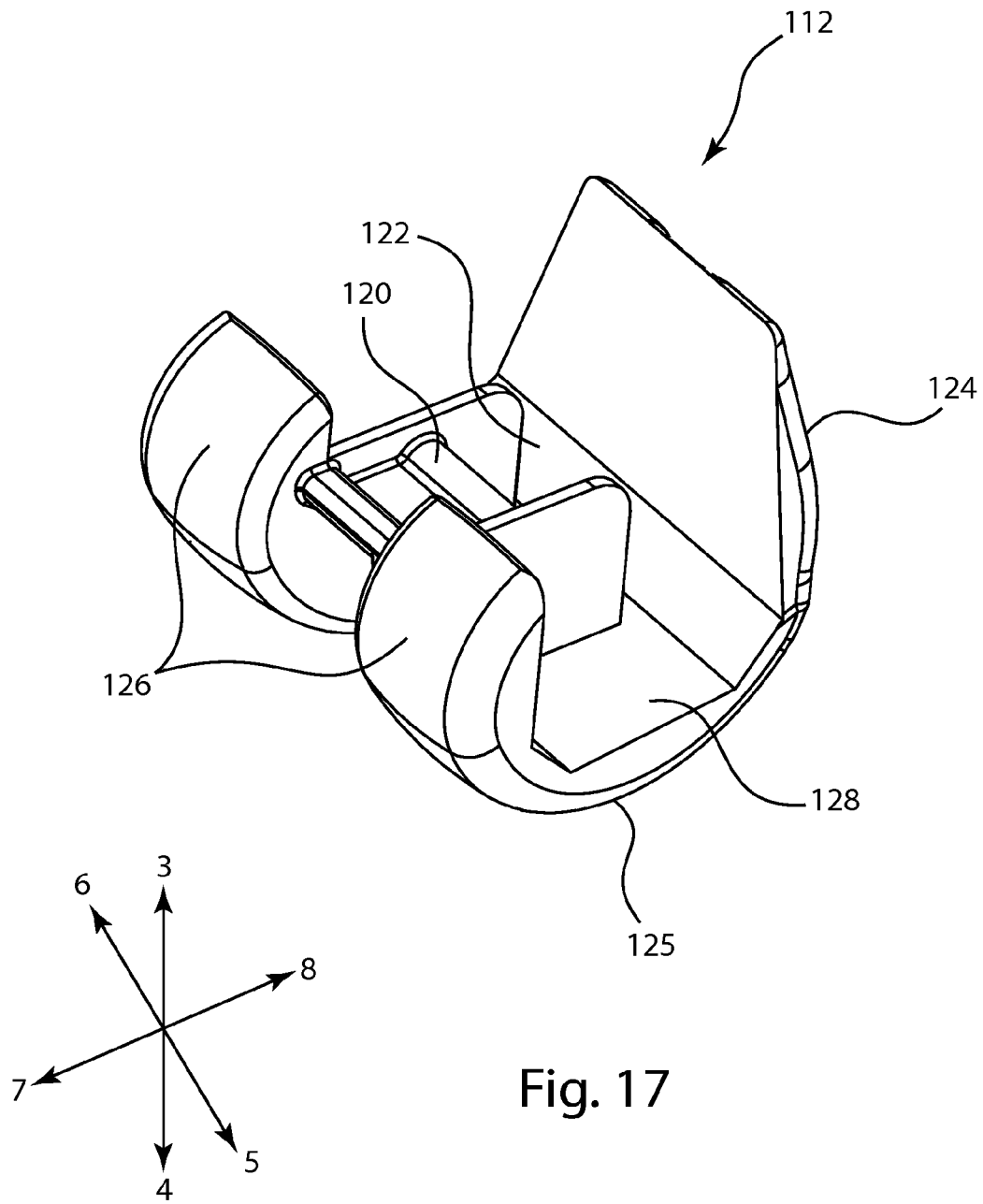
FIG. 17 illustrates a perspective back view of the femoral implant of FIG. 15 with a cam feature, condyles, and a femoral opening.

Referring to FIG. 17, the femoral implant 112 includes condyles 125 which interact with and are highly conforming with the tibial insert 116. The femoral implant also includes a bone facing side 128 that is configured to engage a resected femur. Between an anterior end 124 and a posterior end 126 lies a femoral implant opening 122 shaped to receive the cam post 118 and immediately posterior to the opening 122 is a cam feature 120 which is positioned and shaped to engage the cam post 118 during flexion of the prosthetic knee 110. The cam feature 120 provides rollback and femoral external rotation during knee flexion.

Figure 18:
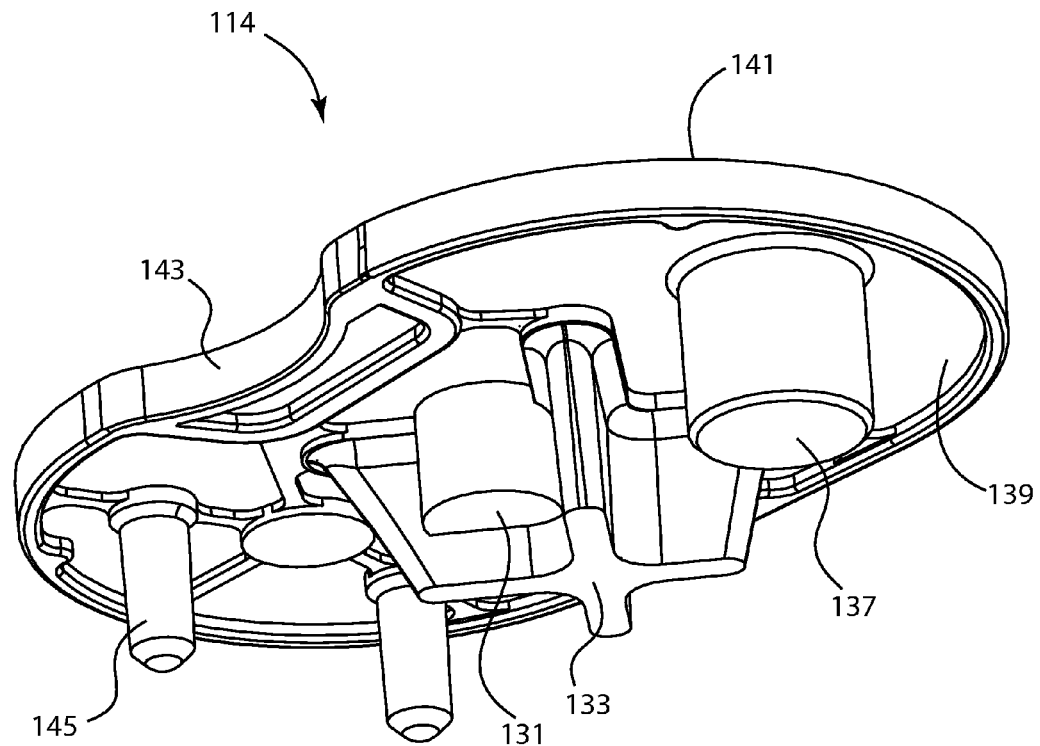
FIG. 18 illustrates a perspective bottom view of the tibial baseplate of FIG. 15 with a keel (smaller than the keels of FIGS. 4-7), at least one peg, a cavity to receive a boss of the tibial insert and tibial facing side and a notch on the posterior side for retention of the PCL.
Figure 18:
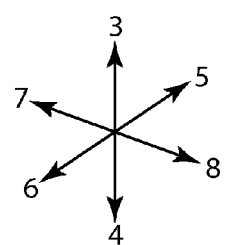

Referring to FIG. 18, the tibial baseplate 114 is similarly shaped to the previous embodiment's baseplate 14. However, a keel 133 may be shorter. The tibial baseplate 114 may comprise the same elements of the previous embodiment and they may carry out the same functions of the previous embodiment as well. The parts of the tibial baseplate which my mirror the previous embodiment include a tibial baseplate hole 131 to engage the cam post 18, a tibial baseplate cavity 137 to engage a boss 132 (depicted in FIG. 19), a tibia facing surface 137 configured to engage the resected tibia 2. The features may also include at least one peg 145 extending from the tibia facing surface 137 to engage the tibia 2. A tibial baseplate superior surface 141 is generally flat allowing for interaction with the tibial insert 116 similar to the previous embodiment. The tibial baseplate may also further comprise the tibial baseplate notch 143 which may allow room for retention of the posterior cruciate ligament (PCL) or another ligament behind the tibial baseplate 114 and the tibial insert 116.

Figure 19:
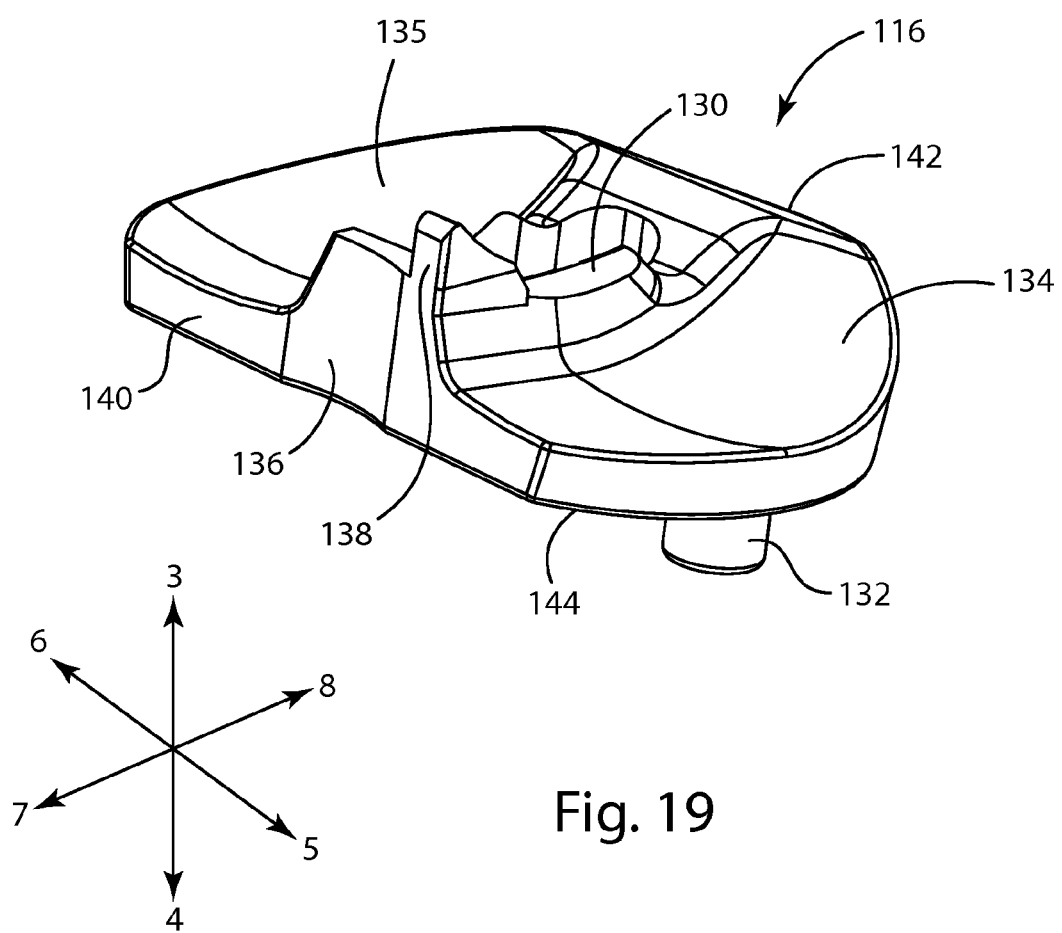
FIG. 19 illustrates a perspective top view of the tibial insert of FIG. 15 with articulating surfaces to interact with the condyles of the femoral implant of FIG. 17, a boss to interact with the cavity of the tibial baseplate of FIG. 18, a medial peak, a tibial insert channel for passage of the cam post, and a notch on the posterior side of the tibial insert for retention of the PCL.
Figure 20:
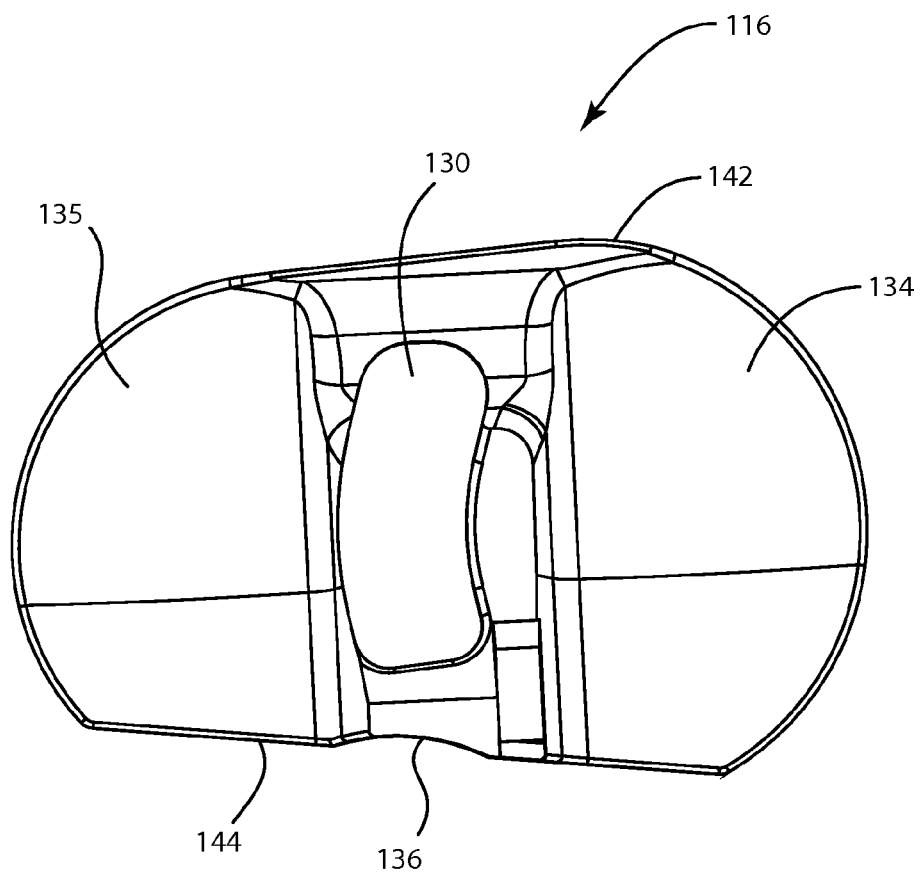
FIG. 20 illustrates a top view of the tibial insert of FIG. 19 with a channel, a notch and articulating surfaces.
Figure 20:
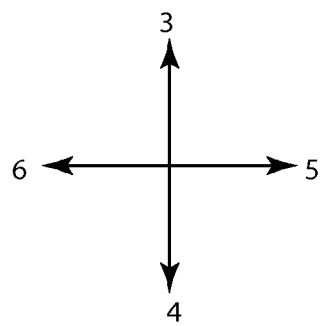

Referring to FIGS. 19 and 20, the tibial insert 116 may comprise many of the same elements with the same function and design as the previous embodiment. However, an anterior end 142 may have a greater width than a posterior end 140 of the tibial insert 116. In addition a peak 138 may extend superiorly and may be positioned toward the posterior end 140 of the tibial insert 116 to interact between, and are highly conforming with, the condyles 125 of the femoral implant 112. The other characteristics of the tibial insert 116 include a medial and a lateral articulating surfaces 134, 135 sculpted and curved to align with the condyles 125 of the femoral implant, as well as the tibial insert channel 130 which may be somewhat arc shaped (Refer to FIG. 17), which is large enough to slidably receive the cam post 118 and allows for anterior posterior rotation along the arced channel 130. Furthermore the tibial insert 116 includes the tibial insert baseplate facing surface 144 which is generally flat configured to align with the generally flat tibial baseplate superior surface 144, and the boss 132 shaped to align and be received within the cavity 137 to provide a rotational axis for the anterior posterior rotation of the tibial insert 116. The tibial insert 116 also includes the tibial insert notch 136 which may allow room for retention of the posterior cruciate ligament (PCL) or another ligament behind the tibial baseplate 114 and the tibial insert 116.

Figure 21:
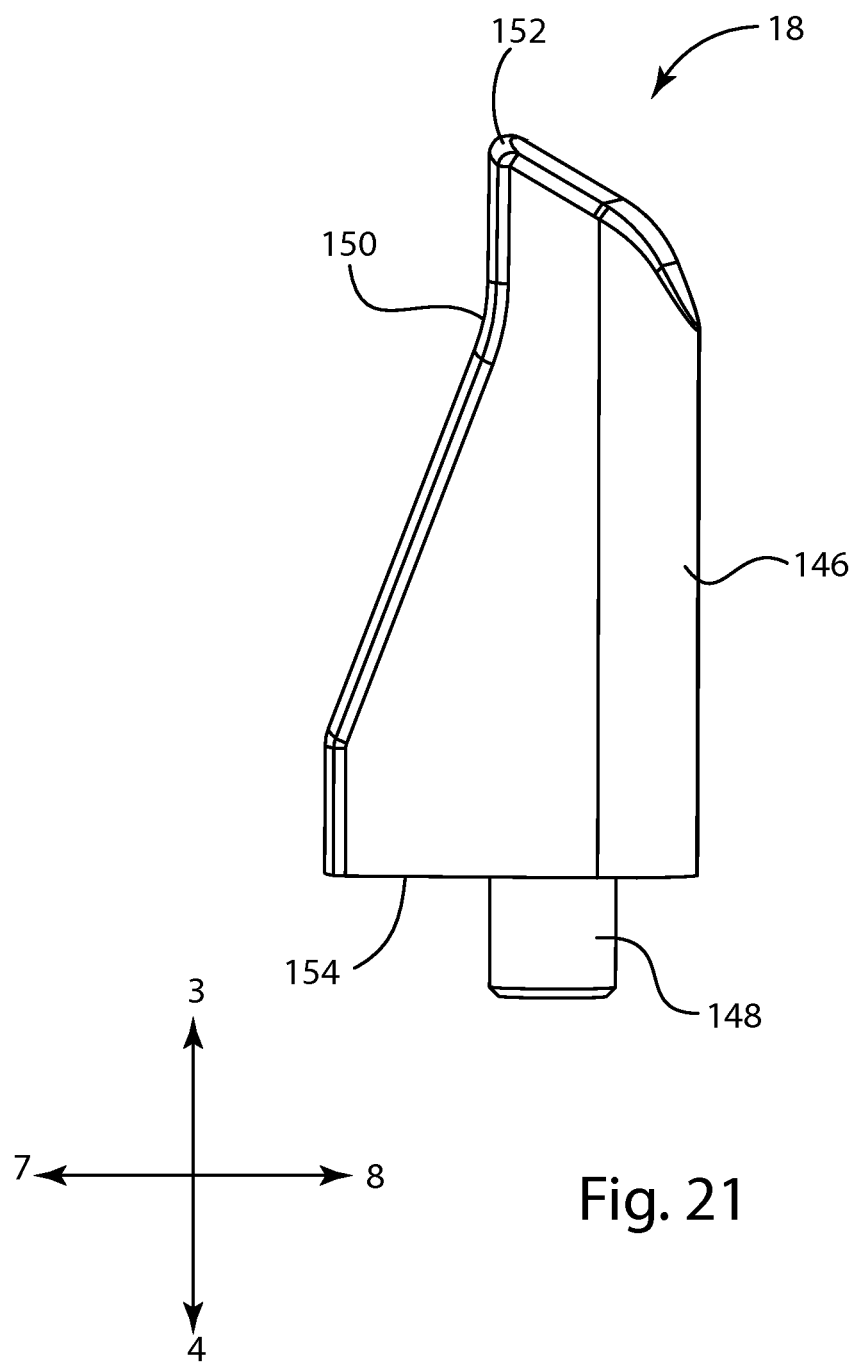
FIG. 21 illustrates a side view of the cam post of FIG. 15 with a cam post body superior end and an inferior end with a groove between the superior and inferior ends and a cam post boss extending inferiorly from the inferior end of the cam post.
Figure 22:
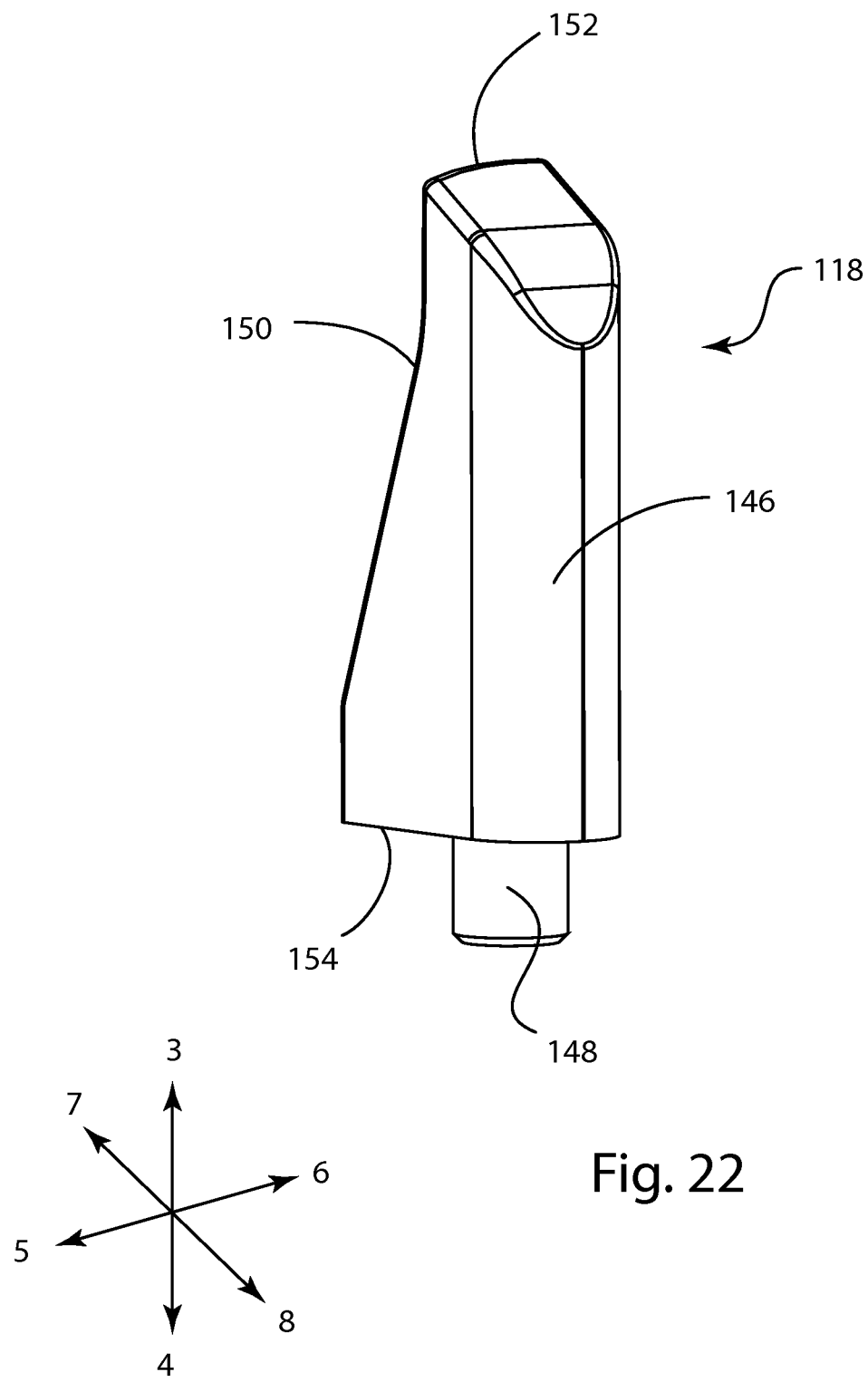
FIG. 22 illustrates a perspective front view of the cam post of FIG. 21.

Referring to FIGS. 21 and 22, the cam post 118 includes a cam post body 146 with a wider inferior end 154 than a superior end 152 and a cam post boss 148 extending inferior shaped to engage the tibial baseplate hole 131. The cam post 118 is fixed to the tibial baseplate 114 through the interaction between the tibial baseplate hole 131 and the cam post boss 148.

The cam post 118 decreases in width from the inferior end 154 to the superior end 152. Between the superior end 152 and the inferior end 154 is a groove 150 shaped to engage the cam feature 120 of the femoral implant 112 during flexion of the prosthetic knee 110.

The interaction each of the components is generally similar to the previous embodiment with differences in structure only (refer to FIG. 13). The features recited herein are that this design provides knee motion during flexure closer to the natural knee. Benefits of these novel features include the same features as previously recited which are (1) the cam post 118 can provide both anterior and posterior rotational stops for the tibial insert 116, and (2) the cam post 118 can independently provide anterior and posterior translation stops for the femoral implant 112. These benefits of the design contribute to the overall stability of the prosthetic knee 110.

Figure 23:
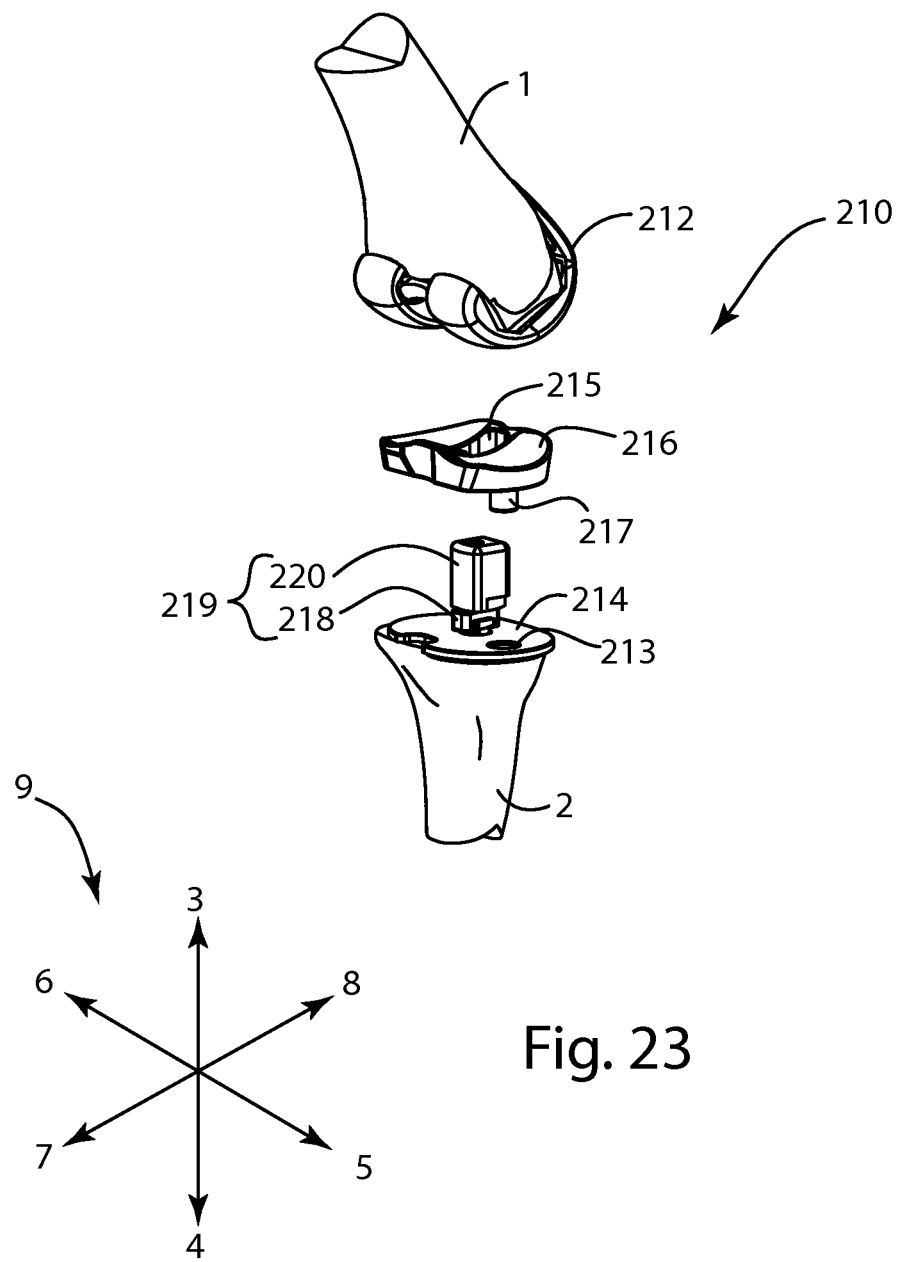
FIG. 23 illustrates an exploded perspective back view of an alternate embodiment of the prosthesis of FIG. 1 with a femur, a tibia, femoral implant, a cam post, a tibial insert and a tibial baseplate.
Figure 24:
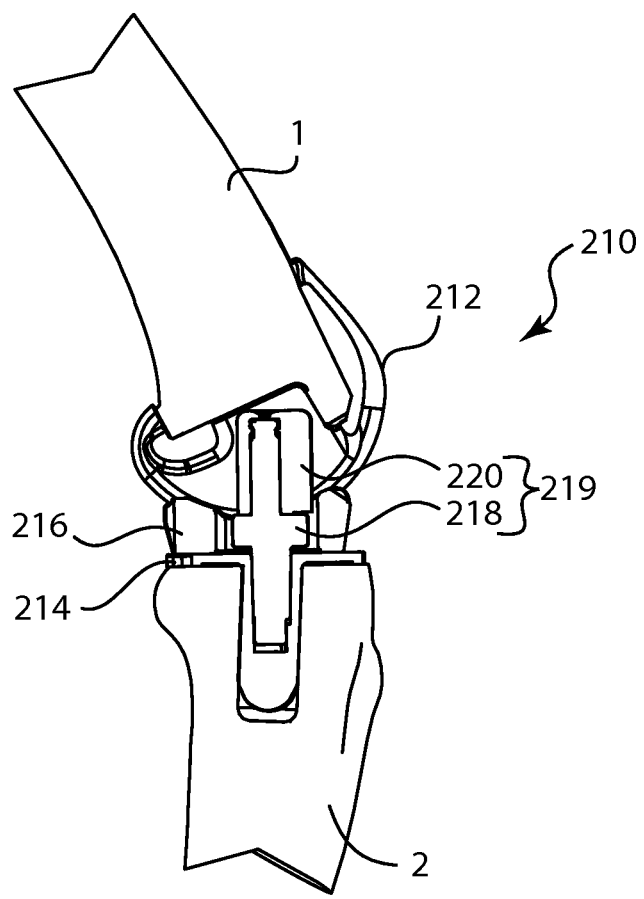
FIG. 24 illustrates a cross sectional side view of the prosthesis of FIG. 23 with a femoral implant, a cam post, a tibial insert and a tibial baseplate.
Figure 24:
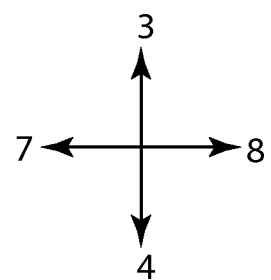

Referring to FIGS. 23 and 24, another alternate embodiment of a prosthetic knee 210 includes the same or similar components of the previous embodiments with a femoral implant 212, a tibial baseplate 214, a tibial insert 216 and a cam post 219 comprising a cam post core 218 and a sleeve 220. This specific embodiment is intended to prevent varus/valgus displacement and may be more suitable for those patients who have insufficient, lax or absent medial or lateral stabilizing ligaments. The tibial insert has a tibial insert channel 215 (similar to those channels 26 and 130 in the two previous embodiments) and a boss 217 (similar to those bosses 24 and 132 of the previous embodiments). The tibial baseplate 214 has a cavity toward the medial side 213

Figure 25:
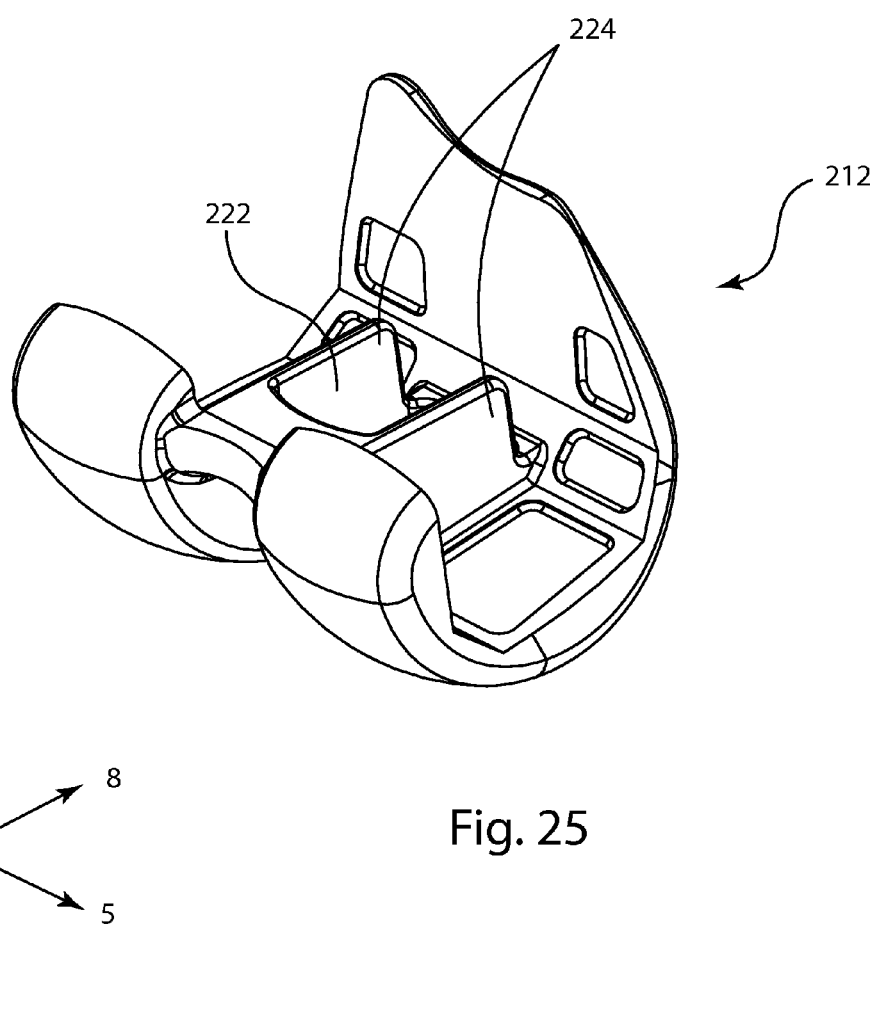
FIG. 25 illustrates a perspective back view of a femoral implant with a femoral opening engaging the cam post and opening walls for stabilization of the cam post and the prosthesis.

The components are substantially similar to the previous embodiments. The tibial insert has a tibial insert channel 215 (similar to those channels 26 and 130 in the two previous embodiments) and a boss 217 (similar to those bosses 24 and 132 of the previous embodiments). However, referring to FIG. 25, the femoral implant 212 which has a femoral opening 222 may also comprise opening walls 224 which engage the cam post sleeve 220 of the cam post 219 preventing varus/valgus distraction and provide greater medial/lateral stabilization (refer to FIG. 23).

Figure 26:
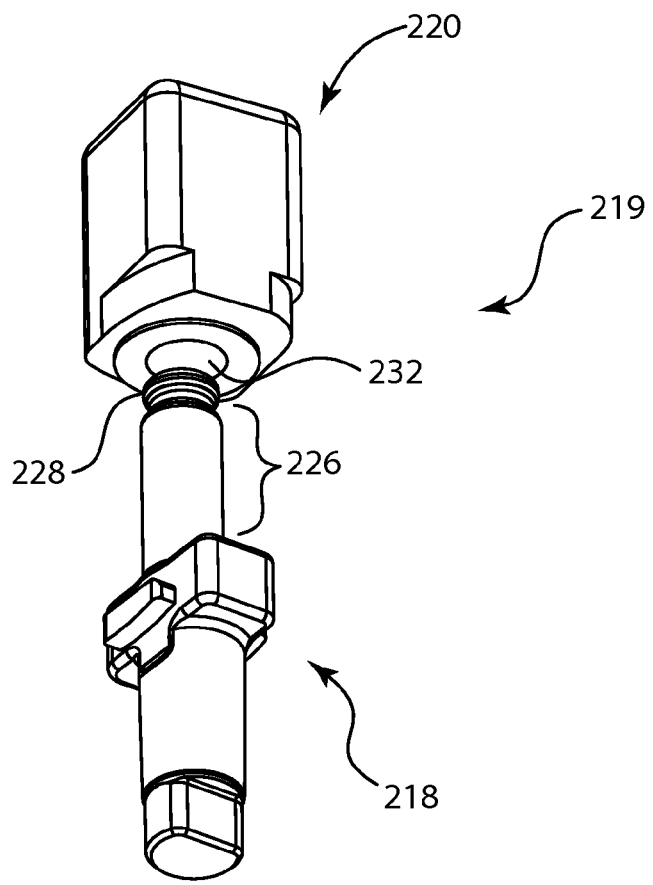
FIG. 26 illustrates a perspective view of the cam post of FIG. 23 with a cam post core with a snap feature for engaging a cam post sleeve.
Figure 26:
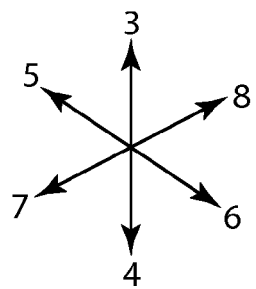

Referring to FIG. 26, the cam post core 218 comprises most of the same features of the cam post core 18 of FIGS. 13 and 14; however, a cam post core superior portion 226 may be substantially circular in cross section with a snap feature 228 on the superior end shaped to snap into engagement with the sleeve 220. The sleeve 220 may be substantially rectangular in cross section, however any shape that would enable engagement with the femoral implant 212 opening walls 224 is sufficient. The sleeve 220 has a cylindrical bore 232 passing longitudinally there through and a taper 230 toward the inferior end of the sleeve 220 to prevent any obstruction of the sleeve with the tibial insert channel 215. The superior portion 226 is at least partially inserted into the sleeve 220 until the two components snap into engagement. The sleeve 220 may rotate around the center axis of cam post core 218 after the sleeve is positioned around the superior portion 226. The cam post core 218 may be polished to minimize wear between the cam post core 218 and the sleeve 220. Internal stops (not shown) may be added to prevent complete rotation of the sleeve around the center axis of the cam post core 218.

Figure 27:
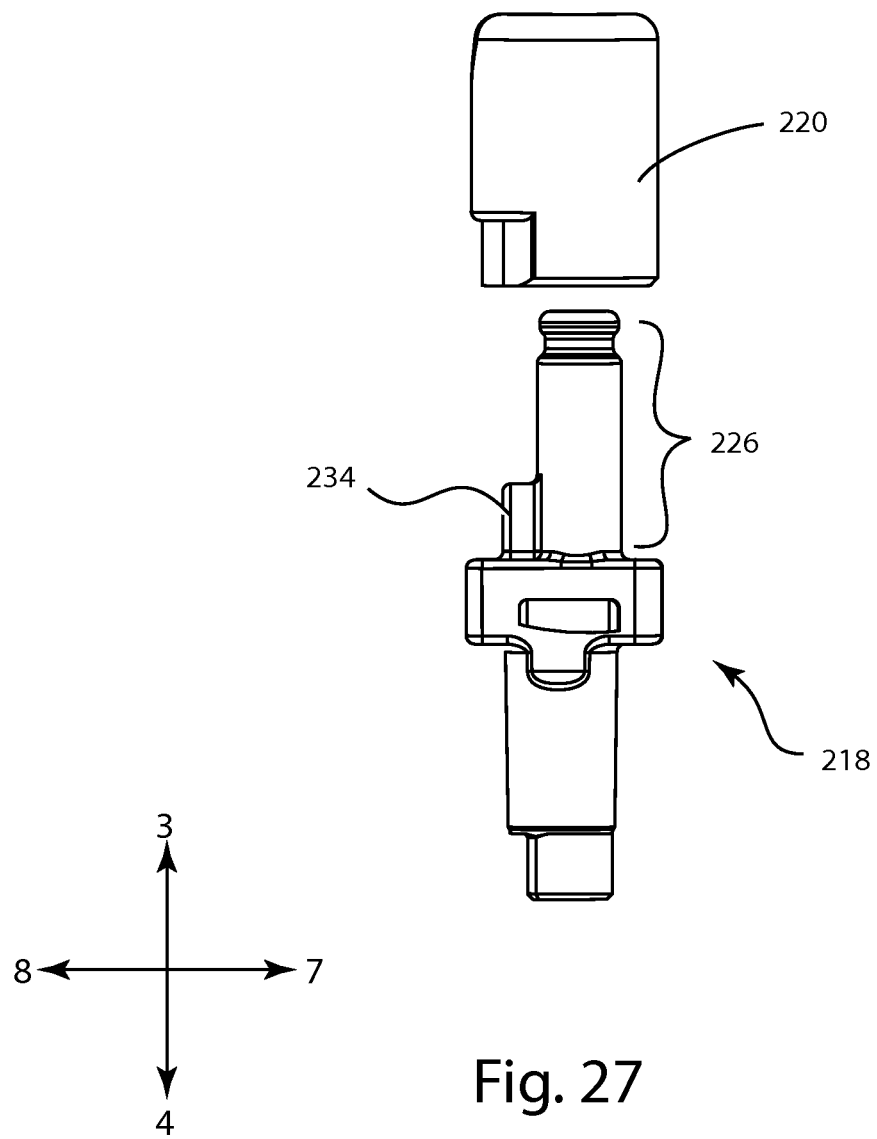
FIG. 27 illustrates a side view of an alternate embodiment of a cam post of FIG. 26 with a cam post sleeve and a cam post core the cam post core having a ridge to prevent movement of the cam post sleeve after it engages the cam post core.
Figure 28:
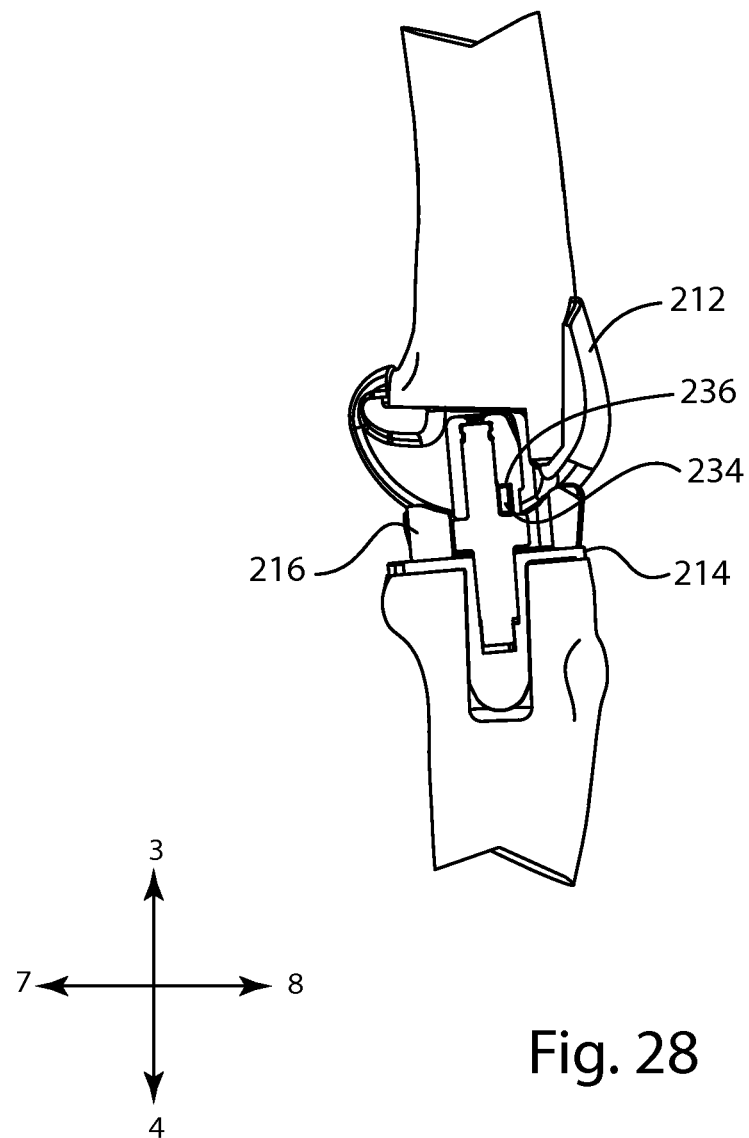
FIG. 28 illustrates slightly different embodiment of the prosthesis of FIG. 23 (the only difference is in the cam post of FIG. 26) showing the cam post of FIG. 27.

Referring to FIGS. 27 and 28, an alternate embodiment of the cam post core 218 may have a ridge 234 which may extend either posteriorly or anteriorly from the superior portion 226 of the cam post core 218. The sleeve 220 may provide a complimentary fit shaped bore 236 that concentrically fits the superior portion 226 with the ridge 234 of the cam post core 218. This ridge 234 prevents any rotational movement of the sleeve 220. Any other means may be used to prevent rotational movement of the sleeve 220 around the cam post core 218. Again, the cam post core 218 and the sleeve 220 may be one piece instead of two pieces.

Figure 29:
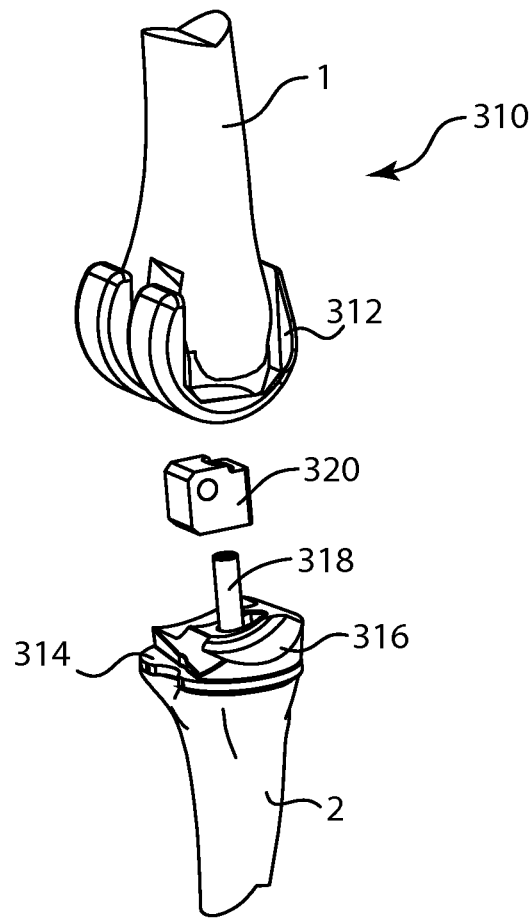
FIG. 29 illustrates an exploded perspective back view of an alternate embodiment of the prosthesis of FIG. 1 with a femur, a tibia, a femoral implant, a tibial insert, a tibial baseplate, a cam post and a hinge block which slides around the cam post.
Figure 29:
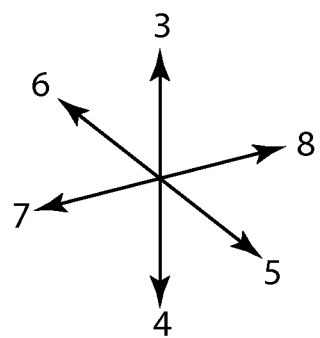
Figure 30:
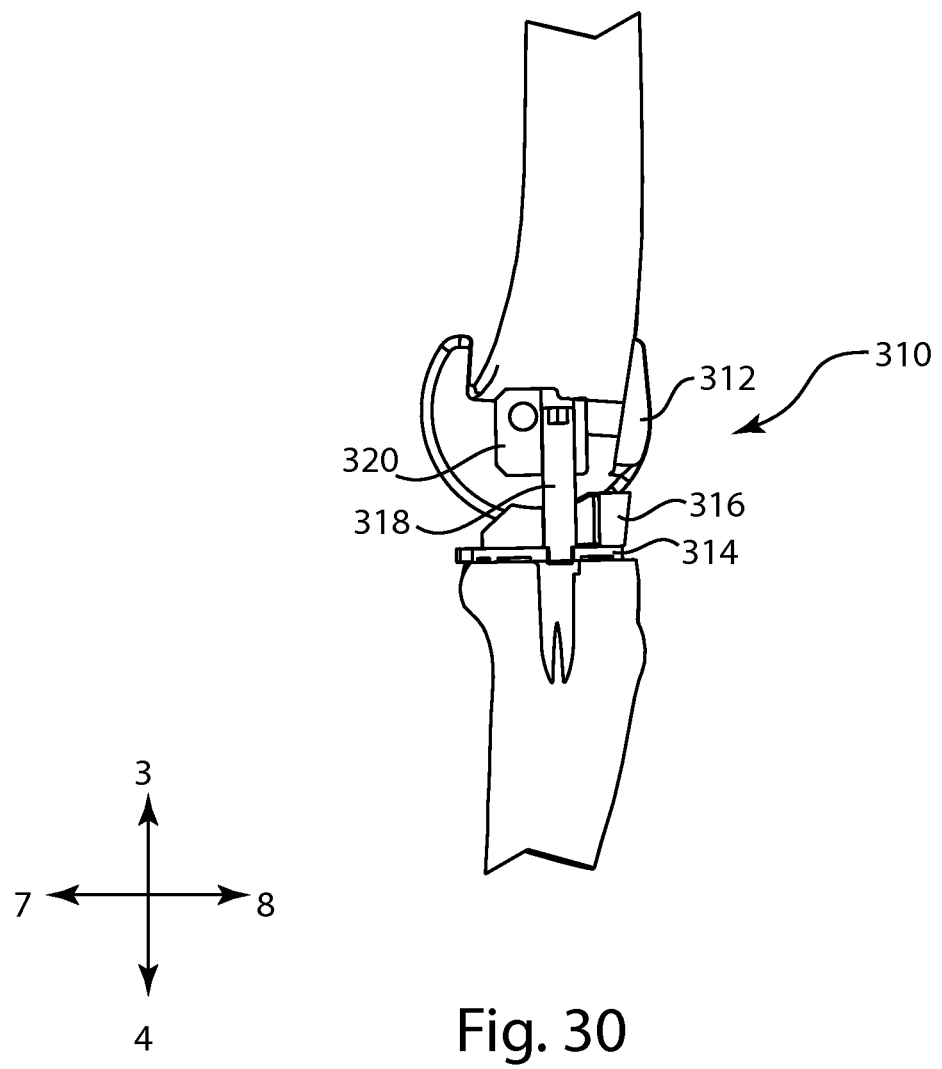
FIG. 30 illustrates a cross section side view of the prosthesis of FIG. 29 with the femoral implant secured to the femur, the femoral implant engaging the hinge block, the hinge block around the cam post, the condyles of the femoral implant articulating against the tibial insert, the tibial insert engaging the tibial baseplate and the tibial baseplate secured to the tibia.
Figure 31:
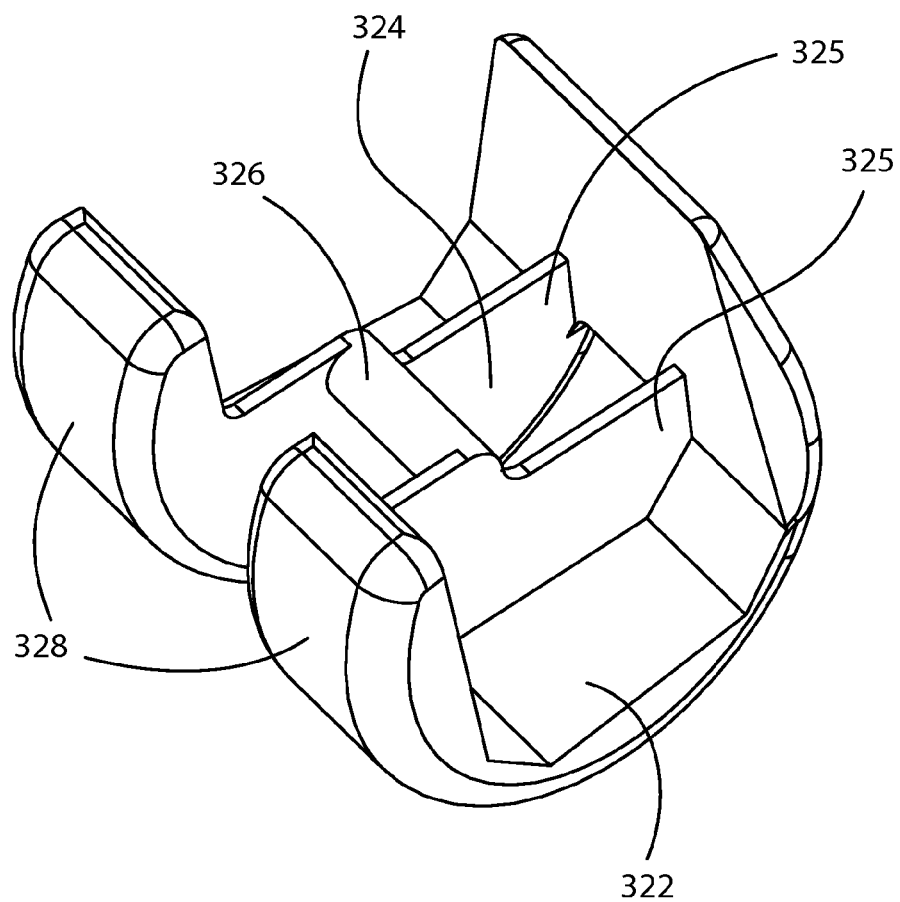
FIG. 31 illustrates a perspective back view of the femoral implant of FIG. 29 with condyles, an opening, opening walls to restrain varus/valgus movement, and an eccentric pin to pass through an opening in the hinge block to stabilize the hinge block (and the prosthesis) within the femoral implant.
Figure 31:
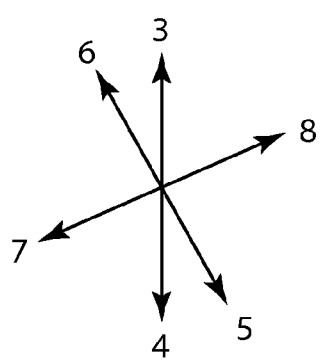

Referring to FIGS. 29 and 30, a further embodiment of a prosthetic knee 310 includes a femoral implant 312, a tibial baseplate 314, a tibial insert 316, a cam post 318 and a hinge block 320. The tibial baseplate 314 and the tibial insert may substantially mirror any of the previous embodiments recited herein with the medial rotational axis. Referring to FIG. 31, the femoral implant 312 is similar to the previous embodiments recited herein with a femur facing side 322, a femoral implant opening 324 and condyles 328 match the curvature of the specific tibial insert 316 chosen for the patient's mobility requirements. However, the femoral implant 312 also includes an eccentric pin 326 which is insertable into the hinge block 320 and opening walls 325 which engage the hinge block and help in preventing varus/valgus displacement and axial distraction, and provide greater medial/lateral stabilization (refer to FIG. 29).

Figure 32:
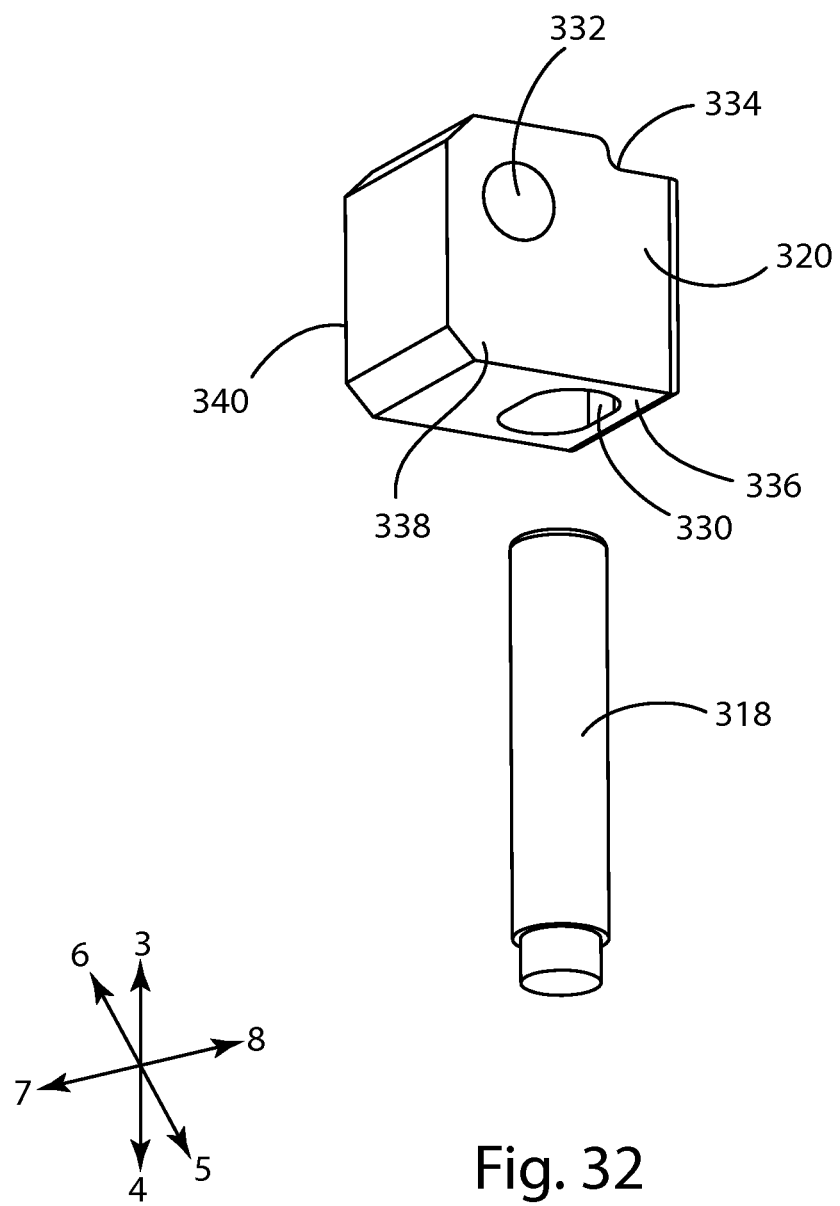
FIG. 32 illustrates a perspective view of the hinge block and cam post of FIG. 29 with the hinge block with a first bore running superiorly/inferiorly for engaging the cam post and a second bore running medial/laterally for engaging the eccentric pin of the femoral implant.
Figure 33:
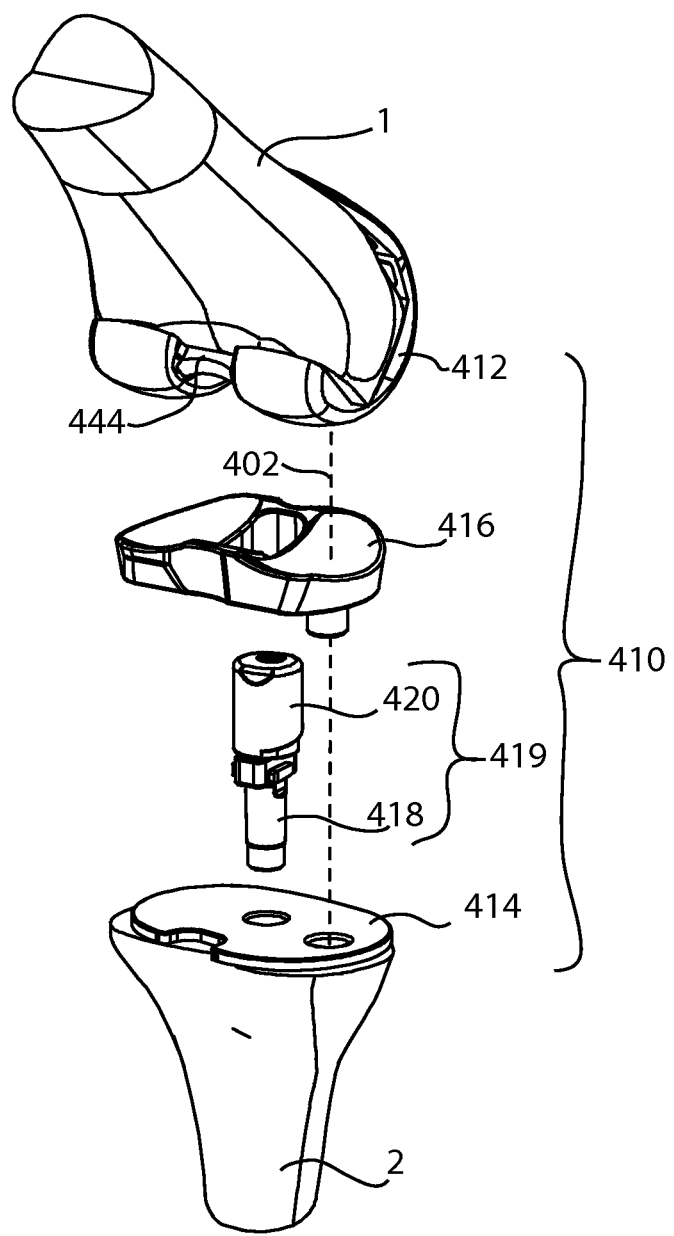
FIG. 33 illustrates a perspective exploded view of an alternate embodiment of a knee prosthesis implanted in a femur and a tibia, the prosthesis including a femoral implant, a tibial bearing insert, a cam post assembly, and a tibial baseplate.

Referring to FIG. 32, the cam post 318 may be substantially circular in cross section with a Morse taper or similar taper toward the inferior end. The hinge block 320 may be substantially rectangular in cross section and may include a first bore 330 extending superiorly/inferiorly through the block from the superior end 334 to the inferior end 336. The first bore 330 is positioned toward the anterior end of the block 320 while the second bore is positioned near the posterior end and superior end 334. The first bore 330 is shaped to slidably receive the cam post 318. The hinge block may also include a second bore 332 extending laterally/medially through the block 320 from the medial end 338 to the lateral end 340. The second bore is positioned and shaped to receive the eccentric pin 326 of the femoral implant 312. The eccentric pin 326 and the opening walls 325 of the femoral implant 312 provide greater medial/lateral stabilization and prevent varus/valgus distraction. The two bores 330, 332 of the hinge block 320 do not intersect. This embodiment may be preferred for those patients that have insufficient, lax or absent medial or lateral stabilizing ligaments.

One method that may be used in placing the prosthetic knee 10 (any of the embodiments will be similar) is to attach the femoral implant 12 and tibial baseplate 14 first to the resected femur 1 and tibia 2 respectively. The order in which either of these is done is left to the preference of the surgeon. After each of the femoral implant 12 and tibial baseplate 14 is secured a trial tibial insert (not shown) with an attached trial cam post (not shown) is positioned on the tibial baseplate to determine the correct size of post and tibial insert to provide for the patients anatomy. The trial cam post is not rigidly connected to the trial insert and can move within the trial tibial insert channel. The trial tibial insert and cam post are removed and the tibial insert 316 is attached to the tibial baseplate through use of the tibial insert boss 24 and the tibial baseplate cavity 22. The knee is the hyper-flexed to allow the cam post 19 to be passed through the tibial insert channel 26 and secured to the tibial baseplate 14 in the tibial baseplate hole 30. The knee is then extended to position the cam post 19 in the femoral implant opening 74.

While this method may be the preferred method, other methods may also be performed such as first attaching the cam post 19 to the tibial baseplate 14 and then passing the tibial insert 16 over cam post 19. The tibial insert 16 may then be secured to the tibial baseplate 14 and the knee extended to engage the cam post 19 with the femoral implant opening 74.

Figure 51:
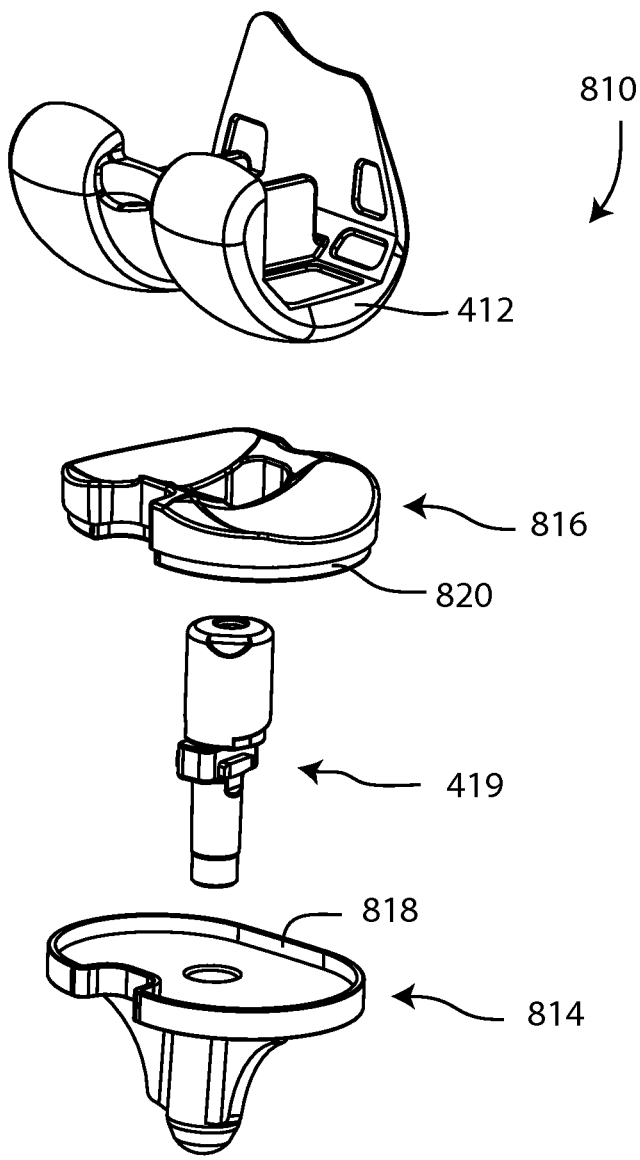
FIG. 51 is a perspective exploded view of an alternate embodiment of a knee prosthesis including a femoral implant, a tibial bearing insert, a cam post, a sleeve, and a tibial baseplate.

FIGS. 33-41 illustrate an alternative embodiment of a prosthetic knee, which can be either a mobile bearing prosthetic knee or a fixed bearing prosthetic knee (if, for example, combined with the elements set forth in FIG. 51). As shown in an exploded view in FIG. 33, knee prosthesis 410 includes femoral component 412, tibial baseplate 414, tibial insert 416, and modular cam post assembly 419 which includes cam post core 418 and sleeve 420. Cam post assembly 419 may be referred to as a support post assembly. The tibial baseplate is configured to be attachable to the resected tibia 2, and the femoral component is configured to be attachable to the resected femur 1. The cam post core 418, which may be referred to as a support post, is shaped to be removably inserted in a recess or opening in the tibial baseplate 414, and is rotatably connectable to the cam post sleeve 420 to form the cam post assembly 419. The cam post assembly 419 helps guide the rotation of tibial insert 416 during flexion of the knee prosthesis 410. The tibial insert 416 is supported by, and rotationally connected to the tibial baseplate 414, and rotatable about a rotation axis 402, which may be a first rotation axis. In this embodiment, rotation axis 402 passes generally vertically through the medial side of the femur, tibial baseplate, tibial insert, and femoral component, and is substantially perpendicular to a superior surface of the tibial baseplate. The rotation axis 402 is medially displaced relative to the geometric centers of the tibial baseplate and the tibial insert. The femoral component 412 is supported by the tibial insert 416 and slidably engages with the cam post assembly 419 to provide weight-bearing support during flexion of the prosthetic knee 410.

One advantage of knee prosthesis 410 is that it can provide motion during knee flexion which is similar to the motion of a normal (non-prosthetic) knee. One attribute of normal knee flexion is that, as the knee flexes, the contact points of the femur on the tibia move posteriorly. This posterior movement of the contact points is known as rollback. In this embodiment, rollback is achieved by having the tibial insert 416 rotate in the posterior direction as the prosthetic knee 410 flexes. Also, in the normal knee rollback is much more pronounced on the lateral side of the knee than the medial side. By having the tibial insert 416 of the prosthetic knee 410 roll back on a medial pivot axis (through contact of a cam feature 444 on the femoral implant 412 with the cam post assembly 419) this prosthesis like the normal knee will have greater rollback on the lateral side than the medial side.

A further advantage of this embodiment is to provide a prosthetic knee, with improved kinematics, which is also suitable for use by patients with collateral ligament deficiency. Patients with this condition need additional support from the prosthetic knee, to provide necessary varus/valgus stability. In this knee design, that varus/valgus stability is provided by the cam post assembly 419 due to its close fit within the opening of the femoral implant 412.

FIGS. 34A-F depict several views of the femoral component 412. The femoral component 412 has a bone facing side 422 and a bearing side 424 opposite the bone facing side, an anterior end 426 and a posterior end 428. A first femoral condyle 430, which may be medial, and a second femoral condyle 432, which may be lateral, extend posteriorly to the posterior end 428 of the component. A trochlear groove 434 is situated between and adjoining the first and second femoral condyles 430, 432 toward the anterior end 426. The first and second femoral condyles 430, 432 may curve cephalically, to match the contours of a natural distal end of a femur and are shaped to align with medial and lateral articulating surfaces of the tibial insert 416. The radius of curvature of the femoral condyles 430, 432 may relatively match the same curvature of the articulating surfaces of the tibial insert 416. The lateral condyle 432 may be longer between the anterior 426 and posterior 428 ends than the medial condyle 430, to match the shape of a natural femur. The condyles 430, 432 may be of various widths, sizes and curvatures depending on the specific anatomy of the patient or tibial insert 416. The surface curvature of the condyles 430, 432 may also vary to match the curvature of the specific tibial insert 416 chosen for the patient's mobility requirements. All or a portion of the bearing side 424 of the femoral component 412 may be polished or include a coating such as titanium nitride to minimize wear between the condyles 430, 432 and the articulating surfaces of the tibial insert 416. If the tibial insert 416 is also made of metal, including those metals named herein, it may also be polished or include treatments to minimize wear.

Figure 34A:
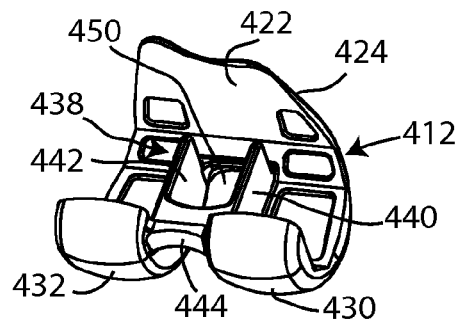
FIG. 34A is an anterior perspective view of the femoral implant of FIG. 33.
Figure 34B:
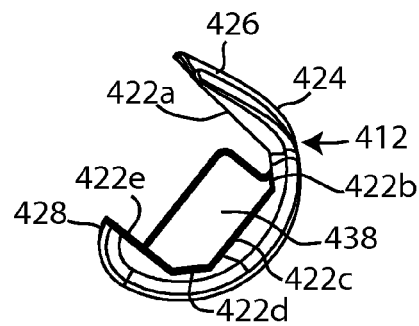
FIG. 34B is a medial side view of the femoral implant of FIG. 33.
Figure 34C:
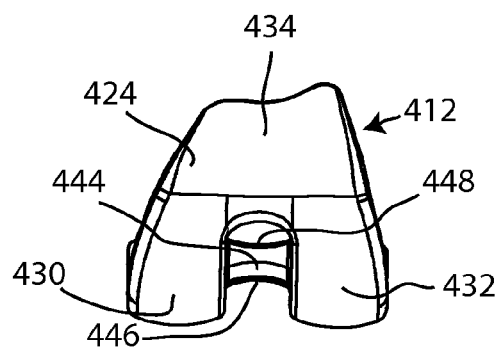
FIG. 34C is an anterior view of the femoral implant of FIG. 33.
Figure 34D:
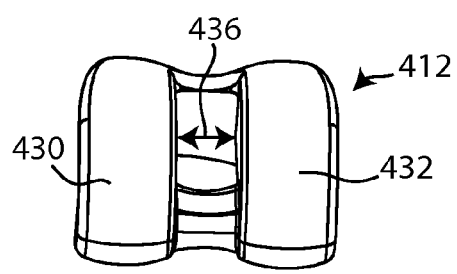
FIG. 34D is an inferior view of the femoral implant of FIG. 33.
Figure 34E:
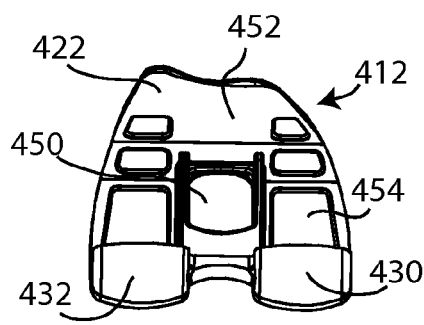
FIG. 34E is a posterior view of the femoral implant of FIG. 33 positioned for extension.
Figure 34F:
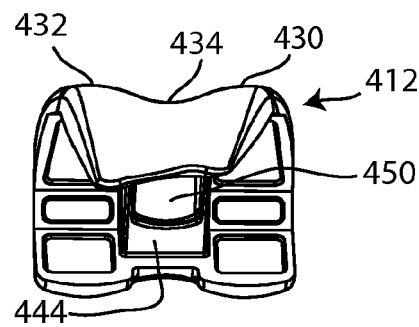
Figure 35A:
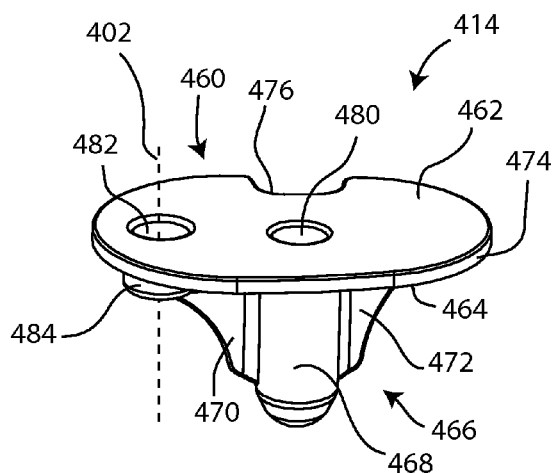
FIG. 35A is an anterior perspective view of the tibial baseplate of FIG. 33.
Figure 35B:
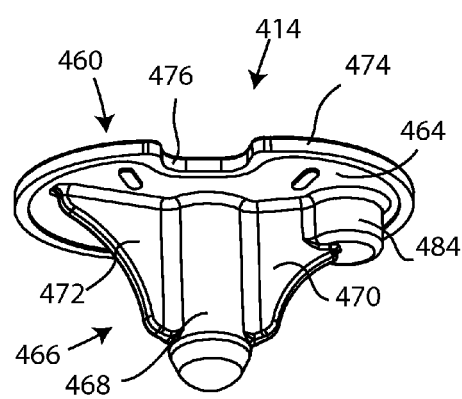
FIG. 35B is a posterior perspective view of the tibial baseplate of FIG. 33.
Figure 35C:
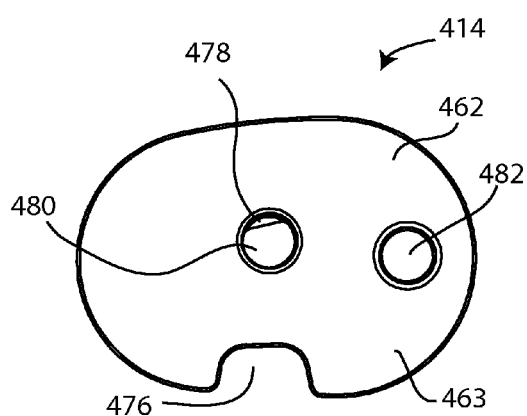
FIG. 35C is a superior view of the tibial baseplate of FIG. 33.
Figure 35D:
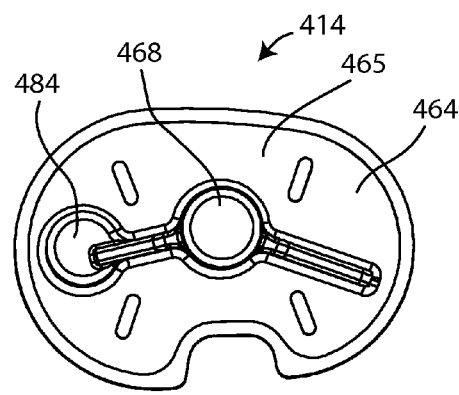
FIG. 35D is an inferior view of the tibial baseplate of FIG. 33.

A gap 436 is formed between the condyles 430, 432 along a majority of their anterior to posterior length and may be continuous with the trochlear groove 434. Gap 436 may be fixed in width as seen in FIG. 34D, but in alternative embodiments the gap width may vary. An intercondylar box 438 may be formed between the condyles 430, 432, including a first or medial intercondylar wall 440, a second or lateral intercondylar wall 442 and a cam feature 444 which bridges the gap between the condyles 430, 432, and joins the walls 440, 442. An L-shape may be formed on the bone-facing side of the cam feature, and the bearing-facing side of the cam feature may be smoothly rounded, or curved. Cam feature 444 includes a first edge 446 which is oriented generally anteriorly, and may be curved to cooperate with cam post assembly 419. A second edge 448 of cam feature 444 is oriented generally posteriorly, and may be also curved. In the embodiment depicted, the medial and lateral intercondylar walls 440, 442 are generally planar, but in alternate embodiments may incorporate curves and/or recesses. The intercondylar box 438 partially surrounds an opening 450 through which the cam post assembly 419 extends which the prosthesis 410 is assembled. The cam post assembly 419 slidably inserts into the opening 450 and a posterior side of the cam post assembly 419 engages the first edge 446 and/or the bearing-facing side of the cam feature 444 during knee flexion.

The bone-facing side 422 may have a bone-facing surface 452 which may comprise a porous material to encourage bone in-growth. Other treatments which enhance bone engagement may also be incorporated, including but not limited to coatings, surface roughening, or surface features such as grooves, pins, pegs or spikes. At least one recess 454 may be formed on the bone-facing side 422. As best seen in FIG. 34B, the bearing side 424 may be continually curving while the curvature on the bone-facing side 422 may be subdivided into a series of adjoining straight segments 422a-422e. The angles of the segments relative to one another may vary, as may the anterior-posterior length of each segment.

It is appreciated that alternative embodiments of the prosthetic knee 410 may include other femoral components such as femoral implants 12, 212, 312 or other femoral components known in the art.

FIGS. 35A-D depict several views of the tibial baseplate 414. Tibial baseplate 414 includes a plate portion 460 having a first, or superior side 462, and a second, or inferior side 464. The inferior side includes a tibia facing surface 465 shaped to lie against a resected surface of a tibia. Projecting inferiorly from the inferior side 464 is a fixation portion 466. In the embodiment depicted, fixation portion 466 includes a generally central post or keel 468, and two wings 470, 472 extending between the keel 470 and the inferior side 464 of the plate portion 460. The keel and wings provide secure, non-rotatable attachment of the tibial baseplate 414 to the resected tibia. The inferior side 464 and fixation portion 466 may include additional pegs, pins, spikes, recesses and/or protrusions to further enhance attachment. The tibial baseplate 414 may preferably be made of cobalt-chrome alloy or titanium alloy; however, other metals, polymer, ceramic, or composite materials may be used. Also, porous materials, surface roughening, and/or coatings, including hydroxyapatite, tricalcium phosphate (TCP) among others may be included to encourage bony attachment of the baseplate 414 to the resected tibia. Other surface treatments or additives may include substances with anti-microbial, analgesic or anti-inflammatory properties.

The superior side 462 includes a planar, or flat superior articulating surface 463, which may also be called a bearing surface. The flat articulating surface 463 allows unencumbered rotation of the tibial insert 416, and may further include surface treatments to improve the wear and friction properties of the surface. One example of this type of coating is titanium nitride; other coatings known in the art to produce the same beneficial effect may be used. It is appreciated that similar coating may be applied to the tibial insert 416. The plate portion 460 is circumscribed by a peripheral wall 474 extending between the superior 462 and inferior 464 sides. A notch 476 may be formed in a posterior part of the peripheral wall. In some embodiments, the notch may allow room for retention of the posterior cruciate ligament (PCL) or another ligament behind the plate 414.

A first bore 480 originates at the superior side 462 of the plate portion 460, and extends through the plate portion and into the keel 468. It is shaped to receive at least a portion of the cam post core 418. A step 478 is formed in the wall of the bore 480 at a preselected depth. As a result, a superior portion of the bore 480 may be circular, while an inferior portion of the bore, inferior to the step, may be irregularly shaped, forming a key feature which prevents rotation of the cam post core 418 in the first bore 480. For example, in the embodiment shown, the inferior portion of the bore has a flattened side, which corresponds to a flattened side on the cam post core 418. In other embodiments, the key feature may comprise another shape, with a correspondingly shaped cam post core. In yet other embodiments, a snap feature may be formed between the cam post core and the tibial baseplate to retain the post in the bore.

A second bore 482 is medially offset from the generally central first bore, and is offset or spaced apart from the peripheral wall 474. Bore 482 extends through the plate portion and into a cup 484 projecting inferiorly from the plate inferior side 464. The second bore 482 may be formed about rotation axis 402 allowing for rotational movement of the tibial insert 416 around that medial axis. The first and second bores 480, 482 may be parallel to one another, and first bore 480 and keel 468 may be longer than second bore 482 and cup 484 to enhance stability of the prosthesis during flexion. The bores may be of equal diameters, as shown, or in other embodiments may be of unequal diameters.

FIGS. 36A-F depict various views of the tibial insert 416, which may also be referred to as a tibial bearing insert. The tibial insert 416 and other tibial inserts disclose herein may comprise any biocompatible material, including but not limited to metals and metal alloys, polymers, ceramics and/or composites. Preferentially, a cobalt-chromium alloy or polyethylene may be used. The tibial insert 416 comprises a femoral implant facing side 490, a tibial baseplate facing side 492, a tibial insert periphery 494 extending around the tibial insert 416 and a tibial insert channel 496 which passes through the tibial insert along a direction generally perpendicular to the baseplate facing side. The tibial insert channel 496 may be arc-like shaped and may be generally centrally located extending from the femoral implant facing side 490 to the tibial baseplate facing side 492, and is shaped to slidably fit over the cam post assembly 419. The tibial channel 496 is large enough and shaped to allow some arc-like rotation of the tibial insert 416 after being positioned over the cam post sleeve 420. The femoral implant facing side 490 includes a first articulating surface 498 and a second articulating surface 499 positioned on opposite sides of the tibial insert channel 496. The first articulating surface 498 may be positioned substantially medial to the insert channel 496 and extend from the insert channel 496 to the tibial insert periphery 494. The second articulating surface 499 may be positioned substantially lateral to the insert channel 496 and extend to the tibial insert periphery 494. The articulating surfaces 498, 499 are shaped and curved to align with the condyles of the femoral implant 412 when the prosthetic knee 410 is implanted in the patient. The articulating surfaces may be sized and/or positioned relative to one another to allow greater rollback on the lateral side than the medial side during knee flexion. For example, the laterally positioned articulating surface 499 may have a longer anterior-posterior length than the medially positioned articulating surface 498.

Figure 36A:
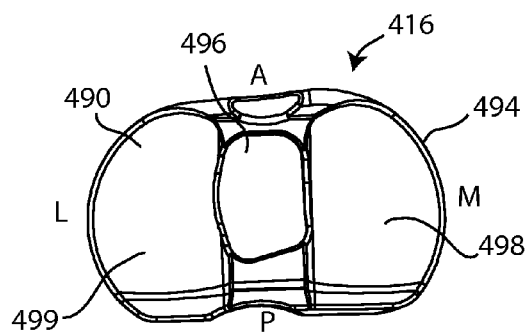
FIG. 36A is a superior view of the tibial bearing insert of FIG. 33.
Figure 36B:
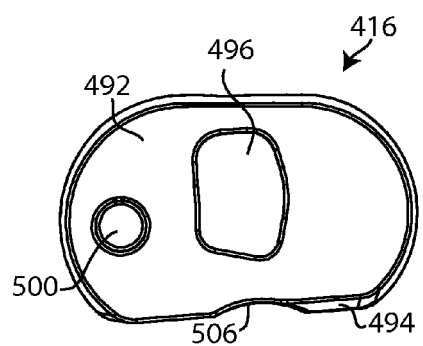
FIG. 36B is an inferior view of the tibial bearing insert of FIG. 33.
Figure 36C:
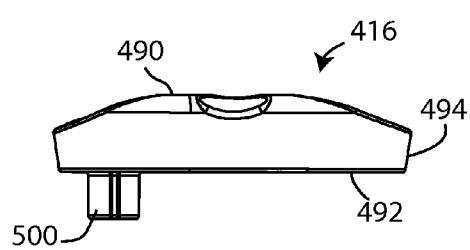
FIG. 36C is an anterior view of the tibial bearing insert of FIG. 33.
Figure 36D:
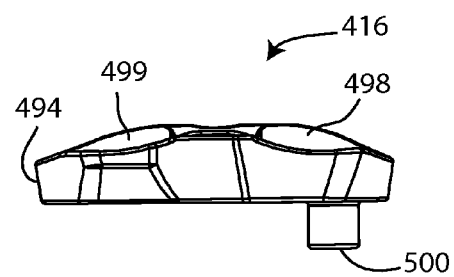
FIG. 36D is an posterior view of the tibial bearing insert of FIG. 33.
Figure 36E:
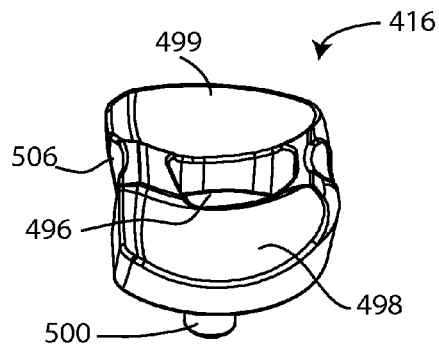
FIG. 36E is a perspective medial view of the tibial bearing insert of FIG. 33.
Figure 36F:
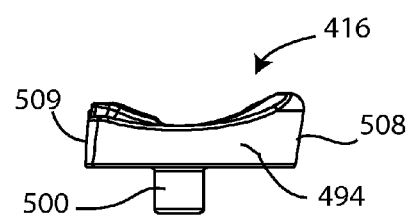
FIG. 36F is a medial view of the tibial bearing insert of FIG. 33.

Referring to FIGS. 36B-D, the tibial baseplate facing side 492 may be substantially flat with the exception of a boss 500 extending inferiorly, positioned toward the medial side of the tibial baseplate 414 but apart from the tibial insert periphery 494. When assembled, the flat tibial baseplate facing side 492 may align with the flat superior side 462 of the tibial baseplate 414, with the boss 500 positioned within the second bore 482 of the tibial baseplate 414. There may be a gap between the bottom or inferior surface of the boss 500, and the bottom or inferior surface of the second bore 482. The cylindrical sides of the boss 500 may have a clearance fit with the second bore 482 to allow smooth rotation of the boss within the bore. During knee flexion/extension, the tibial insert 416 may pivotally rotate about rotation axis 402, defined by the second bore 482. The insert 416 may rotate along an arc-shaped path in relation to the tibial insert channel 496 and the cam post assembly 419. The rotational motion of the tibial insert 416 is limited by engagement of the tibial insert channel 496 with the cam post assembly 419. In the context of this application, motion limitation refers to prohibition of motion along one or more paths or directions, including prohibition of motion along any direction, or all directions.

A tibial insert notch 506 may be positioned along the tibial insert periphery 494 toward the posterior end of the tibial insert 416. The tibial insert notch 506 may be aligned with the tibial baseplate notch 476 and may allow room for retention of the posterior cruciate ligament (PCL) or another ligament behind the tibial baseplate 414 and the tibial insert 416. The height of the insert at an anterior end 508 may be greater than the height of the insert at a posterior end 509, in order to more closely replicate natural knee anatomy.

Figures 38A, 38B:
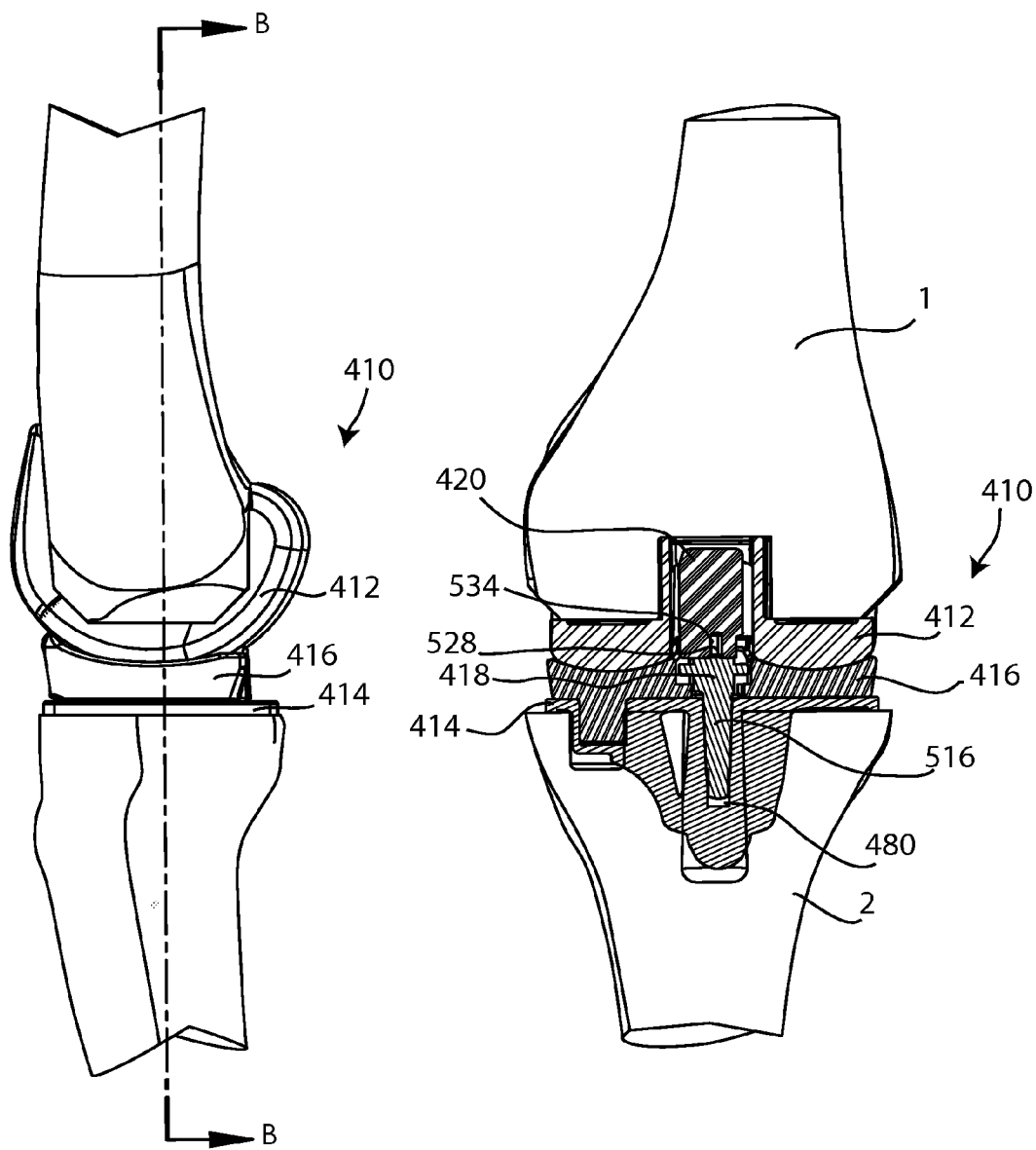
FIG. 38A is a side view of the prosthesis of FIG. 33 implanted in a tibia and a femur.
FIG. 38B is an anterior cross-sectional view of the prosthesis of FIG. 33 taken along line B-B.

FIGS. 37A-D depict exploded views of cam post assembly 419 from various perspectives, and FIG. 38B depicts a anterior cross-sectional view of knee prosthesis 410 implanted into a prepared tibia and femur. Referring to lateral perspective view 37A, cam post 418 includes an inferior post portion 510 and a superior post portion 512, which are separated by an intermediate block portion 514. The central longitudinal axes of each post portion 510, 512 may not be co-axial, as seen in FIG. 37A and FIG. 39, although the post portions may have overlapping outer diameters when viewed from a superior or inferior perspective. Inferior post portion 510 includes a body segment 516, a first end segment 518, and a key feature 520 which cooperates with a corresponding key feature 478 on the tibial baseplate 414 to prevent rotation of the cam post 418 within the first bore 480 when assembled together. The diameter of the body segment 516 is frustoconical, so that the inferior post portion 510 fits into the first bore 480 with a Morse-style tapered fit, as seen in FIG. 38. Thus when properly attached together, there is a rigid, non-rotatable connection between the cam post core 418 and the tibial baseplate 414. Cam post core 418 and cam post assembly 419, and other modular cam posts and assemblies described herein, can be described as removably attachable to the tibial baseplate, meaning that they can be intentionally attached and/or removed without destroying or damaging any parts, for example during a cam post assembly replacement or revision procedure.

The intermediate block portion 514 comprises a generally rectangular shape, having a block length, a block width, and a block height. The dimensions of the intermediate block portion 514 allow it to be received in the channel 496 of the insert 416 with clearance on all sides. The intermediate block portion 514 comprises a first block end 521 which may be at an anterior end of the block, and a second block end 523 which may be at a posterior end of the block, opposite the first block end. The first and second block ends may provide stops or limits to the rotational motion of the tibial insert 416 during knee flexion/extension, through direct contact with anterior and posterior ends of channel 496. The block length is greater than the diameter of the inferior post body segment 516, and likewise greater than the diameter of the first bore 480, so that the block length extends generally anteriorly and posteriorly past the outer diameters of the inferior post portion 510 and first bore 480 when assembled. The block width may also be greater than the diameters of the inferior post portion 510 and the first bore. At least one tab 522 is positioned on the intermediate block portion 514, which can provide a feature for an instrument to engage with for removal and/or insertion of the cam post core 418. In other embodiments other instrument engagement features may be included, included but not limited to recesses, tabs, protrusions, hooks, loops or other features for engagement of an instrument.

The superior post portion 512 extends superiorly from the intermediate block portion 514, and is partially offset from the inferior post portion 510. The superior post portion 512 is generally cylindrical, and may include a flange 524 positioned on a second end segment 526 of reduced diameter. The flange 524, which may be annular, provides a mechanism for a snap fit between the cam post core 418 and the sleeve 420, as seen in FIG. 39. A stop tab 528 projects superiorly from the intermediate block portion 514, and may adjoin the superior post portion 512. When the sleeve 420 and cam post core 418 are snap fitted together, the sleeve 420 is still rotatable relative to the superior post portion 512, although rotation may be limited by the stop tab 528.

Sleeve 420 includes a sleeve body 530, through which a sleeve bore 532 extends superior-inferiorly, and is positioned eccentrically to the outside diameter of the sleeve body. Toward its inferior end, the sleeve bore 532 includes an alcove 534. The alcove 534 is sized and shaped such that when the sleeve 420 is fitted onto the cam post core 418 with the superior post portion 512 extending into the sleeve bore 532, the stop tab 528 is received in the alcove 534. Sleeve 420 can rotate relative to cam post core 418 only through a predetermined angle, limited by interaction of stop tab 528 with side walls 531, 533 of the alcove 534. An annular interior flange 535, visible in FIG. 39B, is formed in the sleeve bore 532 to provide the snap fit between the sleeve 420 and the cam post core 418. A vertical protrusion 536 is formed on the outer surface of the sleeve body 530, and extends inferiorly from the superior end of the sleeve body. A sloped, or chamfered edge 538 is formed on each side of the vertical protrusion 536, providing a gradual slope between the sleeve body 530 and the apex of the protrusion 536. The chamfered edges 538 may provide stops for rotational motion between the sleeve 420 and the walls of the intercondylar box 438 during flexion/extension of the knee prosthesis. A semicircular recess 540 is formed around a portion of the inferior end of the sleeve body 530. The recess 540 provides clearance for the tibial insert 416 as it rotates relative to the sleeve 420. Sleeve 420 may be made of a biocompatible polymer.

Knee prosthesis 410 may be implanted into a prepared space between a resected femur and tibia using the same procedures described herein for knee prosthesis 10.

Figure 40A:
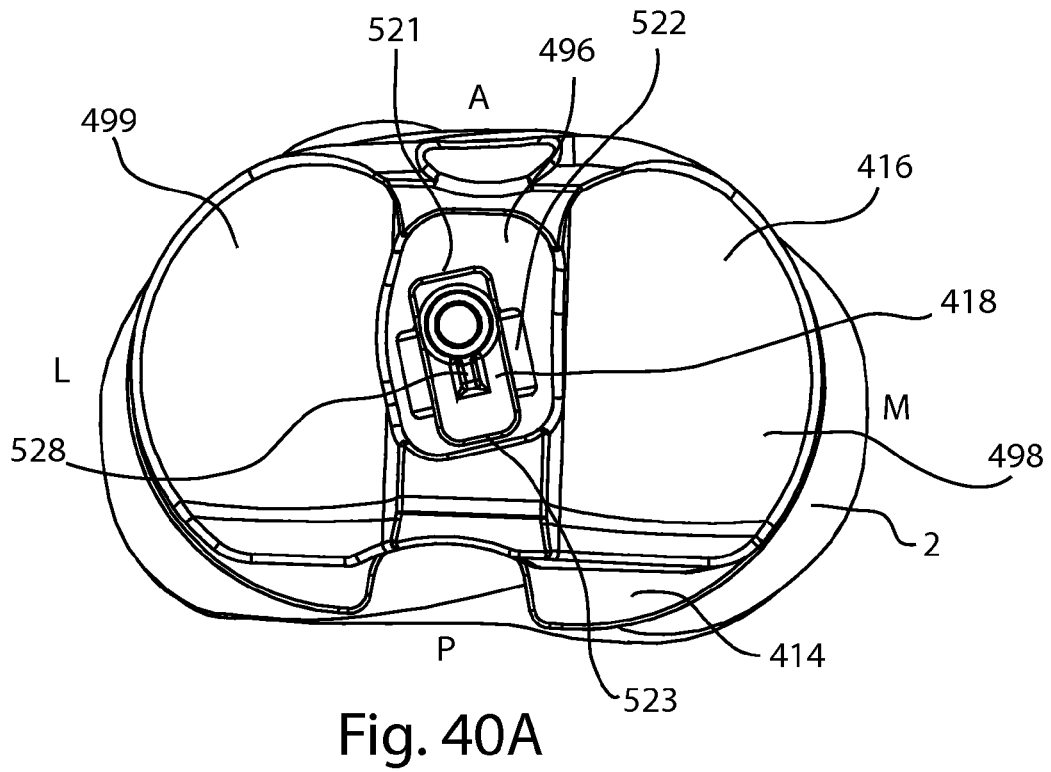
FIG. 40A is a superior view of a subassembly of the tibial baseplate, tibial bearing insert and cam post of FIG. 33 implanted in a tibia, with the tibial bearing insert in an extension position.
Figure 40B:
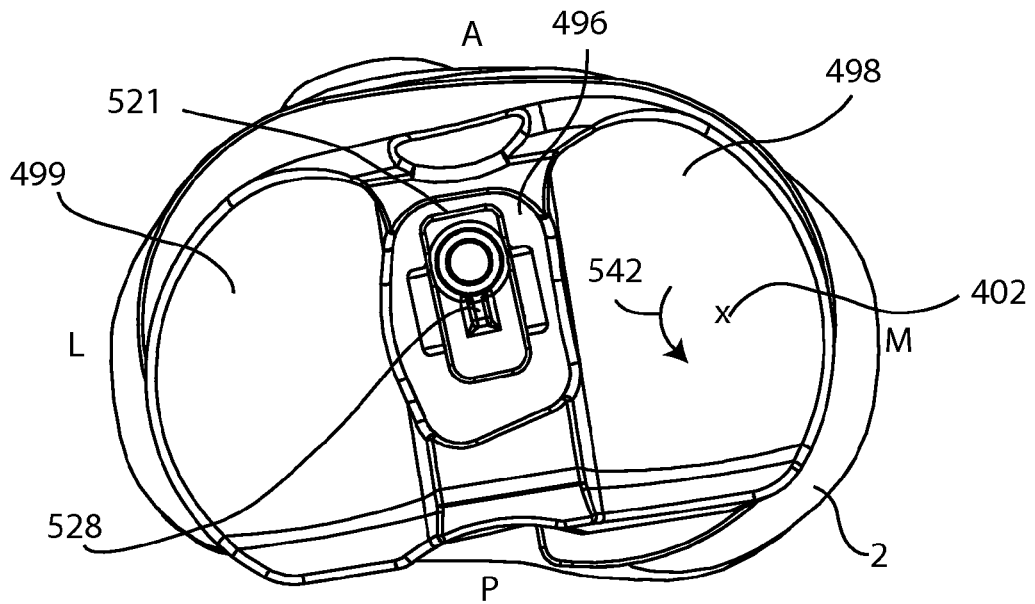
FIG. 40B is a is a superior view of the subassembly of FIG. 40A, with the tibial bearing insert rotated about a rotation axis to a position of flexion.
Figure 41A:
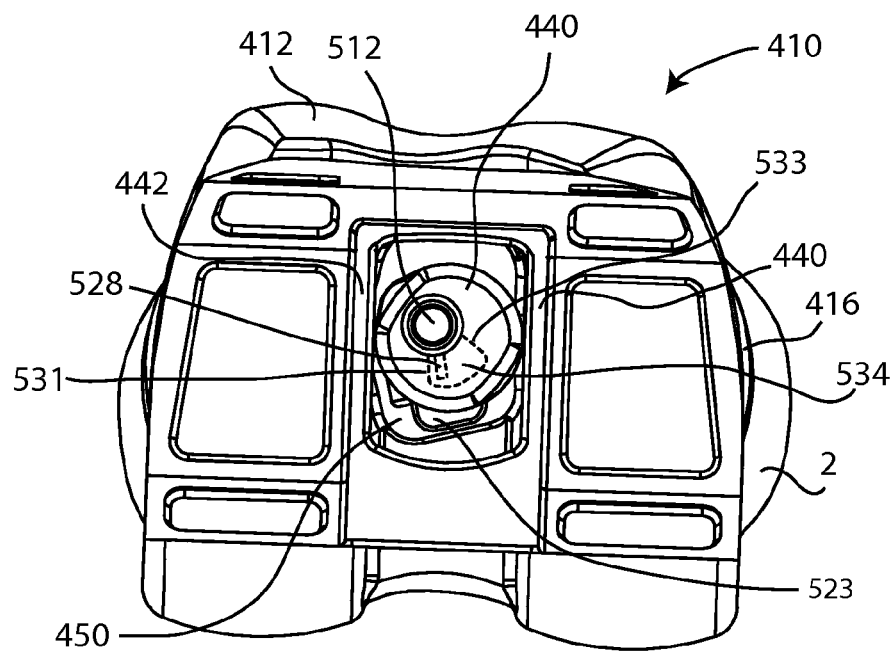
FIG. 41A is a superior view of the prosthesis of FIG. 33 implanted in a tibia, the prosthesis in a position of extension, with a sleeve of the cam post assembly rotated in a first direction.
Figure 41B:
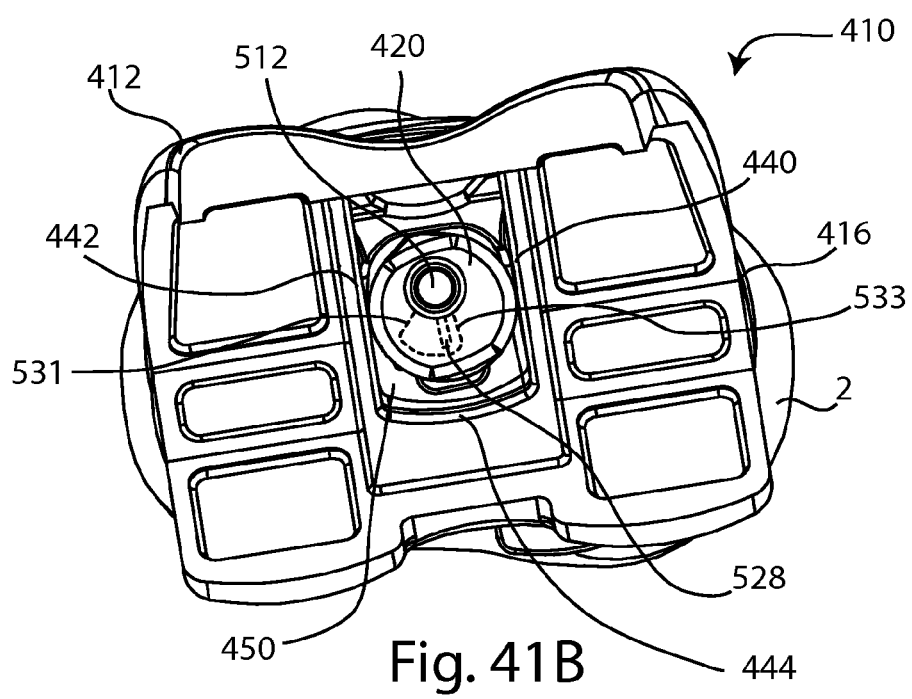
FIG. 41B illustrates the prosthesis of FIG. 41A in a position of flexion, with the sleeve of the cam post assembly rotated in a second direction opposite the first direction, and the bearing insert rotated in the first direction.
Figure 42:
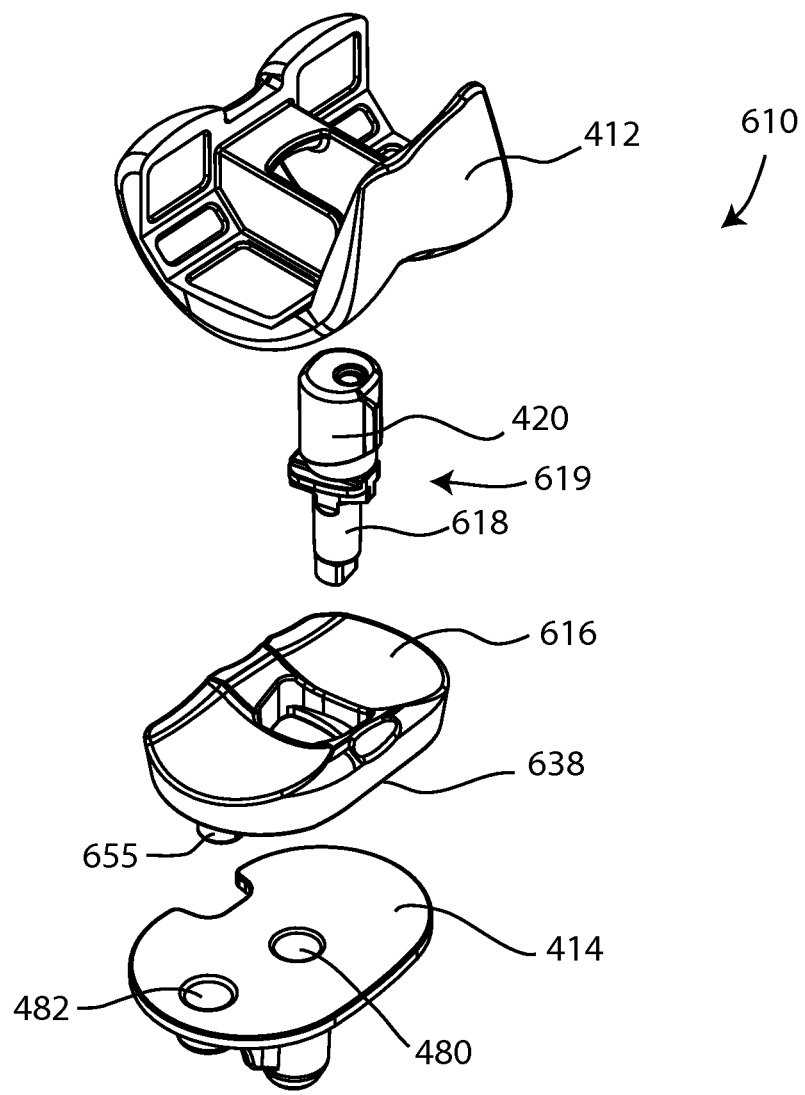
FIG. 42 is a perspective exploded view of an alternate embodiment of a knee prosthesis including a femoral implant, a tibial bearing insert, a cam post assembly, and a tibial baseplate.

FIGS. 40A-B and 41A-B illustrate some aspects of the kinematics of knee prosthesis 410. Referring to FIG. 40A, when the knee is in extension, the tibial insert 416 is substantially centered over the tibial baseplate 414, both anterior-posteriorly and medial-laterally. The second block end 523 of the cam post core 418 is at or approaching the posterior end of the tibial insert channel 496. During flexion, as seen in FIG. 40B, the tibial insert 416 rotates posteriorly about rotation axis 402 as indicated by direction arrow 542. This medialized rotation results in relatively greater posterior movement of the lateral second articulating surface 499 than the medial first articulating surface 498. The tibial insert 416 is no longer substantially centered over the tibial baseplate 414 but is at skewed at an angle across both the sagittal and coronal plane of the knee. The first block end 521 of the cam post core 418 is at or approaching the anterior end of the tibial insert channel 496. Although flexion of 30° is illustrated in FIGS. 40B and 41B, it is appreciated that a greater degree of flexion will result in additional posterior rotation of the tibial insert 416, and vice versa.

FIGS. 41A and 41B show the relative movement of the sleeve 420 and femoral implant 412 during knee extension and flexion. Referring to FIG. 41A, when the knee is in extension, the femoral implant 412 is substantially centered over the tibial insert 416 and the tibial baseplate 414 (not visible), both anterior-posteriorly and medial-laterally. Within sleeve 420, stop tab 528 is at or near side wall 531, preventing further lateral rotation of sleeve 420. Referring to FIG. 41B, when the knee is articulated during flexion, the femoral implant 412 rotates posteriorly about the medial rotation axis and slidingly engages the tibial insert with the condyles 430, 432 articulating with the articulating surfaces 498, 499 of the tibial insert. The cam feature 444 may be in engagement with the cam post assembly to provide rollback and femoral external rotation during knee flexion. This motion results in greater rollback on the lateral side than on the medial side, thus reproducing normal knee kinematics. During knee flexion the sleeve 420 rotates on the cam post core 419, urged by the sliding engagement of sleeve 420 with at least one, or both, femoral implant walls 440, 442. This rotation occurs automatically, and is necessary because of the medial pivot axis 402 of the tibial insert 416. As the tibial insert 416 rotates about axis 402, the sleeve 420 rotates in the opposite direction about superior cam post portion 512 to center itself inside the opening 450 of the femoral implant 412. This self centering is possible because of the off-center positioning of the sleeve bore 532 inside the sleeve 420. The diameter of sleeve 420 may be slightly smaller than the distance between femoral implant walls 440, 442 to allow for slight varus/valgus motion while still providing varus/valgus support.

During both extension and flexion, the close fit of the intercondylar box walls 440, 442 to the sleeve 420 provides varus/valgus support to the femoral implant 412 and thus to the femur. At least one wall 440, 442 may directly contact cam post assembly 419 via sleeve 420 to provide the varus/valgus support. However, the cam post assembly can be slightly smaller than the opening in the femoral implant, to allow a slight amount of varus/valgus motion. The sleeve stop tab 528 in engagement with either alcove side wall 531, 533 forms a rotation limiting mechanism which may prevent over-rotation in either direction, as may the engagement of the sleeve vertical protrusion 436 with the intercondylar box wall 442.

FIGS. 42-45 illustrate an alternative embodiment of a knee prosthesis having a captive tibial insert. The knee prosthesis can be either a mobile bearing prosthetic knee or a fixed bearing prosthetic knee (if, for example, combined with the elements set forth in FIG. 51). Knee prosthesis 610 includes femoral implant 412, tibial baseplate 414, tibial bearing insert 616, and cam post assembly 619 which includes cam post 618 and rotatable outer sleeve 420. Knee prosthesis 610 includes a retaining mechanism to capture the tibial insert in its proper position with respect to the tibial baseplate, and prevent lifting or distraction of the tibial insert off of the tibial baseplate, while still allowing rotation of the insert relative to the baseplate. With respect to other functions of the prosthesis, including but not limited to rotation of the tibial insert relative to the tibial baseplate, rotation of the sleeve relative to the cam post core and the femoral implant, varus/valgus support, and greater lateral rollback, prosthesis 610 may function the same as knee prosthesis 410 as described herein.

Figure 43A:
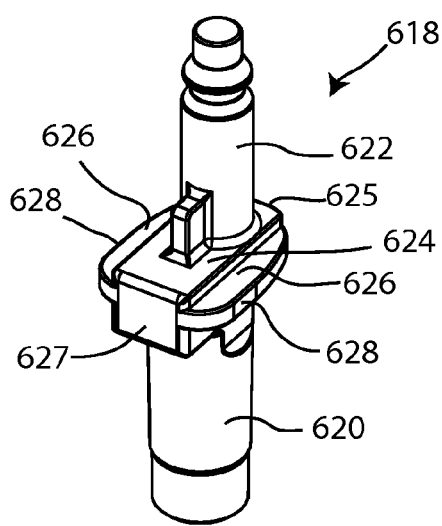
FIG. 43A is a posterior perspective view of a cam post of the cam post assembly of FIG. 42.
Figure 43B:
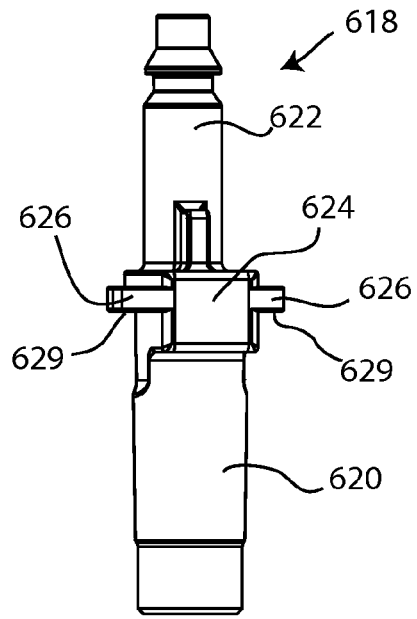
FIG. 43B is a posterior view of the cam post of FIG. 43A.
Figure 43C:
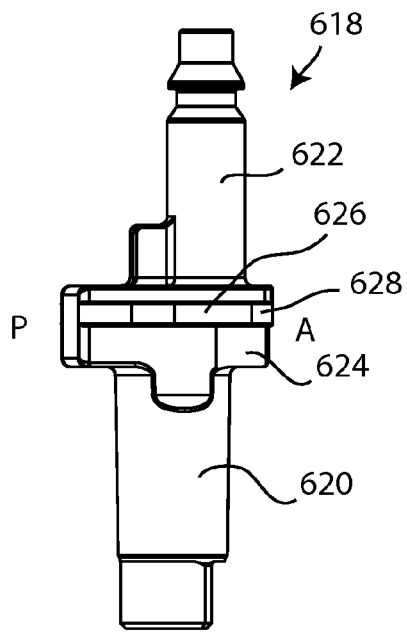
FIG. 43C is a side of the cam post of FIG. 43A.
Figure 43D:
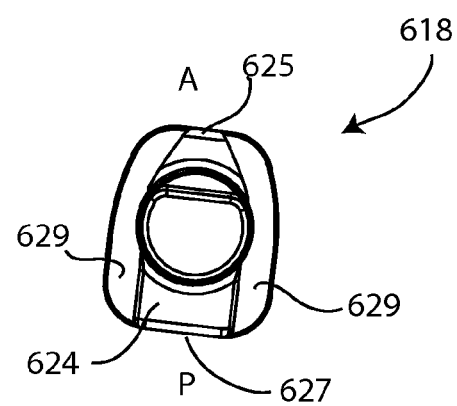
FIG. 43D is an inferior view of the cam post of FIG. 43A.

Referring to FIGS. 43A-C, cam post 618 includes inferior post portion 620, superior post portion 622, and intermediate block portion 624. With the exception of the tibial insert retention features formed on cam post 618, cam post 618 may be the same as cam post 418 and the description herein of cam post 418 applies to cam post 618, and will not be repeated here. A pair of retention tabs 626 project outwardly from the intermediate block portion 624, and extend the length of the intermediate block portion. An outer edge 628 of each retention tab 626 is curved to allow smooth guided interaction of the retention tabs with a channel in the tibial insert 616. On the bottom side of each retention tab is formed a tab bearing surface 629. Under the retention tabs, an anterior end 625 of the intermediate block portion 624 may be narrower than a posterior end 627, as seen in FIG. 43D. This taper may allow smoother guided rotation of the tibial insert 616 about the cam post core 618. In other embodiments of the invention, the cam post 618 may include only one retention tab, or a plurality of retention tabs. The retention tab(s) may include outer edges with various curve shapes, or may include straight edges, or a combination thereof. The height and placement of the retention tabs may vary. It is appreciated that the retention tabs 626 may also serve the purpose of an engagement feature for interaction with an instrument for insertion or removal of the cam post core 618 or other prosthesis components. For example, an instrument could grasp, hook onto, slide under, or otherwise engage retention tabs 626.

Figure 44A:
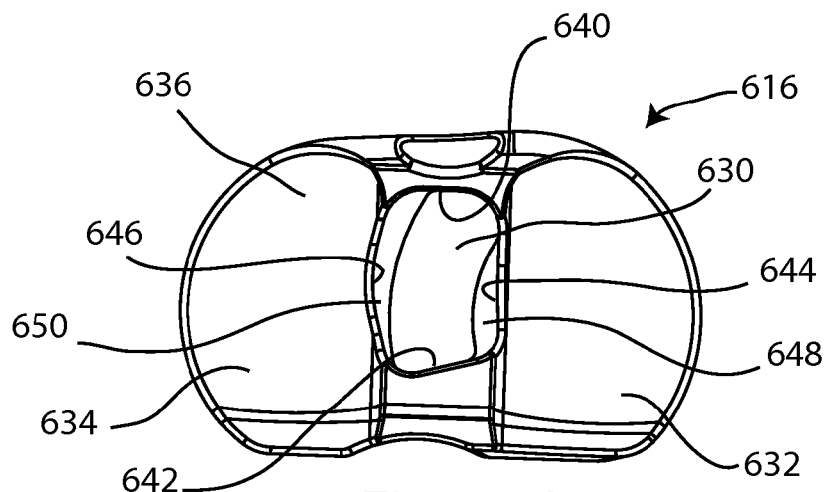
FIG. 44A is a superior view of the tibial bearing insert of FIG. 42.
Figure 44B:
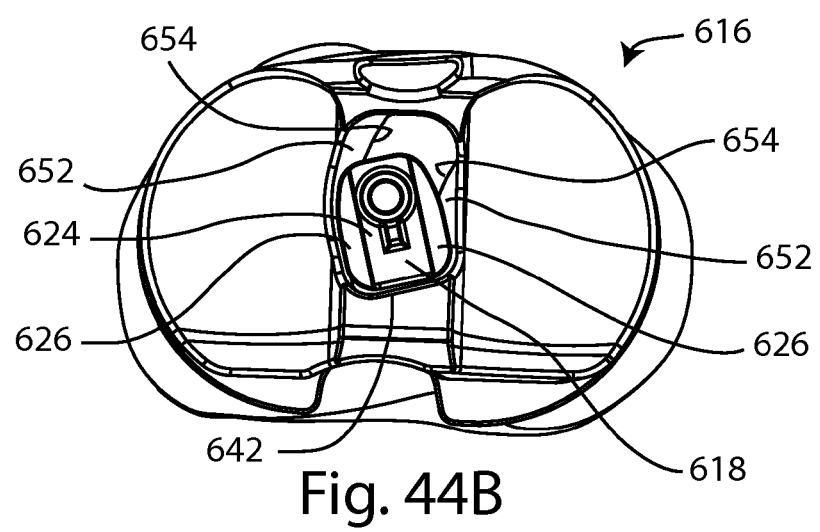
FIG. 44B is a superior view of a subassembly of the tibial baseplate, tibial bearing insert and cam post of FIG. 42 implanted in a tibia, with the tibial bearing insert in an extension position.
Figure 44C:
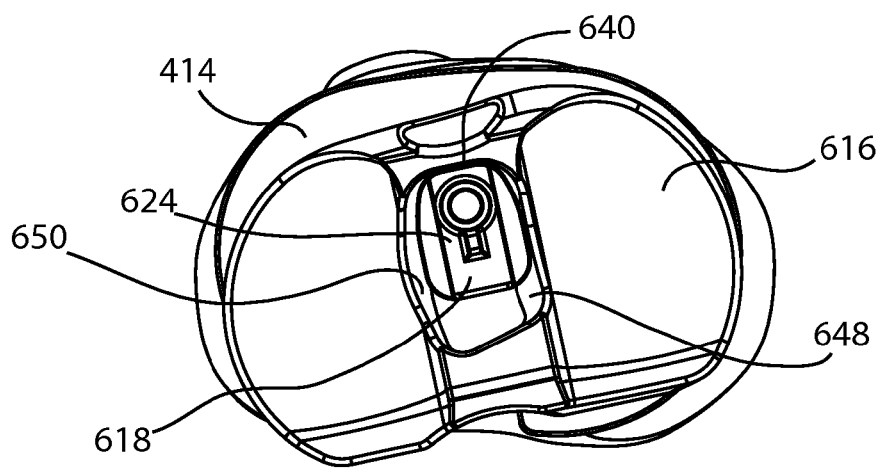
FIG. 44C is a is a superior view of the subassembly of FIG. 44B, with the tibial bearing insert rotated about a rotation axis to a position of flexion.

Referring to FIGS. 44A-C, tibial bearing insert 616 may be implanted in cooperation with cam post core 618. With the exception of the channel features formed on tibial bearing insert 616, tibial insert 616 may be the same as tibial insert 416 and the description herein of tibial insert 416 applies to tibial insert 616, and will not be repeated here. For example, the overall size and shape, periphery, and articulating surfaces on tibial insert 616 may be the same as tibial insert 416. Tibial insert 616 includes channel 630, which extends general anterior-posteriorly between medial and lateral articulating surfaces 632, 634. The channel 630 is an opening extending between a femoral implant facing side 636, and a tibial baseplate facing side 638. Anterior 640 and posterior 642 ends of the channel 630 may provide a rotation stops for rotation of the tibial insert 616 relative to the cam post assembly 619 and the tibial tray 414. Channel 630 may be generally arc-shaped, wherein the anterior and posterior ends 640, 642 are not parallel to one another, and wherein at least one of a medial 644 and a lateral 646 sidewall of the channel 630 is curved. Extending along at least a portion of the medial sidewall 644 is a first, or medial step 648; and extending along at least a portion of the lateral sidewall 644 is a second, or lateral step 650. Each of the medial and lateral steps includes a bearing surface 652 and an step edge 654. The step edges 654 may be curved, and may guide rotation of the tibial insert 616 along an anterior-posterior curved path. The step edges 654 may be parallel to one another. A boss 655 protrudes inferiorly from tibial baseplate facing side 628.

Figure 45:
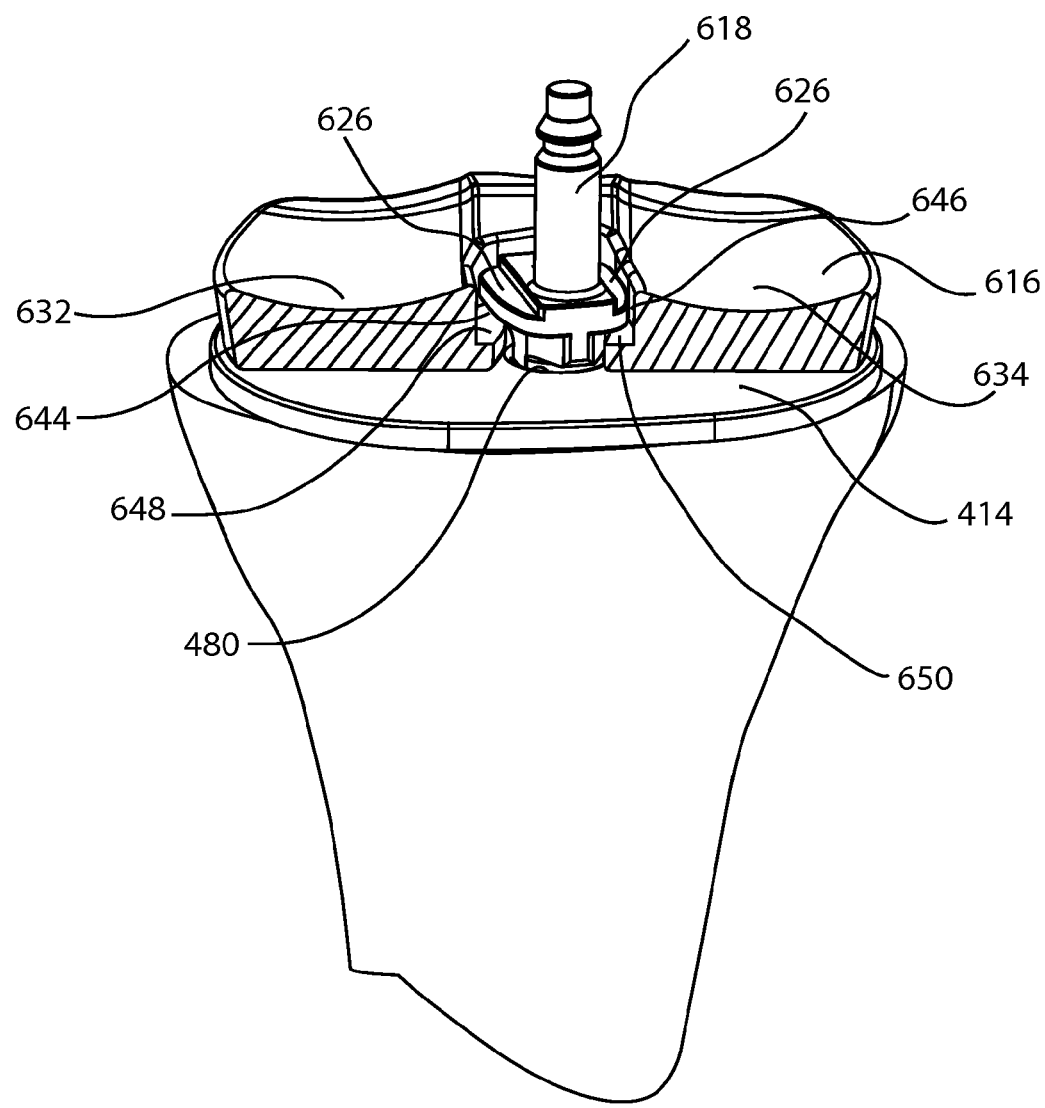
FIG. 45 is an anterior cutaway view of the subassembly of FIG. 44B, showing the retention of the tibial bearing insert by the cam post.

FIG. 45 depicts a partial cross-sectional view of the tibial insert 616 and cam post core 618. In one method of implantation of knee prosthesis 610, tibial 414 and femoral 412 components, and sleeve 420 are implanted as described herein for other embodiments of the knee prosthesis. Tibial insert 616 is positioned on tibial baseplate 414 with channel 630 over first bore 480, and boss 655 fits into second bore 482, seen in FIG. 42. The inferior post portion 620 is inserted through channel 630 and into first bore 480. When insertion is complete, retention tabs 626 are positioned to at least partially overlap, and may slidably contact, steps 648, 650. Bearing surface 652 on each step may slide along tab bearing surface 629 on the corresponding tab. The remainder of the implantation process may be as described for other embodiments of the invention. During knee flexion, as seen in FIG. 44C, tibial insert 616 rotates about the medial axis, and channel 630 slides in an arcuate path posteriorly along cam post core 618. Steps 648, 650 slide under retention tabs 626, with a portion of the retention tabs overlapping a portion of the steps at any rotational position of the insert to form the retention mechanism. Thus, rotation of the tibial insert 616 is permitted, but distraction or lifting of the insert away from the tibial baseplate 414 is prohibited. For example, unintentional expulsion of boss 655 out of second bore 482 is prevented. The anterior end of intermediate block portion 624 may abut against the anterior channel end 640 to limit, or stop posterior rotation of the insert. During extension, as seen in FIG. 44B, the tibial insert 616 rotates general anteriorly, with steps 648, 650 captured and sliding under retention tabs 626. The posterior end of intermediate block portion 624 may abut against the posterior channel end 642 to stop anterior rotation of the insert. The steps 648, 650, intermediate block portion 624, and/or retention tabs 626 may further include surface treatments to improve the wear and friction properties of their surfaces to promote optimal unencumbered knee movement.

Figure 46:
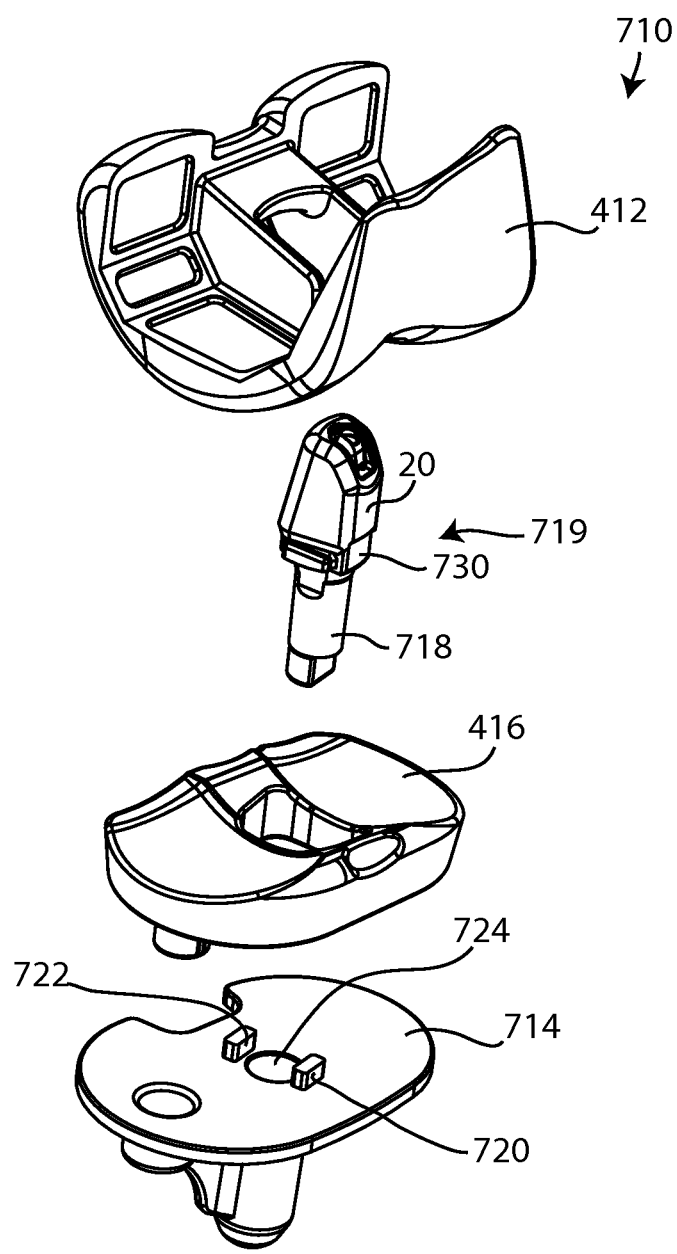
FIG. 46 is a perspective exploded view of an alternate embodiment of a knee prosthesis including a femoral implant, a tibial bearing insert, a cam post assembly, and a tibial baseplate.
Figure 47A:
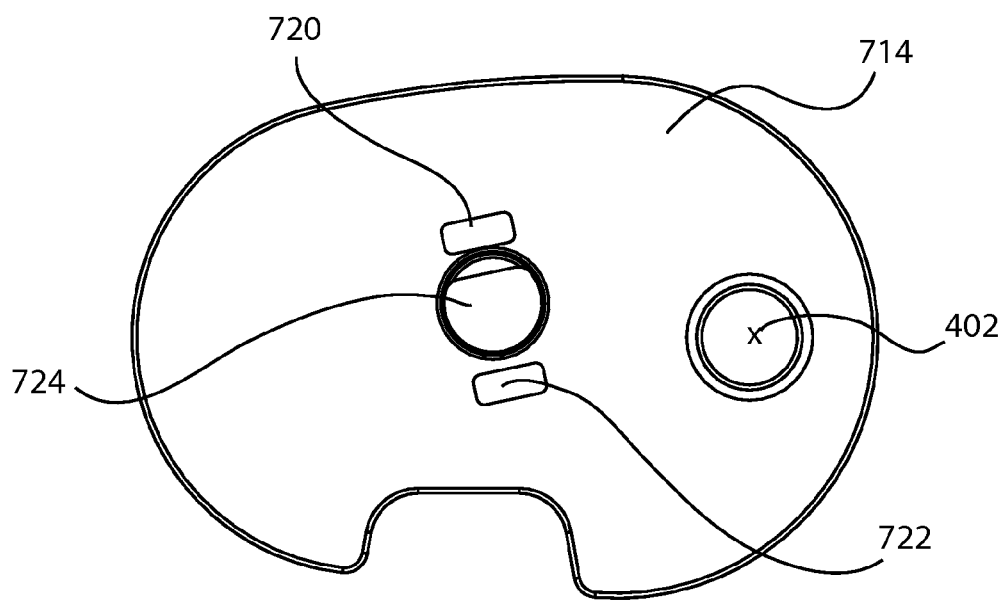
FIG. 47A is a superior view of the tibial baseplate of FIG. 46, the tibial baseplate including anterior and posterior stop features.
Figure 47B:
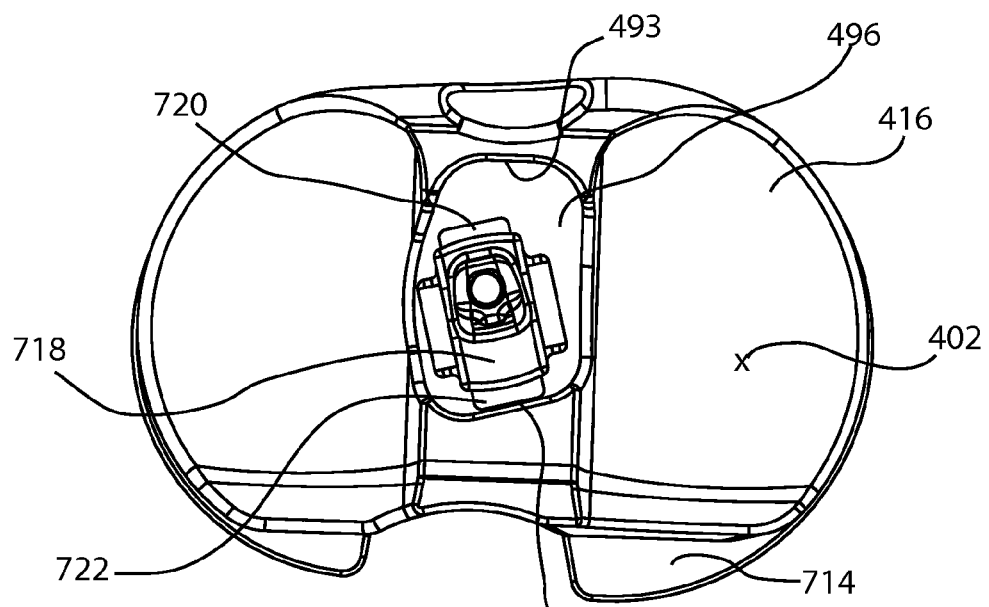
FIG. 47B is a superior view of a subassembly of the tibial baseplate, tibial bearing insert, and cam post of FIG. 46 in a position of flexion.
Figure 48A:
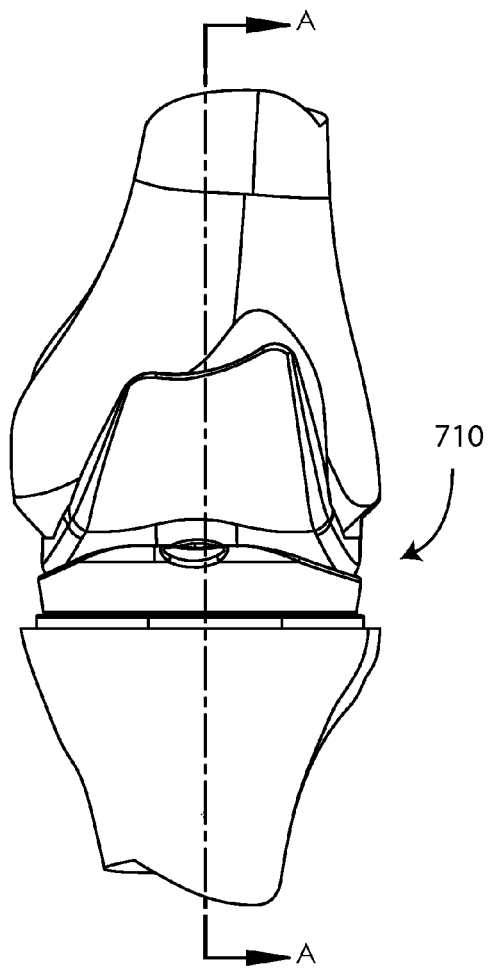
FIG. 48A is an anterior view of the prosthesis of FIG. 46 implanted in a tibia and a femur.

Another embodiment of a knee prosthesis is shown in FIGS. 46-48. The knee prosthesis can be either a mobile bearing prosthetic knee or a fixed bearing prosthetic knee (if, for example, combined with the elements set forth in FIG. 51). Prosthesis 710 includes femoral implant 412, tibial baseplate 714, tibial insert 416, and cam post assembly 719, which includes cam post core 718 and sleeve 20. As described above for other embodiments including prostheses 410 and 610, knee prosthesis 710 may provide rotation of the tibial insert about the medial rotation axis, varus-valgus stability, and greater rollback on the lateral side than the medial side. Additionally, prosthesis 710 includes at least one motion limiting feature provided between the tibial baseplate and the tibial insert. Referring to FIGS. 47A, 47B, and 48, tibial baseplate 714 includes a first, or anterior stop 720, and a second, or posterior stop 722, either of which may engage the tibial insert 416 to limit motion of the tibial insert. Stops 720, 722 are structures projecting superiorly from the superior or bearing facing surface of the tibial baseplate 714. The stops 720, 722 may be immediately anterior and posterior, respectively, of a first bore 724 of the tibial baseplate. Other than the inclusion of the anterior and posterior stops, tibial baseplate 714 may be the same as tibial baseplate 414 and the description herein of the other features of tibial baseplate 414 applies to tibial baseplate 714, and will not be repeated here. Another embodiment of the prosthesis may include a baseplate with only one anterior or posterior stop.

Figure 48B:
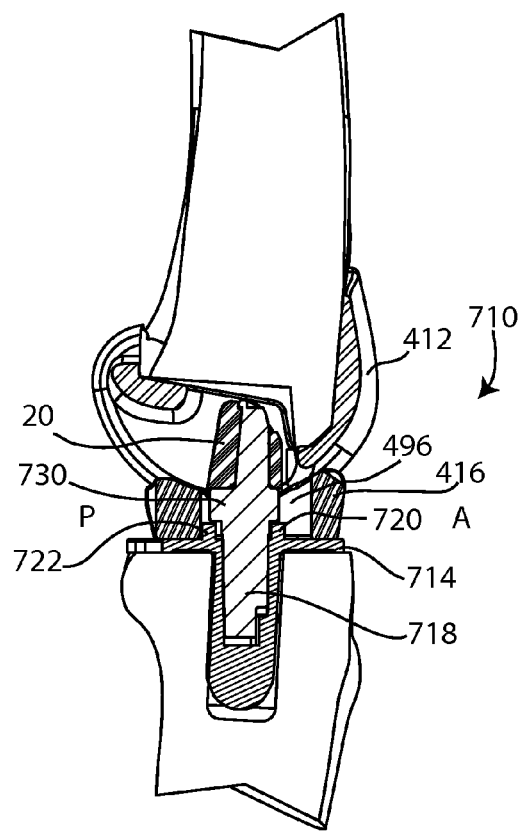
FIG. 48B is an medial cross-sectional view of the prosthesis of FIG. 46 taken along line A-A.

The stops 720, 722 are sized, shaped and positioned such that when tibial insert 416 is properly assembled with tibial baseplate 714, the stops are located within tibial insert channel 496, as seen in FIG. 47B. In FIG. 47B, sleeve 20 and femoral implant 412 are not depicted so that the interaction of the cam post core 718 with stops 720, 722 can be seen. During extension, as seen in FIGS. 47B and 48B, the tibial insert 416 is rotated general anteriorly. The posterior stop 722 on tibial baseplate 714 may abut against a posterior channel end wall 495 to stop rotation of the insert. Conversely, during flexion, tibial insert 416 rotates generally posteriorly, and the anterior stop 720 may contact an anterior channel end wall 493 to prohibit further posterior movement of the insert. These motion limiting stops may result in less stress to the cam post assembly, compared to configurations in which the rotational motion stops are provided between the post and the tibial insert. The channel 494 and cam post core 718 may be sized and shaped so that there is no direct contact between them when prosthesis 710 is assembled and articulated properly. To that end, the length of an intermediate block portion 730 on cam post core 718 may be shorter than that of other cam post cores described herein. In all other aspects, cam post core 718 may be the same as cam post core 18.

Figure 49:
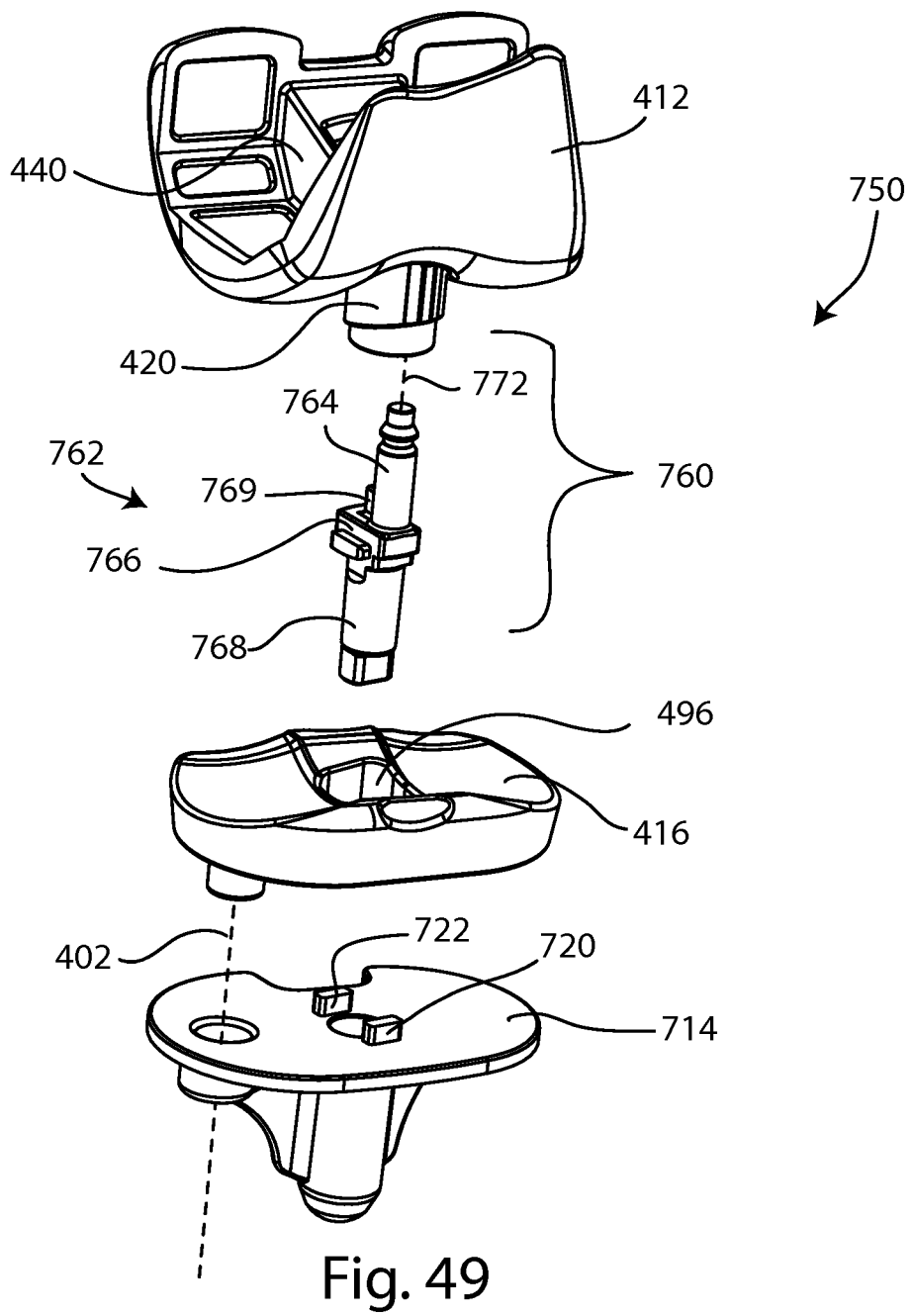
FIG. 49 is a perspective exploded view of an alternate embodiment of a knee prosthesis including a femoral implant, a tibial bearing insert, a cam post, a sleeve, and a tibial baseplate.
Figure 50:
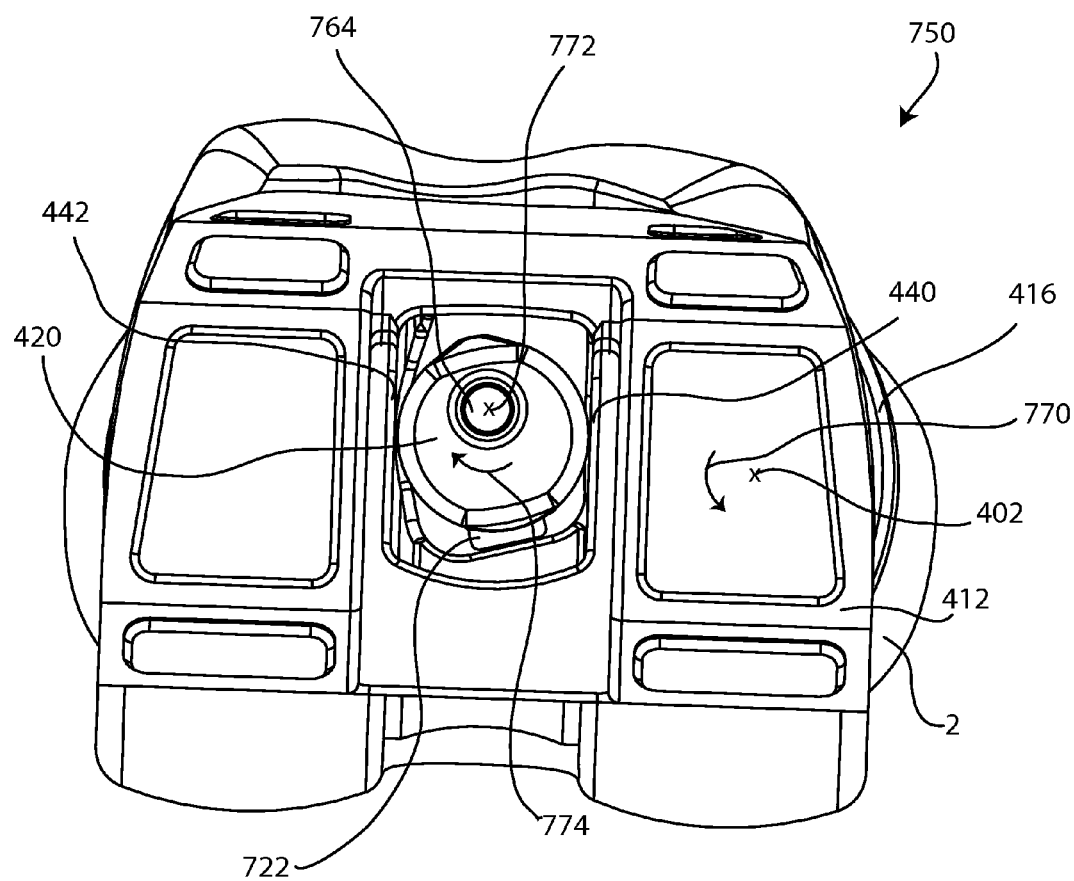
FIG. 50 is a superior view of the prosthesis of FIG. 49 implanted in a tibia, the prosthesis in an extension position.

Referring to FIGS. 49 and 50, another embodiment of a knee prosthesis includes a tibial baseplate with a motion limiting mechanism, and a modular cam post assembly having a rotatable sleeve providing varus/valgus support to the femoral implant. The prosthesis can be either a mobile bearing prosthetic knee or a fixed bearing prosthetic knee (if, for example, combined with the elements set forth in FIG. 51). Prosthesis 750 includes femoral implant 412, tibial baseplate 714, tibial insert 416, and cam post assembly 760, which includes cam post core 762 and sleeve 420. As described above for other embodiments including prostheses 410 and 610, knee prosthesis 750 provides rotation of the tibial insert about the medial rotation axis, varus-valgus stability, and greater rollback on the lateral side than the medial side. As described above for knee prosthesis 710, the anterior and posterior stops 720, 722 provide limits to the rotation of tibial insert 416 relative to tibial baseplate 714. As described previously for knee prosthesis 410, cam post assembly 760 cooperates with the intercondylar box walls 440, 442 of femoral implant 412 to provide varus/valgus support to the femoral implant and femur.

Cam post assembly 760 includes cam post core 762 and sleeve 420. Cam post core 762 further comprises superior post portion 764, intermediate block portion 766, and inferior post portion 768. The intermediate block portion 766 may be sized so that there is no direct contact between it and walls of channel 496 of bearing insert 416, when prosthesis 760 is assembled and articulated properly. To that end, the length of the intermediate block portion 766 on cam post core 762 may be shorter than the intermediate block portion of cam post core 418 described herein. In all other aspects, cam post core 718 may be the same as cam post core 418. The central longitudinal axis of superior post portion 764 defines a second rotation axis 772 about which sleeve 420 is rotatable. Second rotation axis 772 is separate from and not coaxial with first rotation axis 402.

FIG. 50 depicts a top-down view of knee prosthesis 750 implanted on tibia 2; the femur is not shown in order to provide an unimpeded view of all components of the prosthesis. The prosthesis is shown in extension, with tibial insert 416 rotated anteriorly and posterior top 722 prohibiting further anterior rotation of the insert. During articulation of the prosthesis in flexion, tibial insert 416 rotates posteriorly about rotation axis 402, in a first direction indicated by arrow 770. Also during flexion, sleeve 420 may rotate anteriorly about second rotation axis 772 in a second direction indicated by arrow 774, which may be opposite the first direction. Tab 769 provides a rotational stop for rotation of sleeve 420, as described previously for cam post assembly 419. As also described for previous embodiments, the cam post assembly 760 provides varus/valgus support, which may include slight varus/valgus motion, for femoral implant 412.

It is appreciated that the any enabling combination of elements disclosed herein may also be applied to a non-mobile, or fixed bearing knee prosthesis. FIG. 51 provides one non-limiting example of a fixed bearing knee prosthesis. Knee prosthesis 810 includes femoral implant 412, tibial insert 816, support post assembly 419, and tibial baseplate 814. As described above for other embodiments including prostheses 410, 610, and 710, knee prosthesis 810 may provide varus-valgus stability, and greater rollback on the lateral side than the medial side. The prosthesis includes a structure engaging the tibial baseplate and the tibial bearing to limit motion between the tibial baseplate and the tibial bearing. Rim 818 forms a structure projecting superiorly from the tibial baseplate 814 to engage the tibial bearing 412. In the embodiment depicted in FIG. 51, rim 818 is formed along the entire perimeter of baseplate 814; in other embodiments the rim may be formed along only a portion, or portions of the perimeter. Tibial insert 816 includes a recess 820 formed along the perimeter of the insert 816. When tibial insert 816 is assembled together with tibial baseplate 814, rim 818 fits into recess 820, providing a motion limiting engagement between the two components. During articulation of the knee prosthesis 810, the position of the tibial bearing 816 is fixed relative to the tibial baseplate 816. In the embodiment of FIG. 51, any motion between tibial insert 816 and tibial baseplate 814 may be completely prohibited; in other embodiments motion between the insert and the baseplate may be partially limited, with some motion allowed in one or more directions. In some embodiments the motion limiting structure may be a projection offset from the perimeter, or intersecting the perimeter. In some embodiments the motion limiting structure may include a projection or protrusion formed on one component which engages a recess, slot or channel on a second component. In some embodiments the motion limiting structure may be formed on the tibial baseplate, the tibial insert, and/or the support post assembly.

The present invention may be embodied in other specific forms without departing from its spirit or essential characteristics. It is appreciated that various features of the above described examples and embodiments may be mixed and matched to form a variety of other combinations and alternatives; for example, using the cam post 19 with the tibial insert 116. In other non-limiting examples, tibial baseplate 714 may be used with other tibial inserts herein besides tibial insert 416 to provide stops to rotational motion. Tibial baseplates 14, 114, 214, 314, 414, 714 or 814 may be combined with any of the cam posts or cam post assemblies disclosed herein, providing a modular prosthetic. Tibial insert 616 may be used with other cam posts herein besides cam post 618 to prevent lifting of tibial insert 616 off of the tibial baseplate. Any knee prosthesis disclosed herein may be a fixed bearing prosthesis by combination with tibial bearing 816 and/or tibial baseplate 814. It is also appreciated that this system should not be limited simply to total knee prosthesis. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A knee replacement system comprising:
   a femoral knee implant comprising a pair of condyles and a bone facing side shaped to lie against a resected surface of a femur; and
   a tibial baseplate comprising a tibia facing surface and a superior surface, wherein the tibia facing surface is shaped to lie against a resected surface of a tibia;
   a tibial bearing having a baseplate facing side, a condylar articulation side, and a channel which passes through the tibial bearing along a direction generally perpendicular to the baseplate facing side;
   a support post assembly comprising a post which projects superiorly relative to the superior surface of the tibial baseplate and extends through the channel of the tibial bearing;
   a sleeve mounted over the post and rotatable about the post;
   a first rotation axis extending through the tibial baseplate and the tibial bearing substantially perpendicular to the superior surface of the tibial baseplate and the baseplate facing side of the tibial bearing, the first rotation axis medially displaced relative to the geometric centers of the tibial baseplate and the tibial bearing, wherein the tibial bearing rotates relative to the tibial baseplate about the medial first rotation axis during articulation of the knee replacement system; and
   a second rotation axis separate from and not co-axial with the first rotation axis, wherein the sleeve rotates about the second rotation axis.

2. The knee replacement system of claim 1, further comprising a structure which directly contacts a wall of the channel to limit the rotation of the bearing relative to the tibial baseplate.

3. The knee replacement system of claim 1, wherein the post is attached to the tibial baseplate through a Morse taper fitting.

4. The knee replacement system of claim 1, wherein the post comprises a key feature and the tibial baseplate comprises a corresponding key feature, wherein the key features directly engage each other to prevent rotation of the post relative to the tibial baseplate.

5. The knee replacement system of claim 1, wherein the sleeve comprises a sleeve bore and the post is received within the sleeve bore.

6. A knee replacement system comprising:
   a femoral knee implant comprising a pair of condyles and a bone facing side shaped to lie against a resected surface of a femur; and
   a tibial baseplate comprising a tibia facing surface and a superior surface, wherein the tibia facing surface is shaped to lie against a resected surface of a tibia;
   a tibial bearing having a baseplate facing side, a condylar articulation side, and a channel which passes through the tibial bearing along a direction generally perpendicular to the baseplate facing side;
   a support post assembly comprising a post which projects superiorly relative to the superior surface of the tibial baseplate and extends through the channel of the tibial bearing, the support post assembly further comprising a sleeve removably mounted over the post and rotatable about the post, wherein the sleeve comprises a sleeve bore and the post is received within the sleeve bore;
   a structure engaging the tibial baseplate and the tibial bearing to limit motion between the tibial baseplate and the tibial bearing;
   a first rotation axis extending through the tibial baseplate and the tibial bearing substantially perpendicular to the superior surface of the tibial baseplate and the baseplate facing side of the tibial bearing, the first rotation axis medially displaced relative to the geometric centers of the tibial baseplate and the tibial bearing, wherein the tibial bearing rotates relative to the tibial baseplate about the medial first rotation axis during articulation of the knee replacement system; and
a second rotation axis separate from and not co-axial with the first rotation axis, wherein the sleeve rotates about the second rotation axis.

7. The knee replacement system of claim 6, wherein during articulation of the knee replacement system the bearing rotates relative to the tibial baseplate in a first direction and the sleeve rotates about the post in a second direction, the second direction opposite from the first direction.

8. The knee replacement system of claim 6, wherein the structure is formed on the tibial baseplate, and the structure directly contacts a wall of the channel to limit rotation of the bearing relative to the tibial baseplate.

9. The knee replacement system of claim 8, wherein the structure projects superiorly from the tibial baseplate.

10. A knee replacement system comprising:
a femoral implant comprising a pair of condyles and a bone facing side shaped to lie against a resected surface of a femur; and
a tibial baseplate comprising a tibia facing surface and a superior surface, wherein the tibia facing surface is shaped to lie against a resected tibial surface;
a tibial bearing having a baseplate facing side, a condylar articulation side, and a channel which passes through the tibial bearing along a direction generally perpendicular to the baseplate facing side;
a support post assembly comprising a post which projects superiorly relative to the superior surface of the tibial baseplate and extends through the channel of the tibial bearing, the support post assembly further comprising a sleeve removably mounted over the post and rotatable about the post, wherein the sleeve comprises a sleeve bore and the post is received within the sleeve bore, wherein the support post assembly engages with the femoral implant to provide varus/valgus stability to the femoral implant;
a structure engaging the tibial baseplate and the tibial bearing to limit motion between the tibial baseplate and the tibial bearing; and
a second motion limiting structure, wherein the second motion limiting structure limits the rotation of the sleeve relative to the post to a predetermined angle, wherein during articulation of the knee replacement system the tibial bearing rotates relative to the tibial baseplate in a first direction and the sleeve rotates about the post in a second direction, the second direction opposite from the first direction.

11. The knee replacement system of claim 10, further comprising a rotation axis extending through the tibial baseplate and the tibial bearing substantially perpendicular to the superior surface of the tibial baseplate and the baseplate facing side of the tibial bearing, the rotation axis medially displaced relative to the geometric centers of the tibial baseplate and the tibial bearing, wherein the tibial bearing rotates relative to the tibial baseplate about the medial rotation axis during articulation of the knee replacement system.

12. The knee replacement system of claim 11, wherein the structure directly contacts a wall of the channel to limit rotation of the bearing relative to the tibial baseplate.

13. The knee replacement system of claim 10, wherein the support post assembly directly contacts the femoral implant to provide the varus/valgus stability to the femoral implant.

14. The knee replacement system of claim 13, wherein the femoral component comprises an intercondylar wall, wherein the sleeve contacts the intercondylar wall to provide the varus/valgus stability to the femoral implant.

15. The knee replacement system of claim 10, wherein the structure projects superiorly from the tibial baseplate.

16. A knee replacement system comprising:
a femoral knee implant comprising a pair of condyles and a bone facing side shaped to lie against a resected surface of a femur; and
a tibial baseplate comprising a tibia facing surface and a superior surface, wherein the tibia facing surface is shaped to lie against a resected surface of a tibia;
a tibial bearing having a baseplate facing side, a condylar articulation side, and a channel which passes through the tibial bearing along a direction generally perpendicular to the baseplate facing side;
a support post assembly comprising a post which projects superiorly relative to the superior surface of the tibial baseplate and extends through the channel of the tibial bearing, the support post assembly further comprising a sleeve removably mounted over the post and rotatable about the post, wherein the sleeve comprises a sleeve bore and the post is received within the sleeve bore;
a structure engaging the tibial baseplate and the tibial bearing to limit motion between the tibial baseplate and the tibial bearing; and
a first rotation axis extending through the tibial baseplate and the tibial bearing substantially perpendicular to the superior surface of the tibial baseplate and the baseplate facing side of the tibial bearing, the first rotation axis medially displaced relative to the geometric centers of the tibial baseplate and the tibial bearing, wherein during articulation of the knee replacement system the bearing rotates relative to the tibial baseplate about the first rotation axis in a first direction, and the sleeve rotates about the post in a second direction, the second direction opposite from the first direction.

17. The knee replacement system of claim 16, further comprising a second rotation axis separate from and not co-axial with the first rotation axis, wherein the sleeve rotates about the second rotation axis.

18. The knee replacement system of claim 16, wherein the structure is formed on the tibial baseplate, and the structure directly contacts a wall of the channel to limit rotation of the bearing relative to the tibial baseplate.

19. The knee replacement system of claim 16, wherein the structure projects superiorly from the tibial baseplate.

* * * * *